(12) United States Patent
Pfiffner

(10) Patent No.: US 12,017,084 B2
(45) Date of Patent: *Jun. 25, 2024

(54) PHOTOBIOMODULATION THERAPY DEVICE ACCESSORIES

(71) Applicant: Joovv, Inc., San Clemente, CA (US)

(72) Inventor: Greg Pfiffner, San Clemente, CA (US)

(73) Assignee: Joovv, Inc., Carson City, NV (US)

( * ) Notice: Subject to any disclaimer, the term of this patent is extended or adjusted under 35 U.S.C. 154(b) by 7 days.

This patent is subject to a terminal disclaimer.

(21) Appl. No.: 17/950,015

(22) Filed: Sep. 21, 2022

(65) Prior Publication Data

US 2023/0027865 A1 Jan. 26, 2023

Related U.S. Application Data

(63) Continuation of application No. 17/559,874, filed on Dec. 22, 2021, now Pat. No. 11,458,328, which is a
(Continued)

(51) Int. Cl.
*A61N 5/06* (2006.01)

(52) U.S. Cl.
CPC ........ *A61N 5/06* (2013.01); *A61N 2005/0629* (2013.01); *A61N 2005/064* (2013.01);
(Continued)

(58) Field of Classification Search
CPC .............. A61N 5/06; A61N 2005/0633; A61N 2005/0659; A61N 2005/0663;
(Continued)

(56) References Cited

U.S. PATENT DOCUMENTS

| 845,917 A | * | 3/1907 | Worley et al. ....... A47B 96/067 108/108 |
| 1,660,794 A | | 2/1928 | Walter |

(Continued)

FOREIGN PATENT DOCUMENTS

| KR | 101244434 B1 | 3/2013 |
| WO | 2008131343 | 10/2008 |

(Continued)

OTHER PUBLICATIONS

Kind LED Grow Lights, "Kind LED Grow Lights K5 Series Instructions"—Downloaded on Oct. 1, 2018 from https://www.kindledgrowlights.com/pages/k5-setup.
(Continued)

*Primary Examiner* — Muhammad Ijaz
(74) *Attorney, Agent, or Firm* — Gallium Law; Wesley Schwie; Isabel Fox

(57) ABSTRACT

A light therapy device mounting system may include an elongate pole comprising a plurality of holes, a first portion, a second portion, and a coupler configured to couple the first portion and the second portion. In some embodiments, the system includes a slider mount slidably coupled to the elongate pole via at least one hole of the plurality of holes, a top bracket slidably coupled to the first portion of the elongate pole, and a bottom bracket slidably coupled to the second portion of the elongate pole. The top bracket may include a top hook for receiving a top portion of a door, and the bottom bracket may include a bottom hook for receiving a bottom portion of the door.

20 Claims, 31 Drawing Sheets

Related U.S. Application Data continuation-in-part of application No. 17/027,338, filed on Sep. 21, 2020, now Pat. No. 11,207,543, which is a continuation-in-part of application No. 16/904,243, filed on Jun. 17, 2020, now abandoned, and a continuation-in-part of application No. 16/598,033, filed on Oct. 10, 2019, now Pat. No. 11,253,719, which is a continuation of application No. 16/584,784, filed on Sep. 26, 2019, now Pat. No. 10,639,495, and a continuation of application No. 16/227,289, filed on Dec. 20, 2018, now Pat. No. 10,478,635, said application No. 17/027,338 is a continuation-in-part of application No. 16/167,385, filed on Oct. 22, 2018, now Pat. No. 11,033,752.

(60) Provisional application No. 62/872,835, filed on Jul. 11, 2019, provisional application No. 62/863,247, filed on Jun. 18, 2019.

(52) U.S. Cl.
CPC ............... *A61N 2005/0659* (2013.01); *A61N 2005/0663* (2013.01)

(58) Field of Classification Search
CPC ...... A61N 2005/0629; A61N 2005/064; A61N 2005/0662; F16M 13/00; F16M 2200/00; F16M 11/046; F16M 11/041; F16M 11/10; F16M 13/022; G06F 1/166
USPC ............ 248/658, 480, 155.3, 420, 429, 432, 248/287.1, 307, 320, 339
See application file for complete search history.

(56) References Cited

U.S. PATENT DOCUMENTS

| | | | |
|---|---|---|---|
| 2,327,346 A | 8/1943 | Frank | |
| 3,416,852 A | 12/1968 | Goldbeck | |
| 3,917,923 A * | 11/1975 | Shoup | G07C 13/00 |
| | | | 235/1 D |
| 4,312,361 A | 1/1982 | Nicholson | |
| 4,339,219 A * | 7/1982 | Lay | E04F 21/1822 |
| | | | 414/11 |
| 4,673,152 A | 6/1987 | Brown | |
| 4,736,555 A | 4/1988 | Nagare | |
| 4,740,707 A * | 4/1988 | Thaw | A61N 5/0614 |
| | | | 607/94 |
| 4,844,069 A | 7/1989 | Mori | |
| 5,515,900 A | 5/1996 | West | |
| 5,616,140 A | 4/1997 | Prescott | |
| 5,645,578 A | 7/1997 | Daffer | |
| 5,697,595 A * | 12/1997 | Sperber | A47B 97/001 |
| | | | 248/452 |
| 5,698,866 A | 12/1997 | Doiron | |
| 5,733,032 A | 3/1998 | Bolta | |
| 5,759,139 A * | 6/1998 | Wright | A63B 21/045 |
| | | | 482/121 |
| 5,761,839 A | 6/1998 | Heikkila | |
| 5,776,048 A * | 7/1998 | Jo | A61G 7/0573 |
| | | | 600/21 |
| 5,800,478 A | 9/1998 | Chen | |
| 5,992,417 A * | 11/1999 | Toepel | A61B 90/04 |
| | | | 128/846 |
| 5,996,728 A | 12/1999 | Stark | |
| 6,054,968 A | 4/2000 | De Matteo | |
| 6,290,713 B1 | 9/2001 | Russell | |
| 6,370,021 B1 * | 4/2002 | Hinzpeter | H05K 5/0017 |
| | | | 361/740 |
| 6,494,910 B1 | 12/2002 | Ganem | |
| 6,508,262 B1 * | 1/2003 | Takayama | E04H 15/50 |
| | | | 135/912 |
| 6,626,932 B2 | 9/2003 | Whitehurst | |
| 6,645,230 B2 | 11/2003 | Whitehurst | |
| 6,663,659 B2 | 12/2003 | McDaniel | |
| 6,853,151 B2 | 2/2005 | Leong | |
| 6,870,673 B2 | 3/2005 | Cromer | |
| 6,896,693 B2 | 5/2005 | Sullivan | |
| 6,955,684 B2 | 10/2005 | Savage | |
| 7,033,381 B1 | 4/2006 | Larsen | |
| 7,578,600 B2 | 8/2009 | Czajkowski | |
| 7,621,544 B2 * | 11/2009 | Rossini | F16M 11/22 |
| | | | 280/47.35 |
| 7,863,641 B2 | 1/2011 | Dahm | |
| 7,932,482 B2 | 4/2011 | Norwood | |
| 8,043,349 B2 | 10/2011 | Springer | |
| 8,066,403 B2 | 11/2011 | Sanfilippo | |
| 8,337,538 B1 | 12/2012 | Ford | |
| 8,376,602 B2 | 2/2013 | Klipstein | |
| 8,425,577 B2 | 4/2013 | Vargas | |
| 8,454,214 B2 | 6/2013 | Kazaoka | |
| 8,481,982 B2 | 7/2013 | Johnson | |
| 8,763,963 B1 * | 7/2014 | Li | F16M 11/00 |
| | | | 248/161 |
| 9,169,960 B2 * | 10/2015 | Håkansson | F16M 11/24 |
| 9,227,082 B2 | 1/2016 | Mcdaniel | |
| 9,311,847 B2 | 4/2016 | Hall | |
| 9,353,924 B2 | 5/2016 | Scarlata | |
| 9,399,146 B2 | 7/2016 | Jones | |
| 9,416,551 B2 | 8/2016 | Hall | |
| 9,440,041 B1 | 9/2016 | Lacayo | |
| 9,551,893 B2 | 1/2017 | An | |
| 9,707,665 B1 * | 7/2017 | Smith | B25B 1/241 |
| 9,852,666 B2 | 12/2017 | Ward | |
| 9,884,204 B1 | 2/2018 | Dolleris | |
| 9,943,042 B2 | 4/2018 | Thosteson | |
| 10,064,940 B2 | 9/2018 | Nager | |
| 10,357,567 B1 * | 7/2019 | Lundahl | A61K 41/0061 |
| 10,363,434 B2 | 7/2019 | Marchese | |
| 10,420,292 B1 * | 9/2019 | Ehlers | B25B 5/068 |
| 10,440,794 B2 | 10/2019 | Alexander | |
| 10,478,635 B1 * | 11/2019 | Nelson | A61N 5/0616 |
| D877,919 S | 3/2020 | Strahan | |
| D877,920 S | 3/2020 | Nelson | |
| D877,921 S | 3/2020 | Nelson | |
| D877,922 S | 3/2020 | Strahan | |
| D877,923 S | 3/2020 | Strahan | |
| 10,596,437 B2 * | 3/2020 | Hollist | A63B 69/00 |
| 10,625,537 B1 * | 4/2020 | Dawson | G09F 15/0056 |
| 10,632,325 B2 | 4/2020 | Lim | |
| D884,697 S * | 5/2020 | Park | D14/375 |
| 10,639,495 B1 | 5/2020 | Nelson | |
| 10,672,306 B1 | 6/2020 | Whidden | |
| 10,706,770 B2 | 7/2020 | Hall | |
| D892,343 S | 8/2020 | Strahan | |
| D892,344 S | 8/2020 | Nelson | |
| D892,345 S | 8/2020 | Strahan | |
| D893,737 S | 8/2020 | Nelson | |
| D895,822 S * | 9/2020 | Nelson | D24/209 |
| 10,828,505 B2 * | 11/2020 | Nelson | A61N 5/0616 |
| 10,881,550 B2 | 1/2021 | Tedford | |
| 11,033,752 B2 * | 6/2021 | Strahan | A61N 5/0616 |
| 11,207,543 B2 * | 12/2021 | Pfiffner | A61N 5/06 |
| 11,253,719 B2 | 2/2022 | Strahan | |
| 11,458,328 B2 | 9/2022 | Pfiffner | |
| 11,524,172 B2 | 11/2022 | Strahan | |
| 2002/0198575 A1 | 12/2002 | Sullivan | |
| 2003/0009205 A1 | 1/2003 | Biel | |
| 2003/0188378 A1 | 10/2003 | Brunelle | |
| 2003/0216795 A1 | 11/2003 | Harth | |
| 2003/0233138 A1 | 12/2003 | Spooner | |
| 2004/0008523 A1 | 1/2004 | Butler | |
| 2004/0014199 A1 | 1/2004 | Streeter | |
| 2004/0068305 A1 | 4/2004 | Bansal | |
| 2004/0162596 A1 | 8/2004 | Altshuler | |
| 2004/0188573 A1 * | 9/2004 | Weatherly | F16M 11/42 |
| | | | 248/917 |
| 2004/0193234 A1 | 9/2004 | Butler | |
| 2005/0075703 A1 | 4/2005 | Larsen | |
| 2005/0085875 A1 | 4/2005 | Van Zuylen | |
| 2005/0116667 A1 | 6/2005 | Mueller | |
| 2005/0210722 A1 | 9/2005 | Graef | |

(56) References Cited

U.S. PATENT DOCUMENTS

| | | | |
|---|---|---|---|
| 2005/0223665 A1* | 10/2005 | Maas | E04H 1/1272 52/239 |
| 2005/0230573 A1* | 10/2005 | Ligertwood | A47B 21/00 248/176.1 |
| 2005/0237739 A1 | 10/2005 | Lee | |
| 2005/0275178 A1* | 12/2005 | Huesdash | F16M 11/42 280/47.35 |
| 2006/0007059 A1 | 1/2006 | Bell | |
| 2006/0020308 A1 | 1/2006 | Muldner | |
| 2006/0030908 A1 | 2/2006 | Powell | |
| 2006/0217787 A1 | 9/2006 | Olson | |
| 2006/0217789 A1 | 9/2006 | Perez | |
| 2006/0229689 A1* | 10/2006 | Ferguson | A61N 5/0616 607/91 |
| 2006/0241726 A1 | 10/2006 | Whitehurst | |
| 2007/0038206 A1 | 2/2007 | Altshuler | |
| 2007/0068055 A1 | 3/2007 | Segan | |
| 2007/0084108 A1* | 4/2007 | Hertlein | A01G 9/122 47/47 |
| 2007/0129776 A1 | 6/2007 | Robins | |
| 2007/0129777 A1 | 6/2007 | Bolta | |
| 2007/0217199 A1 | 9/2007 | Adam | |
| 2007/0276455 A1 | 11/2007 | Fiset | |
| 2007/0278360 A1* | 12/2007 | Chen | A47B 57/54 248/121 |
| 2008/0046044 A1 | 2/2008 | Jahnigen | |
| 2008/0091250 A1 | 4/2008 | Powell | |
| 2008/0114418 A1 | 5/2008 | Myeong | |
| 2008/0119831 A1 | 5/2008 | Myeong | |
| 2008/0141572 A1 | 6/2008 | Tomich | |
| 2008/0210659 A1 | 9/2008 | McKinney | |
| 2008/0269849 A1 | 10/2008 | Lewis | |
| 2008/0306576 A1 | 12/2008 | Boyden | |
| 2008/0312721 A1 | 12/2008 | Lemieux | |
| 2009/0012588 A1* | 1/2009 | Springer, Jr. | A61N 5/06 607/94 |
| 2009/0058153 A1 | 3/2009 | Shafer | |
| 2009/0262533 A1 | 10/2009 | Liu | |
| 2009/0288340 A1 | 11/2009 | Hess | |
| 2009/0318908 A1 | 12/2009 | Van Pieterson | |
| 2010/0045175 A1 | 2/2010 | Mathai | |
| 2010/0045189 A1 | 2/2010 | Storch | |
| 2010/0076529 A1 | 3/2010 | Tucker | |
| 2010/0265711 A1 | 10/2010 | Lee | |
| 2010/0277105 A1 | 11/2010 | Oyama | |
| 2010/0303603 A1* | 12/2010 | Galante | F16M 13/00 414/811 |
| 2010/0309659 A1 | 12/2010 | Jenny | |
| 2010/0324611 A1 | 12/2010 | Deming | |
| 2011/0054573 A1 | 3/2011 | Mitchell | |
| 2011/0176297 A1 | 7/2011 | Hsia | |
| 2012/0019490 A1 | 1/2012 | Huang | |
| 2012/0020109 A1 | 1/2012 | Kim | |
| 2012/0030873 A1 | 2/2012 | Turtzo | |
| 2012/0075871 A1 | 3/2012 | Chen | |
| 2012/0086941 A1* | 4/2012 | Hayes | G01M 11/061 356/399 |
| 2012/0104977 A1 | 5/2012 | Mckenzie | |
| 2012/0243227 A1 | 9/2012 | Shimizu | |
| 2012/0283622 A1 | 11/2012 | Nath | |
| 2012/0296260 A1 | 11/2012 | Vizethum | |
| 2013/0101953 A1 | 4/2013 | Stone | |
| 2013/0163235 A1 | 6/2013 | Chuang | |
| 2013/0172963 A1 | 7/2013 | Moffat | |
| 2013/0190842 A1 | 7/2013 | Hacco | |
| 2013/0229802 A1 | 9/2013 | Fukushima | |
| 2013/0279160 A1 | 10/2013 | Myers | |
| 2013/0282082 A1 | 10/2013 | Daijo | |
| 2013/0289673 A1 | 10/2013 | Matsubara | |
| 2013/0301264 A1 | 11/2013 | Emericus | |
| 2013/0304019 A1 | 11/2013 | Cooper | |
| 2013/0304164 A1 | 11/2013 | Zanata | |
| 2014/0031906 A1 | 1/2014 | Brezinski | |
| 2014/0049942 A1 | 2/2014 | Chilton | |
| 2014/0081357 A1 | 3/2014 | Legerton | |
| 2014/0190537 A1 | 7/2014 | Benda | |
| 2014/0197124 A1 | 7/2014 | Mcphillips | |
| 2014/0202493 A1 | 7/2014 | Zelickson | |
| 2014/0226329 A1 | 8/2014 | Oraw | |
| 2014/0241008 A1 | 8/2014 | Kim | |
| 2014/0303547 A1 | 10/2014 | Loupis | |
| 2015/0051671 A1 | 2/2015 | Browne | |
| 2015/0062900 A1 | 3/2015 | Ferro | |
| 2015/0112411 A1 | 4/2015 | Beckman | |
| 2015/0198298 A1 | 7/2015 | Scarlata | |
| 2015/0202455 A1 | 7/2015 | Williams | |
| 2015/0265846 A1 | 9/2015 | Baird | |
| 2015/0267907 A1 | 9/2015 | Thompson | |
| 2015/0297914 A1 | 10/2015 | Hamid | |
| 2015/0307332 A1 | 10/2015 | Huang | |
| 2016/0015999 A1 | 1/2016 | Dabney | |
| 2016/0016001 A1* | 1/2016 | Loupis | H05B 45/20 604/20 |
| 2016/0076708 A1 | 3/2016 | Shirilla | |
| 2016/0106950 A1 | 4/2016 | Vasapollo | |
| 2016/0158574 A1 | 6/2016 | Eckhouse | |
| 2016/0175610 A1 | 6/2016 | Livingston | |
| 2016/0232822 A1 | 8/2016 | Ward | |
| 2016/0286616 A1 | 9/2016 | Van De Ven | |
| 2016/0312945 A1* | 10/2016 | Freudinger | A63B 21/4023 |
| 2016/0367833 A1 | 12/2016 | Salinas | |
| 2017/0007844 A1 | 1/2017 | Kaandorp | |
| 2017/0007846 A1 | 1/2017 | Rabin | |
| 2017/0028216 A1 | 2/2017 | Medendorp | |
| 2017/0053570 A1 | 2/2017 | Cox | |
| 2017/0074474 A1 | 3/2017 | Bailey | |
| 2017/0080246 A1 | 3/2017 | Knight | |
| 2017/0106205 A1* | 4/2017 | Boyajian | A61N 5/062 |
| 2017/0118838 A1 | 4/2017 | Williams | |
| 2017/0131693 A1 | 5/2017 | Shurtleff | |
| 2017/0274222 A1 | 9/2017 | Geyer | |
| 2018/0008839 A1 | 1/2018 | Hamid | |
| 2018/0036553 A1 | 2/2018 | Shiibashi | |
| 2018/0043178 A1 | 2/2018 | Iguchi | |
| 2018/0051862 A1 | 2/2018 | Meumann | |
| 2018/0056087 A1 | 3/2018 | Ribeiro | |
| 2018/0111001 A1 | 4/2018 | Segel | |
| 2018/0117355 A1* | 5/2018 | Loupis | A61N 5/0616 |
| 2018/0141499 A1* | 5/2018 | Newman | B60R 11/0235 |
| 2018/0236259 A1* | 8/2018 | Nelson | A61N 5/0616 |
| 2018/0243583 A1* | 8/2018 | Duggins | A61B 5/14546 |
| 2018/0288840 A1 | 10/2018 | Kogure | |
| 2018/0292055 A1 | 10/2018 | Moioli | |
| 2018/0345034 A1 | 12/2018 | Butzloff | |
| 2018/0363837 A1* | 12/2018 | Roberts | F16M 13/00 |
| 2019/0030359 A1 | 1/2019 | Dijkstra | |
| 2019/0054946 A1* | 2/2019 | Yue | B62B 3/0612 |
| 2019/0167519 A1 | 6/2019 | Kaps | |
| 2019/0388707 A1 | 12/2019 | Shen Farber | |
| 2020/0060868 A1 | 2/2020 | Sivan | |
| 2020/0086135 A1 | 3/2020 | Johnson | |
| 2020/0121944 A1* | 4/2020 | Strahan | A61N 5/0616 |
| 2020/0197718 A1 | 6/2020 | Strahan | |
| 2020/0269065 A1 | 8/2020 | Broeng | |
| 2020/0324104 A1 | 10/2020 | Labuschagne | |
| 2020/0353273 A1 | 11/2020 | Zucco | |
| 2020/0360714 A1 | 11/2020 | Shterzer | |
| 2020/0398075 A1 | 12/2020 | Pfiffner | |
| 2021/0001140 A1* | 1/2021 | Pfiffner | F16M 13/022 |
| 2021/0001141 A1 | 1/2021 | Pfiffner | |
| 2022/0111225 A1 | 4/2022 | Pfiffner | |
| 2022/0161045 A1 | 5/2022 | Strahan | |

FOREIGN PATENT DOCUMENTS

| | | |
|---|---|---|
| WO | 2018152278 | 8/2018 |
| WO | 2020086494 | 4/2020 |

(56) References Cited

FOREIGN PATENT DOCUMENTS

| WO | 2020131235 | 6/2020 |
| WO | 2020257318 | 12/2020 |

OTHER PUBLICATIONS

Mouser Electronics, "Enclosures and Racks"—Downloaded on Oct. 4, 2018 from http://www.mouser.com/catalog/catalogusd/648/dload/pdf/ENCLOSECTION.pdf; prior art publication at least as of 2015.

Kind LED Grow Lights, "Kind LED Grow Lights—Voted Best LED Grow Lights of 2014!"—Downloaded on Oct. 2, 2018 from https://www.youtube.com/watch?v=NQDWBXIMxrk; prior part publication at least as of May 26, 2017.

Wrethaoffgrid, "Ohuhu Pair of ⅛" Grow Light Rope Hanger Review"—Downloaded on Oct. 5, 2018 from https://www.youtube.com/watch?v=gYCsNQ9LELM; prior art publication at least as of Sep. 29, 2016.

OXO, "OXO Over The Door Hooks & Racks"—Downloaded on Oct. 5, 2018 from https://www.youtube.com/watch?v=1WziS-a7LMI; prior part publication at least as of Feb. 11, 2014.

Woodworkers Store, "Swivel Mirror Screw"—Downloaded on Oct. 4, 2018 from http://go.rockler.com/tech/Swivel-Mirror-Screws-Instructions.pdf; prior art publication at least as of 1990.

Kind LED Grow Lights, "K5 Series XL1000 Indoor LED Grow Light"—Downloaded on Oct. 4, 2018 form https://www.kindledgrowlights.com/products/k5-xl1000.

Swedish LED Grow Lights, "300W Full Spectrum Led Grow Lights 85-265V 5730SMD USA/DE/AU/CA Stock Hanging Kit For Plants Veg Hydroponics Grow Led"—Downloaded on Jun. 5, 2017 from http://swedishledgrowlights.com/product/300w-full-spectrum-led-grow-lights-85-265v-5730smd-usa-de-au-ca-stock-hanging-kit-for-plants-veg-hydroponics-grow-led/.

Warp Light, "About the Quantum Light WARP 10®"—Downloaded on Sep. 19, 2019 from https://www.warp-light.com/Quantum_light_warp_10.html; prior art publication at least as of Nov. 30, 2012.

PCT International Search Report and Written Opinion in International Application No. PCT/US2018/018288, dated Oct. 29, 2018, 11 pages.

PCT International Preliminary Report on Patentability in International Application No. PCT/US2018/018288, dated Aug. 20, 2019, 9 pages.

PCT International Search Report and Written Opinion in International Application No. PCT/US2019/059845, dated Dec. 11, 2019, 7 pages.

PCT International Search Report and Written Opinion in International Application No. PCT/US2019/057292, dated Jan. 7, 2020, 8 pages.

PCT International Search Report and Written Opinion in International Application No. PCT/US2020/038187, dated Aug. 19, 2020, 8 pages.

PCT International Preliminary Report on Patentability in International Application No. PCT/US2019/057292, dated Apr. 27, 2021, 7 pages.

Green Envy Supply—How to Hang Light Reflector Using Rope Reel Ratchet Hangers—YouTube—video by user Green Envy Supply—First available Jan. 15, 2017—Available from Internet <URL: https://www.youtube.com/watch?v=W2z0m_70-Y0>.

JOOVV—"User Manual: Mini Solo Quad Elite"—Available at least as of Aug. 7, 2018—Downloaded Jan. 7, 2020—Available from the Internet <URL: https://cdn.shopify.com/s/files/1/1155/1380/files/Joovv_-_Mini_Solo_Duo_Quad_Elite_-_User_Manual.pdf>.

JOOVV—"Red Light Therapy for Your Entire Body"—Available at least as of Aug. 8, 2018—Downloaded Jan. 7, 2020—Available from the Internet <URL: https://web.archive.org/web/20180808180609/https://joov.com>.

JOOVV—"Choosing the Right Joovy"—YouTube video by user Joovv—First available Aug. 6, 2018—Downloaded Jan. 7, 2020—Available from the Internet <URL: https://www.youtube.com/watch?v=OIE9dOcM6mE&rel=0&showinfo=0&autoplay=0>.

JOOVV—"The New Joovy"—YouTube video—First available Oct. 1, 2018—Downloaded Jan. 7, 2020—Available from the Internet <URL: https://www.youtube.com/watch?time_continue=12&v=hpB6CNhd6Js&feature=emb_logo>.

\* cited by examiner

PHOTOBIOMODULATION THERAPY DEVICE ACCESSORIES

CROSS-REFERENCE TO RELATED APPLICATIONS

The entire contents of the following application are incorporated by reference herein: U.S. Non-Provisional Patent Application No. 17/559,874; filed Dec. 22, 2021; and entitled PHOTOBIOMODULATION THERAPY DEVICE ACCESSORIES.

The entire contents of the following application are incorporated by reference herein: U.S. Non-Provisional patent application Ser. No. 17/027,338; filed Sep. 21, 2020; issued as U.S. Pat. No. 11,207,543 on Dec. 28, 2021; and entitled PHOTOBIOMODULATION THERAPY DEVICE ACCESSORIES.

The entire contents of the following application are incorporated by reference herein: U.S. Provisional Patent Application No. 62/460,113; filed Feb. 17, 2017; and entitled THERAPEUTIC LIGHT SOURCE AND HANGING APPARATUS.

The entire contents of the following application are incorporated by reference herein: U.S. Non-Provisional patent application Ser. No. 15/616,028; filed Jun. 7, 2017; issued as U.S. Pat. No. 10,828,505 on Nov. 10, 2020; and entitled THERAPEUTIC LIGHT SOURCE AND HANGING APPARATUS.

The entire contents of the following application are incorporated by reference herein: PCT Patent Application No. PCT/US2018/018288; filed Mar. 1, 2018; and entitled THERAPEUTIC LIGHT SOURCE AND MOUNTING APPARATUS.

The entire contents of the following application are incorporated by reference herein: U.S. Non-Provisional patent application Ser. No. 16/167,385; filed Oct. 22, 2018; issued as U.S. Pat. No. 11,033,752 on Jun. 15, 2021; and entitled PHOTOBIOMODULATION THERAPY SYSTEMS AND METHODS.

The entire contents of the following application are incorporated by reference herein: PCT Patent Application No. PCT/US2019/057292; filed Oct. 21, 2019; and entitled PHOTOBIOMODULATION THERAPY SYSTEMS AND METHODS.

The entire contents of the following application are incorporated by reference herein: U.S. Non-Provisional patent application Ser. No. 16/227,289; filed Dec. 20, 2018; issued as U.S. Pat. No. 10,478,635 on Nov. 19, 2020; and entitled PHOTOBIOMODULATION THERAPY SYSTEMS AND METHODS.

The entire contents of the following application are incorporated by reference herein: U.S. Provisional Patent Application No. 62/863,247; filed Jun. 18, 2019; and entitled PHOTOBIOMODULATION THERAPY SYSTEMS AND METHODS.

The entire contents of the following application are incorporated by reference herein: U.S. Provisional Patent Application No. 62/872,835; filed Jul. 11, 2019; and entitled PHOTOBIOMODULATION THERAPY SYSTEMS AND METHODS.

The entire contents of the following application are incorporated by reference herein: U.S. Non-Provisional patent application Ser. No. 16/584,784; filed Sep. 26, 2019; issued as U.S. Pat. No. 10,639,495 on May 5, 2020; and entitled PHOTOBIOMODULATION THERAPY SYSTEMS AND METHODS.

The entire contents of the following application are incorporated by reference herein: U.S. Non-Provisional patent application Ser. No. 16/598,033; filed Oct. 10, 2019; issued as U.S. Pat. No. 11,253,719 on Feb. 2, 2022; and entitled PHOTOBIOMODULATION THERAPY SYSTEMS AND METHODS.

The entire contents of the following application are incorporated by reference herein: PCT Patent Application No. PCT/US2019/059845; filed Nov. 5, 2019; and entitled PHOTOBIOMODULATION THERAPY SYSTEMS AND METHODS.

The entire contents of the following application are incorporated by reference herein: U.S. Non-Provisional patent application Ser. No. 16/904,243; filed Jun. 17, 2020; and entitled PHOTOBIOMODULATION THERAPY SYSTEMS AND METHODS.

The entire contents of the following application are incorporated by reference herein: PCT Patent Application No. PCT/US2020/038187; filed Jun. 17, 2020; and entitled PHOTOBIOMODULATION THERAPY SYSTEMS AND METHODS.

BACKGROUND

Field

Various embodiments disclosed herein relate to accessories for light therapy devices. Certain embodiments relate to accessories, including stands, mounts, and brackets for hanging and/or supporting at least one light therapy device.

Description of Related Art

Photobiomodulation therapy (or light therapy) is a therapeutic technique that uses low-level wavelengths of light to improve health and treat various health conditions, including skin issues, such as wrinkles, scars, and persistent wounds, among many other conditions. Photobiomodulation therapy uses non-ionizing light sources, including lasers, light emitting diodes, and/or broadband light, in the visible (400-700 nm) and infrared (700-1100 nm) electromagnetic spectrum. Photobiomodulation is a nonthermal process involving endogenous chromophores eliciting photophysical (i.e., linear and nonlinear) and photochemical events at various biological scales. Similar to how plants use sunlight to heal and grow, humans and animals can harness these wavelengths of light and turn them into cellular energy. This treatment stimulates the body's natural healing processes.

Light therapy devices are sometimes available with a stand, mount, hanging mechanism, or similar device to support the light therapy device(s). Some examples include height-adjustable hanging mechanisms. There is a need for a broader range of supportive accessories for light therapy devices.

SUMMARY

The disclosure includes a light therapy device mounting system comprising an elongate pole including a plurality of holes, the elongate pole comprising a first end and a second end, a mounting device slidably coupled to the elongate pole via at least one hole of the plurality of holes, a top bracket slidably coupled to the first end of the elongate pole, wherein the top bracket comprises a top hook for receiving a top portion of a door, and a bottom bracket slidably coupled to the second end of the elongate pole, wherein the bottom bracket comprises a bottom hook for receiving a bottom portion of the door. In some embodiments, the light therapy device mounting system further comprises a light therapy device detachably coupled to the mounting device, wherein the light therapy device comprises a light therapy device bracket coupled to a back side of the light therapy device. The light therapy device bracket may include a plurality of keyhole brackets configured to receive at least one projection coupled to the mounting device.

In some embodiments, the mounting device comprises a hollow cylinder configured to slidably receive the elongate pole, a mounting device bracket coupled to the hollow cylinder, wherein the mounting device bracket is configured to detachably couple to a light therapy device via a plurality of keyhole brackets of a light therapy device bracket located on a back side of the light therapy device, a clip coupled to the hollow cylinder and the mounting device bracket, wherein the clip is located on a top portion of the mounting device bracket and is configured to retain the mounting device bracket, and a knob coupled to a side portion of the hollow cylinder, wherein the knob comprises a protrusion that extends into an inner portion of the hollow cylinder, and wherein the protrusion is configured to couple to at least one hole of the plurality of holes located on the elongate hole.

The elongate pole may be elongate in a first direction, and the knob may be configured to slide in a second direction perpendicular to the first direction, wherein sliding the knob in the second direction is configured to at last one of release and couple the protrusion to at least one hole of the plurality of holes. In some embodiments, the knob is configured to rotate in a third direction perpendicular to the first direction and the second direction, wherein rotating the knob is configured to at least one of tighten and loosen the knob.

The top bracket may comprise a top cap coupled on the first end of the elongate pole and an extension bar configured to couple the top cap to the top hook. The extension bar may comprise at least one height adjustment hole, and the extension bar may be configured to at least one of raise and lower a height of the top hook. In some embodiments, the bottom bracket comprises a bottom cap coupled on the second end of the elongate pole and an adjustable strap configured to couple the bottom cap to the bottom hook, wherein the adjustable strap is configured to at least one of tighten and loosen.

The disclosure includes a light therapy device mounting system comprising an elongate pole including a plurality of holes, the elongate pole comprising a first end and a second end, a first mounting device slidably coupled to the elongate pole via at least one hole of the plurality of holes, and a bottom base configured to receive the second end of the elongate pole. In some embodiments, the system further comprises a mobile stand comprising a plurality of wheels located on a bottom surface of the mobile stand, wherein the bottom base is configured to couple to a top surface of the mobile stand via a plurality of holes located on the top surface configured to receive at least one coupling mechanism, wherein the top surface is located opposite the bottom surface.

The light therapy device mounting system may further comprise a fixed stand configured to contact a ground surface and comprising a plurality of holes configured to receive at least one coupling mechanism, wherein the bottom base is configured to couple to a top surface of the fixed stand via the at least one coupling mechanism, and a wall bracket snapably coupled to the elongate pole, wherein the wall bracket comprises a plurality of holes configured to receive at least one coupling mechanism to thereby couple the wall bracket to a wall surface. In some embodiments, the fixed stand comprises a plurality of feet located on a bottom surface of the fixed stand, the plurality of feet configured to contact the ground surface, wherein the bottom surface is located opposite the top surface of the fixed stand. The wall bracket may comprise a C-shaped hook located on a first surface of the wall bracket, the C-shaped hook configured to snapably couple to the elongate pole. In some embodiments, the plurality of holes are located on a second surface of the wall bracket opposite the first surface, such that when the wall bracket is snapably coupled to the elongate pole and the wall bracket is coupled to the wall surface via the at least one coupling mechanism, the elongate pole is thereby coupled to the wall surface via the wall bracket.

The mobile stand may be configured to couple to a first bottom base via the plurality of holes located on the top surface of the mobile stand configured to receive the at least one coupling mechanism, wherein the first bottom base is configured to receive a first elongate pole, thereby coupling the first elongate pole to the mobile stand. In some embodiments, the mobile stand is configured to couple to a first bottom base, a second bottom base, and a third bottom base via the plurality of holes located on the top surface of the mobile stand configured to receive the at least one coupling mechanism. The first bottom base may be configured to receive a first elongate pole, the second bottom base may be configured to receive a second elongate pole, and the third bottom base may be configured to receive a third elongate pole, thereby coupling the first elongate pole, the second elongate pole, and the third elongate pole to the mobile stand. The light therapy device mounting system may further comprise at least one brace configured to couple at least one of the first elongate pole, the second elongate pole, and the third elongate pole to at least one adjacent pole.

In some embodiments, the elongate pole comprises a first elongate pole, and the system further comprises a second mounting device slidably coupled to one of the first elongate pole and a second elongate pole, wherein the system is sized and configured to accommodate a plurality of light therapy devices.

The disclosure includes a light therapy device floor stand comprising a floor plate extending along a first direction and a second direction, wherein the second direction is perpendicular to the first direction, a first curved side arm coupled to a top surface of the floor plate wherein the first curved side arm extends along a third direction that is perpendicular to both the first direction and the second direction, wherein the first curved side arm is coupled to a first side of the floor plate, and a second curved side arm coupled to the top surface of the floor plate and coupled to a second side located opposite the first side, the second curved side arm facing the first curved side arm such that the first curved side arm and the second curved side arm open toward one another. In some embodiments, the first curved side arm and the second curved side arm are configured to slidably receive a bottom portion of a light therapy device.

In some embodiments, the top surface of the floor plate comprises an indented portion arranged and configured to receive at least one of a portion of the first curved side arm, a portion of the second curved side arm, and the bottom portion of the light therapy device. The first curved side arm and the second curved side arm may be configured to couple to the floor plate in the indented portion.

The disclosure includes a light therapy device mounting system comprising an elongate pole including a plurality of holes, the elongate pole comprising a first portion, a second portion, and a coupler configured to couple the first portion and the second portion; a slider mount slidably coupled to the elongate pole via at least one hole of the plurality of holes; a top bracket slidably coupled to the first portion of the elongate pole, wherein the top bracket comprises a top hook for receiving a top portion of a door; and a bottom bracket slidably coupled to the second portion of the elongate pole, wherein the bottom bracket comprises a bottom hook for receiving a bottom portion of the door.

The light therapy device mounting system may further comprise a light therapy device detachably coupled to the slider mount, wherein the light therapy device may comprise a light therapy device bracket coupled to a back side of the light therapy device, the light therapy device bracket including a plurality of keyhole brackets configured to receive at least one mounting key coupled to the slider mount. In some embodiments, the slider mount comprises a hollow cylinder configured to slidably receive the elongate pole; a first cap node coupled to a first end of the hollow cylinder; a second cap node coupled to a second end of the hollow cylinder, wherein the second end is located opposite the first end; and a slider mount bracket coupled to the hollow cylinder, wherein the slider mount bracket is configured to detachably couple to the light therapy device via the plurality of keyhole brackets of the light therapy device bracket located on the back side of the light therapy device. The slider mount may also include a quick-release lever coupled to the hollow cylinder and the slider mount bracket, wherein the quick-release lever is located on a top portion of the slider mount bracket and is configured to retain the light therapy device bracket to the slider mount bracket, and an adjustment knob coupled to a side portion of the hollow cylinder. The adjustment knob may comprise a protrusion that extends into an inner portion of the hollow cylinder, and the protrusion may be configured to couple to at least one hole of the plurality of holes located on the elongate pole.

In some embodiments, the elongate pole is elongate in a first direction and the adjustment knob is configured to slide in a second direction perpendicular to the first direction, wherein sliding the adjustment knob in the second direction is configured to at least one of release and couple the protrusion to at least one hole of the plurality of holes. The adjustment knob may be configured to rotate in a third direction perpendicular to the first direction and the second direction, wherein rotating the adjustment knob may be configured to at least one of tighten and loosen the adjustment knob. In some embodiments, the quick release lever is configured to move along the third direction to at least one of retain and release the light therapy device bracket.

The first portion of the elongate pole may comprise a first top end and a first bottom end located opposite the first top end, and the second portion of the elongate pole may comprise a second top end and a second bottom end located opposite the second top end. In some embodiments, the first bottom end of the first portion and the second top end of the second portion are configured to receive the coupler, thereby coupling the first portion to the second portion.

The top bracket may comprise a top cap coupled on the first top end of the first portion of the elongate pole, an extension bar configured to couple the top cap to the top hook, and a top cover configured to at least partially conceal the top cap. In some embodiments, the extension bar comprises at least one height adjustment hole and is configured to at least one of raise and lower a height of the top hook. The extension bar may comprise a first extension bar defining a first length. In some embodiments, the system also includes a second extension bar defining a second length, wherein the second length is greater than the first length, and wherein the first extension bar and the second extension bar are configured to interchangeably couple to the top bracket. The bottom bracket may comprise a bottom cap coupled on the second bottom end of the second portion of the elongate pole, an adjustable strap configured to couple the bottom cap to the bottom hook, and a top cover configured to at least partially conceal the top cap, wherein the adjustable strap may be configured to at least one of tighten and loosen. In some embodiments, the system further comprises a first protective pad coupled to the top bracket and a second protective pad coupled to the bottom bracket, wherein the first protective pad and the second protective pad are configured to protect a surface of the door.

In some embodiments, the top hook comprises a first top hook defining a first depth and the bottom hook comprises a first bottom hook defining the first depth, the system further comprising a second top hook defining a second depth and a second bottom hook defining the second depth, wherein the first depth is less than the second depth. The first depth may be sized to correspond to a first door depth and the second depth may be sized to correspond to a second door depth. In some embodiments, the top bracket is configured to interchangeably couple to the first top hook and the second top hook, and the bottom bracket is configured to interchangeably couple to the first bottom hook and the second bottom hook.

The slider mount may comprise a first slider mount and the light therapy device may comprise a first light therapy device. In some embodiments, the system further comprises a second slider mount slidably coupled to the elongate pole and a second light therapy device detachably coupled to the second slider mount.

The disclosure includes a light therapy device mounting system comprising an elongate pole comprising a plurality of holes, the elongate pole comprising a first portion, a second portion, and a coupler configured to couple the first portion and the second portion; a slider mount slidably coupled to the elongate pole via at least one hole of the plurality of holes, and a boot bracket configured to receive a bottom end of the second portion of the elongate pole. In some embodiments, the boot bracket is configured to couple to one of a fixed stand and a mobile stand. The fixed stand may comprise a plurality of feet configured to contact a ground surface, and the mobile stand may comprise a plurality of wheels configured to contact the ground surface.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments. For ease of viewing the figures, not all features may be labeled in each drawing.

DETAILED DESCRIPTION

Figure 1:
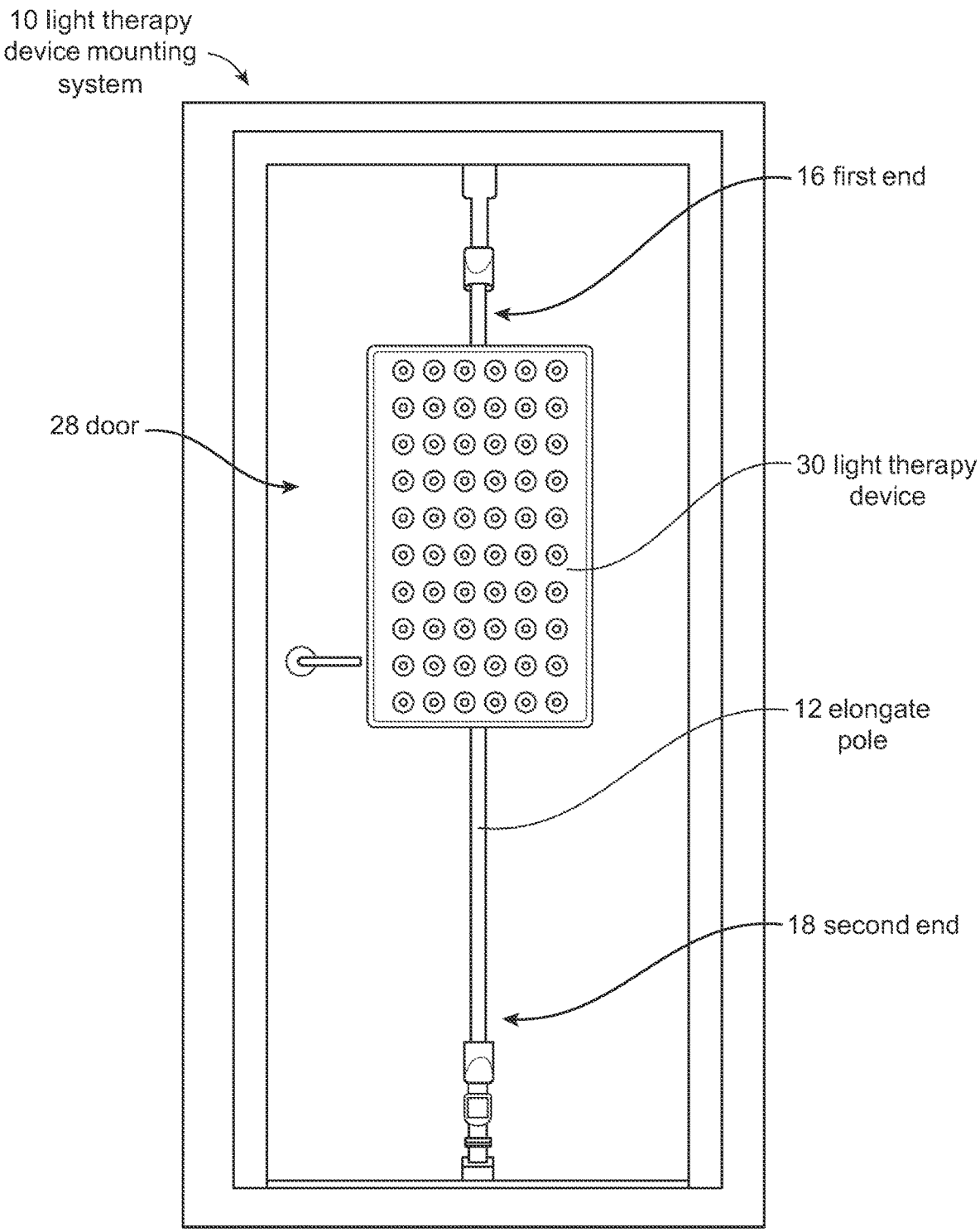
FIG. 1 illustrates a front view of a light therapy device mounting system coupled to a door, according to some embodiments.

Although certain embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. Additionally, the structures, systems, and/or devices described herein may be embodied as integrated components or as separate components.

For purposes of comparing various embodiments, certain aspects and advantages of these embodiments are described. All such aspects or advantages are not necessarily achieved by any particular embodiment. For example, various embodiments may be carried out in a manner that achieves or optimizes one advantage or group of advantages as taught herein without necessarily achieving other aspects or advantages as may also be taught or suggested herein.

Introduction

An objective of the present invention is to provide a variety of accessories to support (e.g., hang, mount, hold in an upright position, etc.) at least one light therapy device. Of the embodiments described herein are different components, some of which may be used interchangeably with other components. For example, the elongate pole may be used with a mobile stand, a fixed stand, a door mounting system, and/or a wall mounting system. A single light therapy device or multiple light therapy devices may be supported by any of the accessory devices/systems described herein.

LIST OF REFERENCE NUMERALS

10—light therapy device mounting system
12—elongate pole
14—plurality of holes
16—first end
18—second end
20—mounting device
22a—top bracket
22b—bottom bracket
24a—top hook
24b—bottom hook
26a—top portion (of door)
26b—bottom portion (of door)
28—door
30—light therapy device
30a—plurality of light therapy devices
32—light therapy device bracket
34—back side (of light therapy device)
36—plurality of keyhole brackets
37—at least one projection
38—hollow cylinder
40—mounting device bracket
42—clip
44—top portion (of mounting device bracket)
46—knob
48—protrusion
50—inner portion (of hollow cylinder)
52a—top cap
52b—bottom cap
54—extension bar
56—adjustable strap
58—bottom base
60—mobile stand 62—plurality of wheels
64a—bottom surface (mobile stand)
64b—bottom surface (fixed stand)
66a—top surface (mobile stand)
66b—top surface (fixed stand)
68a—plurality of holes (mobile stand)
68b—plurality of holes (fixed stand)
70—at least one coupling mechanism
72—fixed stand
74—ground surface
76—wall bracket
78—plurality of holes (wall bracket)
80—wall surface
82—plurality of feet
84—C-shaped hook
86a—first surface (wall bracket)
86b—second surface (wall bracket)
88—at least one brace
90—light therapy device floor stand
92—floor plate
94a—first curved side arm
94b—second curved side arm
96—top surface
98a—first side (floor plate)
98b—second side (floor plate)
100—bottom portion (light therapy device)
102—light therapy device
104—light therapy device table stand
106—back side
108—light therapy device
110—base
112—arm
114—back bracket
116—elongate pole
116a—first portion
116b—second portion
116c—coupler
118—plurality of holes
120a—first protective pad
120b—second protective pad
122a—top cover
122b—bottom cover
124—slider mount
126—quick-release lever
128a—first cap node
128b—second cap node
130—adjustment knob
132—slider mount bracket
134—at least one mounting key
136—boot bracket
138—light therapy device mounting system
140a—first top end (first portion of elongate pole)
140b—first bottom end (first portion of elongate pole)
142a—second top end (second portion of elongate pole)
142b—second bottom end (second portion of elongate pole)

Door Mount System Embodiments

FIG. 1 illustrates an embodiment of a light therapy device mounting system 10. As shown in the Figure, the system 10 may be configured to couple to a door 28. In many embodiments, the system 10 includes an elongate pole 12 comprising a first end 16 and a second end 18. The first end 16 may be considered the "top" (or adjacent the top) of the elongate pole 12, and the second end 18 may be considered the "bottom" (or adjacent the bottom) of the elongate pole 12. A light therapy device 30 may be configured to couple to the elongate pole 12 between the first end 16 and the second end 18. The manner in which the light therapy device 30 couples to the elongate pole 12 will be discussed in greater detail later in the disclosure. Though a single light therapy device 30 is shown coupled to the elongate pole 12, multiple light therapy devices may couple to the elongate pole 12. In some embodiments, the light therapy device 30 comprises a larger device 30 than depicted in FIG. 1. The light therapy device 30 may comprise a smaller device 30 than depicted in FIG. 1. The system 10 may be configured to include a plurality of elongate poles 12 coupled to the door 28, and each elongate pole 12 may be configured to couple to at least one light therapy device 30.

Figure 2:
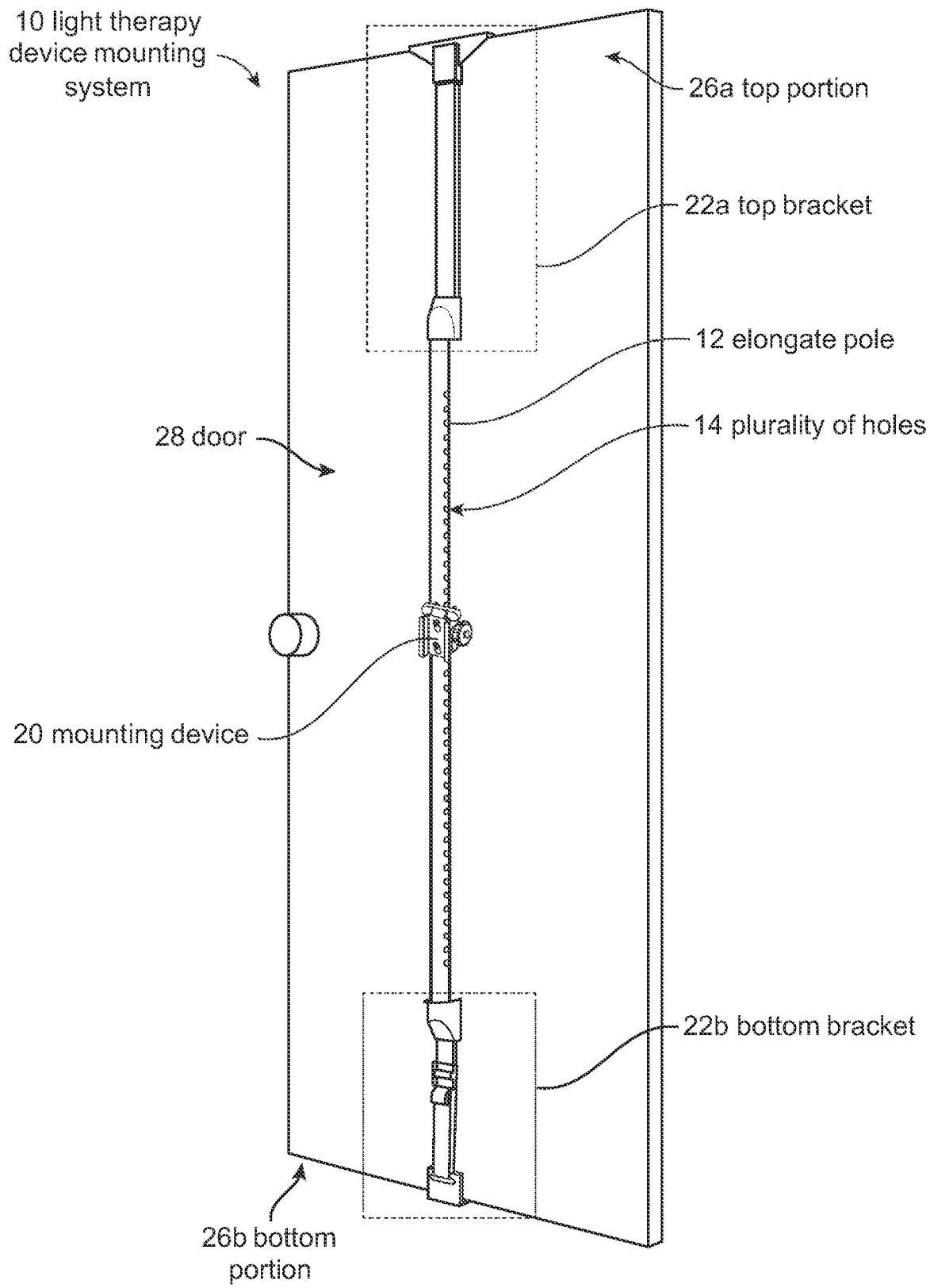
FIG. 2 illustrates a perspective view of a light therapy device mounting system coupled to a door, according to some embodiments.

FIG. 2 illustrates a perspective view of the system 10 coupled to the door 28. FIG. 2 is similar to FIG. 1, but shows the system 10 without the light therapy device 30 and illustrates additional elements of the system 10. For example, FIG. 2 includes the mounting device 20, which will be discussed in greater detail later in the disclosure, in particular with reference to FIGS. 5 and 6. FIG. 2 also demonstrates that, in many embodiments, the elongate pole 12 comprises a plurality of holes 14. The plurality of holes 14 may extend in a substantially straight line down a side portion of the pole 12, as illustrated in FIG. 2. The plurality of holes 14 may extend down substantially the full length of the pole 12. As shown in FIG. 2, the plurality of holes 14 may extend down less than the full length of the pole 12. In some embodiments, the plurality of holes 14 comprises more than one line of holes. The plurality of holes 14 may be featured in a scattered pattern around the pole 12. The plurality of holes 14 may be located anywhere on the surface of the pole 12. In some embodiments, the plurality of holes 14 is configured to accommodate height adjustment of the placement of the mounting device 20, and thereby, of a light therapy device 30 coupled to the mounting device 20.

FIG. 2 also includes a top bracket 22a and a bottom bracket 22b. In many embodiments, the top bracket 22a is coupled to the first end 16 of the elongate pole 12, and the bottom bracket 22b is coupled to the second end 18 of the elongate pole 12. The brackets 22a, 22b may be slidably coupled to the elongate pole 12 at their respective ends 16, 18, wherein the brackets 22a, 22b may be configured to slidably receive the ends 16, 18. In some embodiments, the brackets 22a, 22b are coupled in a different manner (e.g., snapably, mechanically, threadably, via a friction fit, via a mechanism such as a screw or locking pin, via the plurality of holes 14, and the like). The brackets 22a, 22b may be detachably coupled to the elongate pole 12. The top bracket 22a may also be configured to detachably couple to a top portion 26a of the door 28, and the bottom bracket 22b may be configured to detachably couple to a bottom portion 26b of the door 28.

Figure 3A:
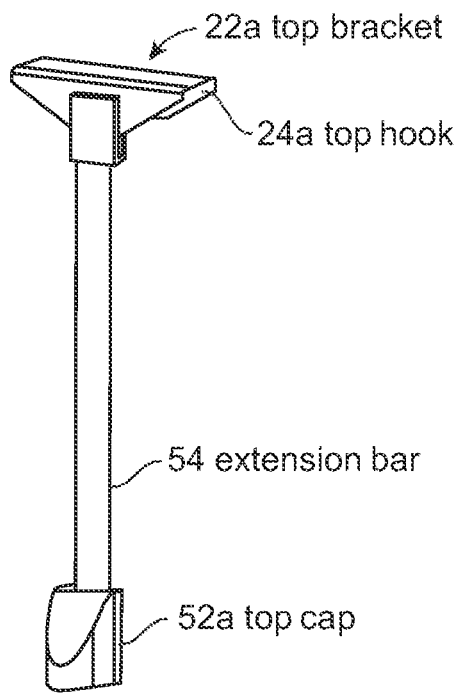
FIGS. 3A and 3B illustrate front and back views, respectively, of a top bracket, according to some embodiments.
Figure 3B:
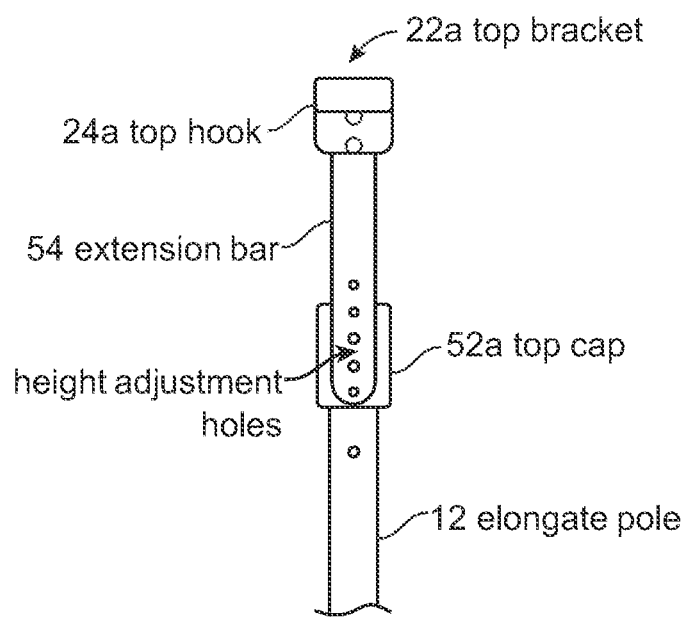

The top bracket 22a is shown in greater detail in FIGS. 3A and 3B, which show front and back views, respectively, of an embodiment of the top bracket 22a. In many embodiments, the top bracket 22a comprises a top cap 52a, a top hook 24a, and an extension bar 54. As previously stated, the top bracket 22a may be slidably coupled to a first end 16 of the elongate pole 12. In some embodiments, the top bracket 22a is slidably coupled via the top cap 52a, which is configured to receive the elongate pole 12. The top cap 52a may include two pieces configured to snap together around the elongate pole 12. In some embodiments, one-piece (e.g., a back piece) of the top cap 52a is configured to receive the elongate pole 12, and the second piece (e.g., a front piece) is configured to cover the first end 16 and the first piece of the cap 52a, thus providing a cosmetic appearance to the top cap 52a. In some embodiments, the top cap 52a comprises a single piece configured to substantially surround the first end 16 of the elongate pole 12. The top cap 52a may comprise more than two pieces.

In some embodiments, the top cap 52a is configured to couple to the extension bar 54. As shown in FIG. 3B, the extension bar 54 may include at least one height adjustment hole. In many embodiments, the at least one height adjustment hole is configured to couple to the top cap 52a via at least one coupling mechanism, such as a bolt. The at least one coupling mechanism may be located on a back portion of the top cap 52a, where a back portion may be considered a portion opposite a portion of the system 10 coupled to the light therapy device 30. For example, in the embodiment shown in FIG. 1, the system 10 is configured such that the light therapy device 30 faces away from the door 28. In such an embodiment, the back portion of the top cap 52a may be considered the portion located adjacent the door 28. In some embodiments, the at least one height adjustment hole and the at least one coupling mechanism are located within the top cap 52a. The at least one height adjustment hole and the at least one coupling mechanism may be located on a front portion located opposite the back portion of the top cap 52a.

The at least one height adjustment hole may be configured to receive the at least one coupling mechanism such that if the top height adjustment hole receives the at least one coupling mechanism, the extension bar 54 is configured to sit at a minimum height. If the bottom height adjustment hole receives the at least one coupling mechanism, the extension bar 54 may be configured to sit at a maximum height. In many embodiments, the extension bar 54 is configured to accommodate a range of door heights by raising or lowering the height of the top hook 24a. The extension bar 54 may be configured to accommodate door heights of about 80 inches. The extension bar 54 may be configured to accommodate doors shorter than 80 inches. In some embodiments, the extension bar 54 is configured to accommodate doors taller than 80 inches. Embodiments of the extension bar 54 may define different lengths in order to accommodate different door heights. For example, in some embodiments, the extension bar 54 measures about 9.5 inches long, which may be used for a door about 80 inches tall. The extension bar 54 may measure about 25 inches long, which may be used for a door taller than 80 inches. The extension bar 54 may measure any length between about 9.5 inches and about 25 inches in length. The extension bar 54 may measure shorter than 9.5 inches, which may be used for a door shorter than 80 inches. In some embodiments, the extension bar 54 measures longer than 25 inches. Such embodiments may enable the system 10 to couple to an oversize door significantly taller than 80 inches.

As shown in FIG. 2, the top hook 24a may be configured to receive a top portion 26a of the door 28. The top hook 24a may define a range of widths, as demonstrated by FIGS. 3A and 3B. In many embodiments, the top hook 24a is configured to receive the top portion 26a of the door 28 such that the top hook 24a extends across a top edge of the door 28 and at least partially down a side of the door 28 located opposite the side of the door 28 adjacent the light therapy device 30. For example, if the light therapy device 30 is coupled to a side of the door 28 facing into a room when the door 28 is in a closed position, the top hook 24a may extend at least partially down the side of the door 28 facing out into a hallway. In many embodiments, the top hook 24a is sized and configured to not impede operation of the door 28, such that the door 28 may be moved between an open position and a closed position (and vice versa) when the system 10, including the top hook 24a, is coupled to the door 28. The top hook 24a may be sized and configured to produce minimal contact with a door jamb when the door 28 is in the closed position. For example, the top hook 24a may define a thickness of a few millimeters where "thickness" is defined as the amount of the top hook 24a that sits on top of the top edge of the door 28, between the top edge and the doorjamb.

The top hook 24a may be coupled to the extension bar 54 in a number of suitable ways, including but not limited to, slidably coupled, mechanically detachably coupled via a mechanism such as a bolt, screw, etc., and coupled via welding, adhesive, and the like. In some embodiments, the top hook 24a is fixedly coupled to the extension bar 54 via a plurality of fasteners with locking nuts. The fasteners may comprise 4 mm fasteners. In some embodiments, the extension bar 54 is coupled to a back portion of the top hook 24a located adjacent the door 28. The extension bar 54 may be coupled to a front portion of the top hook 24a, where the front portion is located opposite the back portion.

Figure 4A:
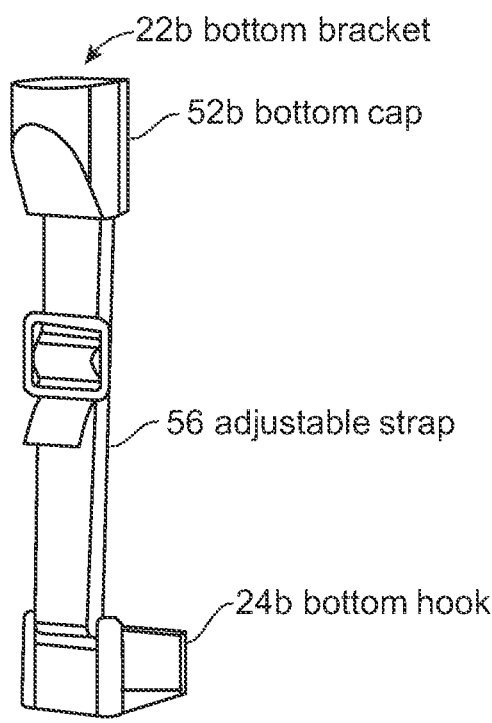
FIGS. 4A and 4B illustrate front and back views, respectively, of a bottom bracket, according to some embodiments.
Figure 4B:
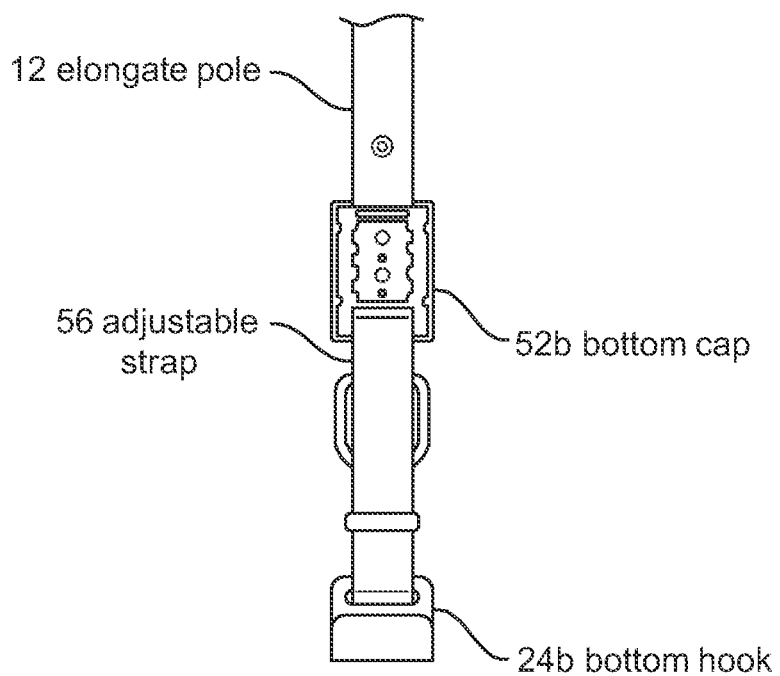

FIGS. 4A and 4B are similar to FIGS. 3A and 3B; however, they illustrate the bottom bracket 22b rather than the top bracket 22a. As shown, in many embodiments, the bottom bracket 22b includes a bottom cap 52b, and adjustable strap 56, and a bottom hook 24b. The bottom cap 52b may be configured to slidably couple the bottom bracket 22b to the second end 18 of the elongate pole 12. In some embodiments, the bottom cap 52b is configured to slidably receive the elongate pole 12. The bottom cap 52b may include two pieces configured to snap together around the elongate pole 12. In some embodiments, one-piece (e.g., a back piece) of the bottom cap 52b is configured to receive the elongate pole 12, and the second piece (e.g., a front piece) is configured to cover the second end 18 and the first piece of the cap 52b, thus providing a cosmetic appearance to the bottom cap 52b. In some embodiments, the bottom cap 52b comprises a single piece configured to substantially surround the second end 18 of the elongate pole 12. The bottom cap 52b may comprise more than two pieces. The bottom cap 52b may be configured to store the excess length of the adjustable strap 56 after the strap 56 is tightened and/or loosened.

In some embodiments, the bottom cap 52b is configured to couple to the adjustable strap 56. The adjustable strap 56 may loop around a portion of the bottom cap 52b. In some embodiments, the portion comprises at least one of a back piece, a front piece, and an internal piece of the bottom cap 52b. The portion may comprise a horizontal bar or similar portion. The adjustable strap 56 may couple to the bottom cap 52b in any other suitable way. In many embodiments, the adjustable strap 56 comprises a flexible strap and an adjusting mechanism. The adjusting mechanism may comprise a strap adjuster, a buckle, a slider, a cord lock, or any similar adjusting mechanism. In some embodiments, the adjusting mechanism is configured to at least one of tighten and loosen the adjustable strap 56. Tightening the adjustable strap 56 may facilitate tightening the system 10 by increasing the tension between the bottom hook 24b and the bottom cap 52b, and, therefore, between the bottom hook 24b and the elongate pole 12. Tightening the system 10 may be desirable in order to reduce the amount of movement of the system 10 on the door 28, particularly when the door 28 is moved between a closed position and an open position, and vice versa. Loosening the adjustable strap 56 may reduce the tension between the bottom hook 24b and the bottom cap 52b, and, therefore, between the bottom hook 24b and the elongate pole 12, thereby facilitating loosening of the system 10 so that the system 10 may be removed from and/or adjusted on the door 28. In some embodiments, the system 10 is arranged such that the top hook 24a is configured to couple to the door 28, then the bottom hook 24b is configured to couple to the door 28, then the adjustable strap 56 is configured to tighten.

As shown in FIG. 2, the bottom hook 24b may be configured to receive a bottom portion 26b of the door 28. In some embodiments, the bottom hook 24b defines a different width than the top hook 24a. The bottom hook 24b may define substantially the same width as at least one embodiment of the top hook 24a. In many embodiments, the bottom hook 24b is configured to receive the bottom portion 26b of the door 28 such that the bottom hook 24b extends across a bottom edge of the door 28 and at least partially up a side of the door 28 located opposite the side of the door 28 including the light therapy device 30. For example, if the light therapy device 30 is coupled to a side of the door 28 facing into a room when the door 28 is in a closed position, the bottom hook 24b may extend at least partially up the side of the door 28 facing out into a hallway. The bottom hook 24b may extend up the opposite side of the door 28 substantially the same amount as the top hook 24a extends down the opposite side of the door 28. The top hook 24a and bottom hook 24a may extend different amounts down and up, respectively, the opposite side of the door 28.

In many embodiments, the bottom hook 24b is sized and configured to not impede operation of the door 28, such that the door 28 may be moved between an open position and a closed position (and vice versa) when the system 10, including the bottom hook 24b, is coupled to the door 28. The bottom hook 24b may be sized and configured to produce minimal contact with a floor surface. For example, the bottom hook 24b may define a thickness of a few millimeters where "thickness" is defined as the amount of the bottom hook 24b that sits under the bottom edge of the door 28, between the bottom edge and the floor surface. In many embodiments, the top hook 24a and the bottom hook 24b define substantially the same thickness. The top hook 24a and the bottom hook 24b may define different thicknesses.

In some embodiments, the adjustable strap 56 is configured to couple to the bottom hook 24b by looping around a portion of the hook 24b, as shown in FIGS. 4A and 4B. The adjustable strap 56 may couple to the bottom hook 24b in other ways, including fixed coupling. In some embodiments, the adjustable strap 56 is fixedly coupled to the bottom hook 24b and movably coupled to the bottom cap 52b. The adjustable strap 56 may be movably coupled to the bottom hook 24b and fixedly coupled to the bottom cap 52b. The adjustable strap 56 may be movably coupled to both the bottom cap 52b and the bottom hook 24b. The adjustable strap 56 may be fixedly coupled to both the bottom cap 52b and the bottom hook 24b.

In many embodiments, at least one of the top hook 24a and the bottom hook 24b is sized and configured to fit a standard door depth. An example of a standard door depth is about 1.375 inches. As such, in some embodiments, at least one of the top hook 24a and the bottom hook 24b defines a depth of about 1.375 inches. At least one of the top hook 24a and the bottom hook 24b may be sized slightly larger than a standard door depth to accommodate deeper doors. In some embodiments, at least one of the top hook 24a and the bottom hook 24b defines a depth of about 1.875 inches. At least one of the top hook 24a and the bottom hook 24b may define a depth of greater than 1.875 inches. At least one of the top hook 24a and the bottom hook 24b may define a depth of less than 1.375 inches. In many embodiments, the top hook 24a and the bottom hook 24b define substantially the same depth. The top hook 24a and the bottom hook 24b may define different depths.

Figure 5:
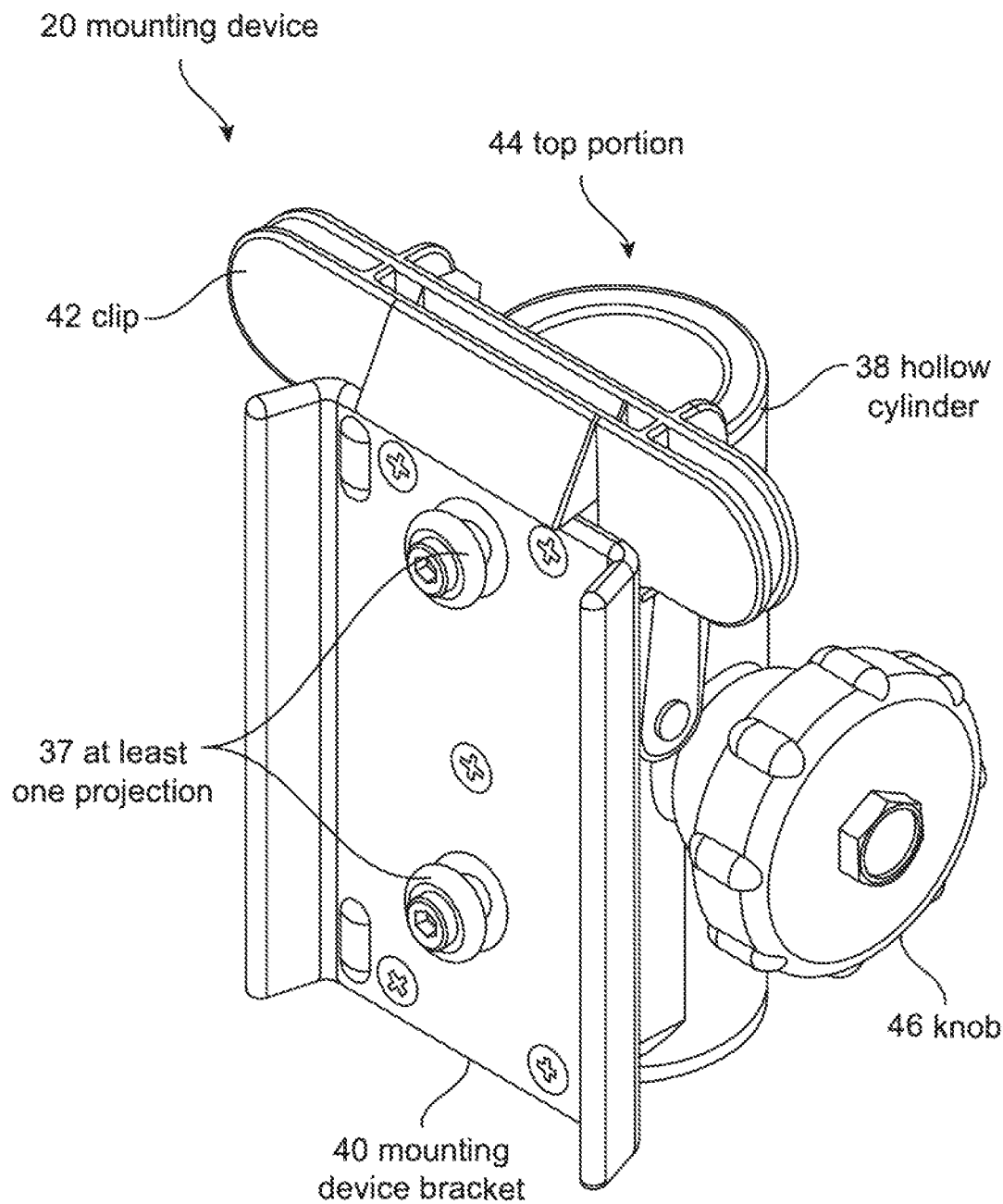
FIG. 5 illustrates a perspective view of a mounting device, according to some embodiments.

FIG. 5 shows a perspective view of a mounting device 20. In many embodiments, the mounting device 20 includes a hollow cylinder 38, a mounting device bracket 40, a clip 42, and a knob 46. The mounting device 20 may also include at least one projection 37 coupled to a front-facing surface of the mounting device bracket 40, which will be discussed in greater detail with reference to FIG. 7. In some embodiments, the clip 42 is located at a top portion 44 of the mounting device 20. The clip 42 may be located at a bottom portion opposite the top portion. The knob 46 may be coupled to a side portion of the hollow cylinder 38. The mounting device bracket 40 may be configured to couple to the at least one of the clip 42 and the hollow cylinder 38 via any of the coupling mechanisms disclosed herein.

The hollow cylinder 38 may be configured to slidably receive the elongate pole 12, as demonstrated in FIG. 2. At least one of a top end and a bottom end of the hollow cylinder 38 may comprise a collar configured to at least one of substantially surround and cover a top edge and bottom edge, respectively, of the cylinder 38. In many embodiments, the mounting device 20 is configured to couple to the elongate pole 12 via at least one hole of the plurality of holes 14, shown in FIG. 2. It should be noted that FIG. 2 shows the mounting device 20 without the mounting device bracket 40 or the clip 42.

Figure 6:
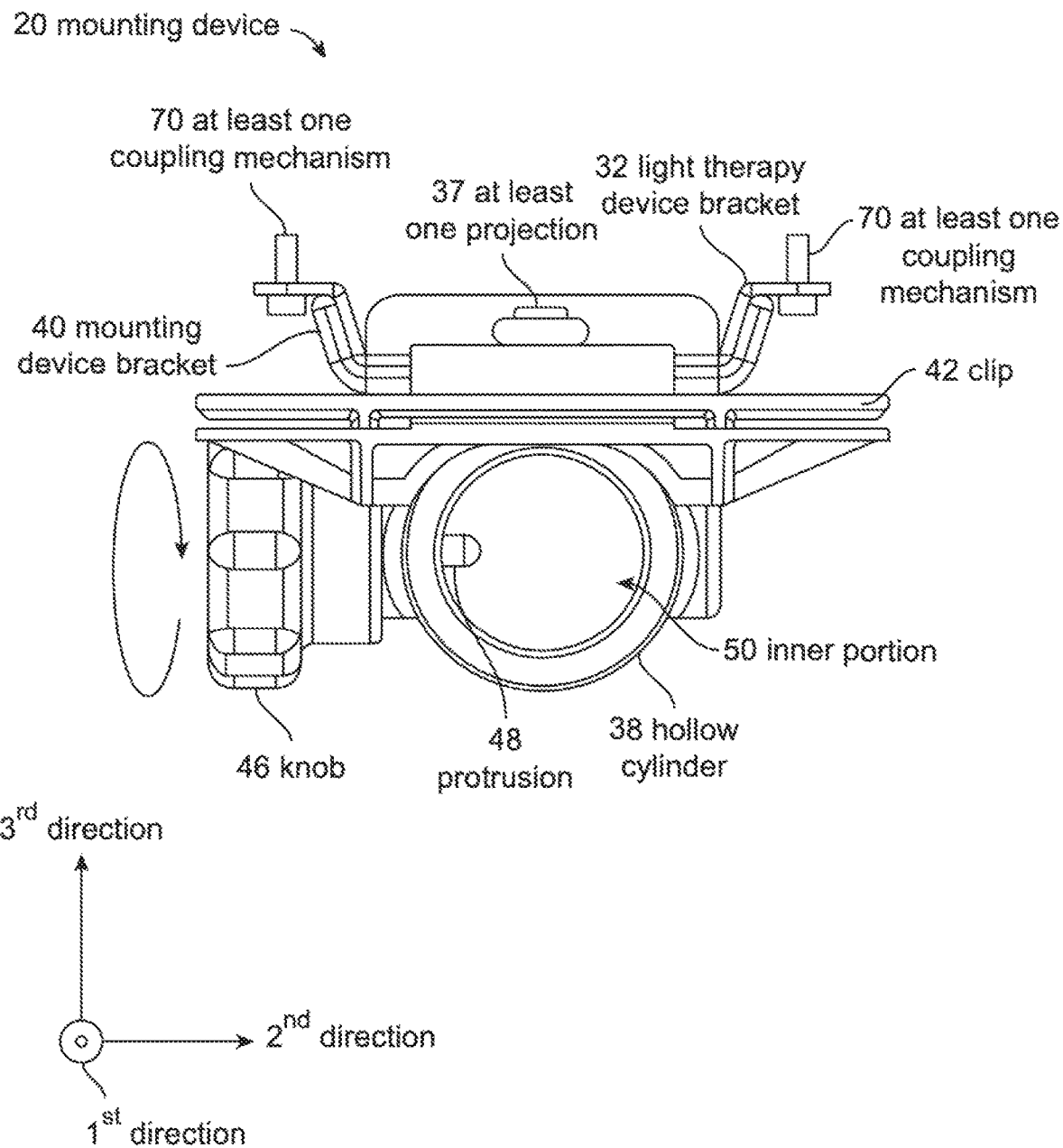
FIG. 6 illustrates a top view of a mounting device, according to some embodiments.

FIG. 6 shows a top view of the mounting device 20 and includes the light therapy device bracket 32, which will be discussed further with reference to FIGS. 7 and 8. In many embodiments, the elongate pole 12 (not shown in FIG. 6) extends along a first direction. The knob 46 may be configured to slide along a second direction, where the second direction may be perpendicular to the first direction, as shown by the directional indicators included in FIG. 6. In many embodiments, when the knob 46 slides along the second direction, a protrusion 48 coupled to the knob 46 at least one of extends into and retracts from an inner portion 50 of the hollow cylinder 38. At least one hole of the plurality of holes 14 of the elongate pole 12 may be configured to receive the protrusion 48, thereby coupling the mounting device 20 to the elongate pole 12. Stated another way, the protrusion 48 may operate similarly to a locking pin. In some embodiments, the knob 46 is pulled along the second direction away from the hollow cylinder 38, thereby retracting the protrusion 48 and allowing the mounting device 20 to slide on the elongate pole 12 in the first direction. Once the mounting device 20 is in a desired location (i.e., at a desired height) on the elongate pole 12, the knob 46 may be pushed toward the hollow cylinder 38, thereby inserting the protrusion 48 into the inner portion 50 and coupling the protrusion 48 to at least one hole of the plurality of holes 14. The knob 46 may include a plurality of protrusions 48 configured to couple to the plurality of holes 14. The knob 46 may comprise a spring mechanism configured to enable retraction of the protrusion 48.

In many embodiments, the knob 46 is configured to rotate along a third direction, where the third direction is perpendicular to both the first direction and the second direction. Rotating the knob 46 may be configured to tighten and/or loosen the knob 46, thereby tightening and/or loosening the coupling between the hollow cylinder 38 and the elongate pole 12. For example, after coupling the mounting device 20 to the elongate pole 12 via the protrusion 48 and the plurality of holes 14, a user of the system 10 may desire to tighten the knob 46 in order to provide greater security to the location of the mounting device 20 on the pole 12. Prior to retracting the protrusion 48 to move the mounting device 20, the user may then rotate the knob 46 in order to loosen the knob 46 before sliding the knob 46 along the second direction.

Figure 7:
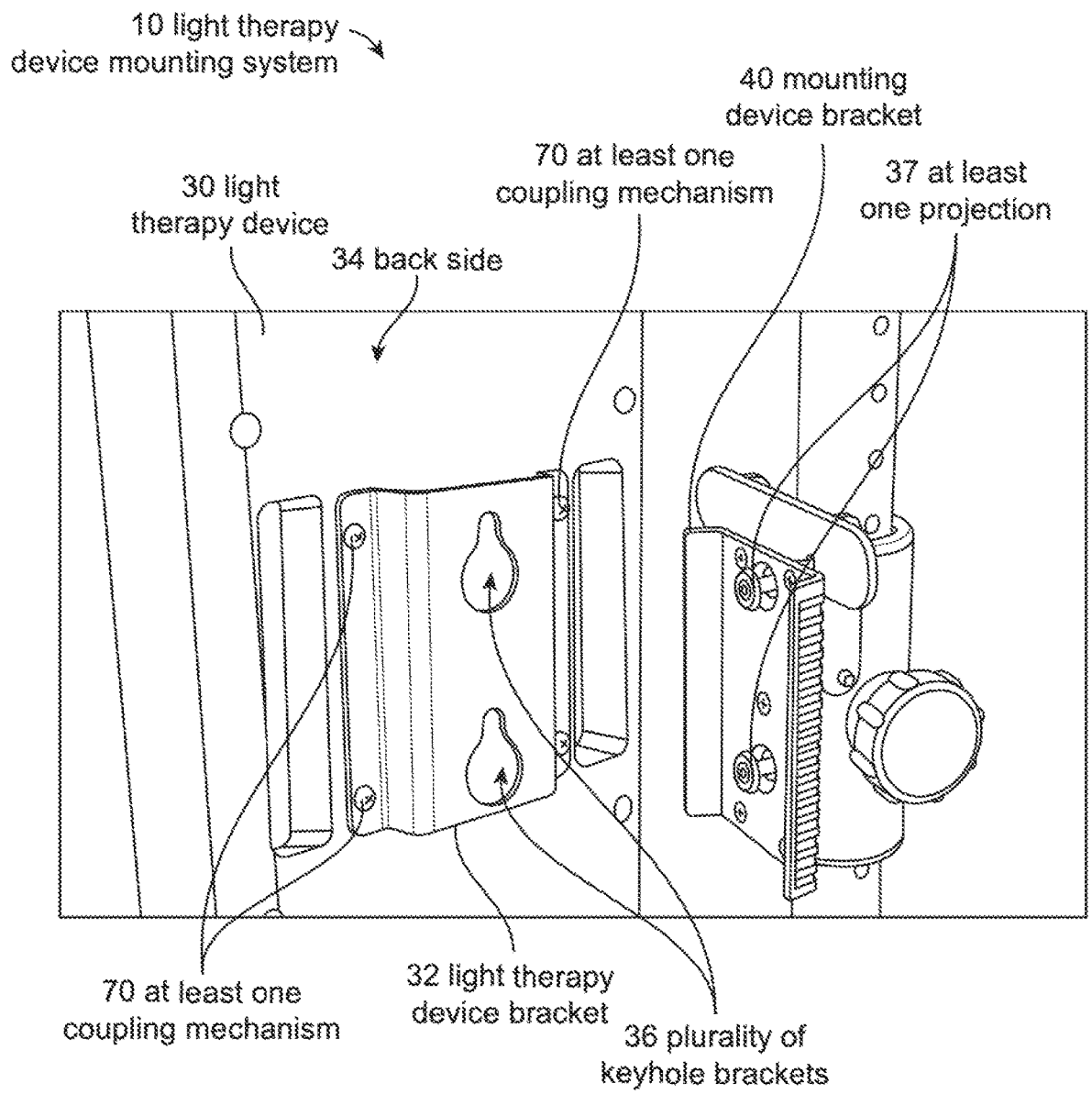
FIG. 7 illustrates a perspective view of a light therapy device mounting system, according to some embodiments.
Figure 8:
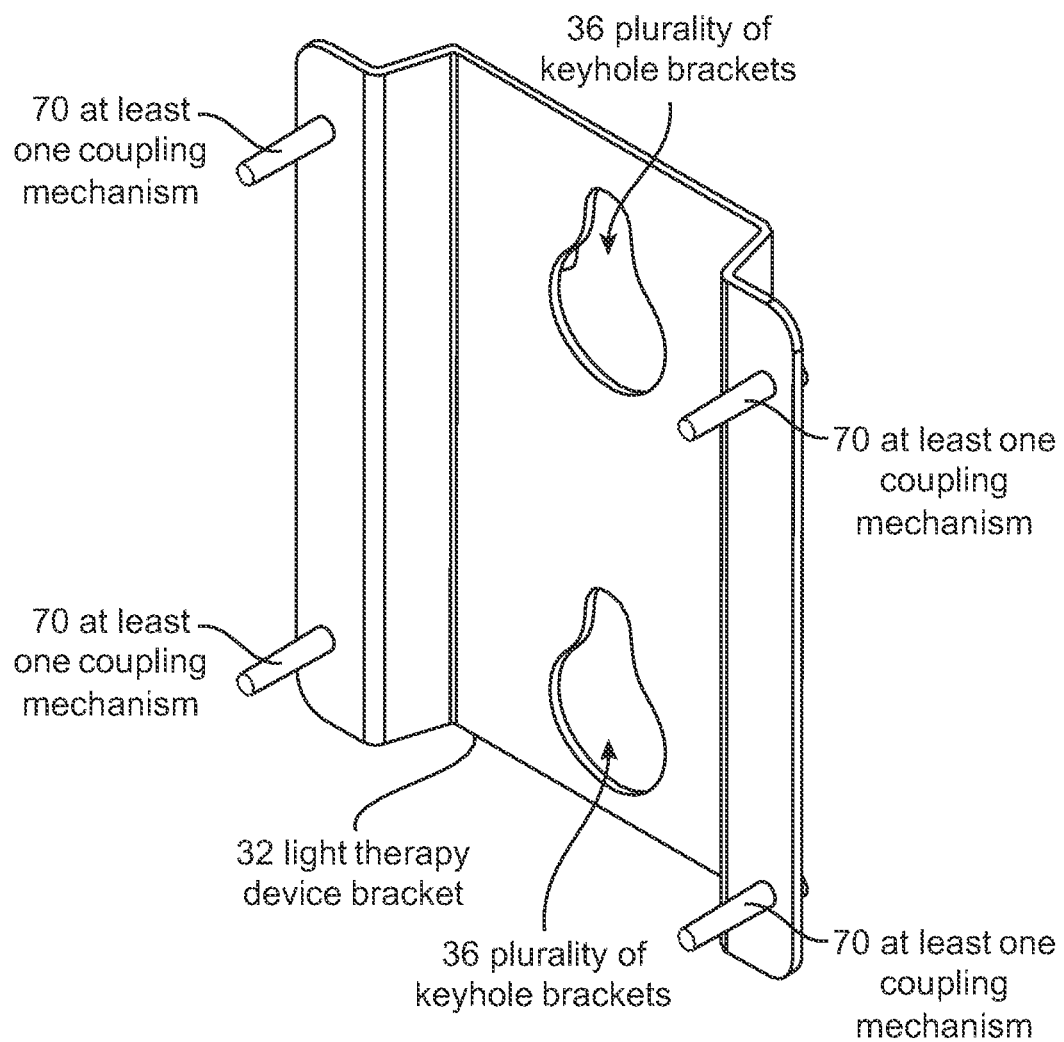
FIG. 8 illustrates a perspective view of a light therapy device bracket, according to some embodiments.

FIG. 7 shows a perspective view of the system 10, including a back side 34 of a light therapy device 30. As shown, in many embodiments, the light therapy device 30 includes a light therapy device bracket 32 located on the back side 34 of the light therapy device 30. The light therapy device bracket 32 may include a plurality of keyhole brackets 36 configured to detachably couple to the at least one projection 37, thereby detachably coupling the light therapy device bracket 32 to the mounting device bracket 40. In some embodiments, the at least one projection 37 is coupled to a front face of the mounting device bracket 40. The at least one projection 37 may be configured to extend through the bracket 40 to the front face from a back portion located adjacent the hollow cylinder 38. The at least one projection 37 may be coupled to the hollow cylinder 38. In some embodiments, the light therapy device bracket 32 is coupled to the back side 34 of the light therapy device 30 via at least one coupling mechanism 70. The at least one coupling mechanism 70 may include any suitable mechanism, including but not limited to, screw(s), bolt(s), staple(s), magnet(s), adhesive, welding, and the like. FIG. 8 shows a standalone view of the light therapy device bracket 32. Though shown in FIGS. 7 and 8 with four mechanisms in the at least one coupling mechanism 70, it should be noted that the bracket 32 may include fewer or more than four coupling mechanisms 70. The bracket 32 also may include a single keyhole bracket. In some embodiments, the plurality of keyhole brackets 36 comprises more than two keyhole brackets 36.

The clip 42 shown in FIGS. 5 and 6 may be configured to retain the light therapy device bracket 32 in a locked position on the mounting device bracket 40. In some embodiments, when the light therapy device bracket 32 is coupled to the mounting device bracket 40, a top edge of the light therapy device bracket 32 is configured to sit below the clip 42. As such, the clip 42 may move back toward the elongate pole 12 to allow the bracket 32 to slide onto the bracket 40, then may "spring" back into the original position, thereby retaining the bracket 32 on the bracket 40. The clip 42, and the extra security it provides, may enable the system 10 to withstand a sudden movement (e.g., person bumps into system 10, door 28 slammed into a wall, earthquake, and the like) and prevent the light therapy device 30 from being dislodged from the mounting device bracket 40. In many embodiments, the clip 42 is a spring-loaded clip. The clip 42 may be any suitable type of clip.

In many embodiments, to release the light therapy device 30, a user moves the clip 42 back toward the elongate pole 12 and raises the light therapy device bracket 32 (and light therapy device 30) up and off of the mounting device bracket 40. The movements of the clip 42 may be the inverse of what has been disclosed. For example, the clip 42 may move toward the light therapy device 30 in order to release and toward the elongate pole 12 in order to engage the light therapy device bracket 32. In some embodiments, the system 10 includes a plurality of clips 42 on the mounting device bracket 40.

Mobile Stand System Embodiments

Figure 9:
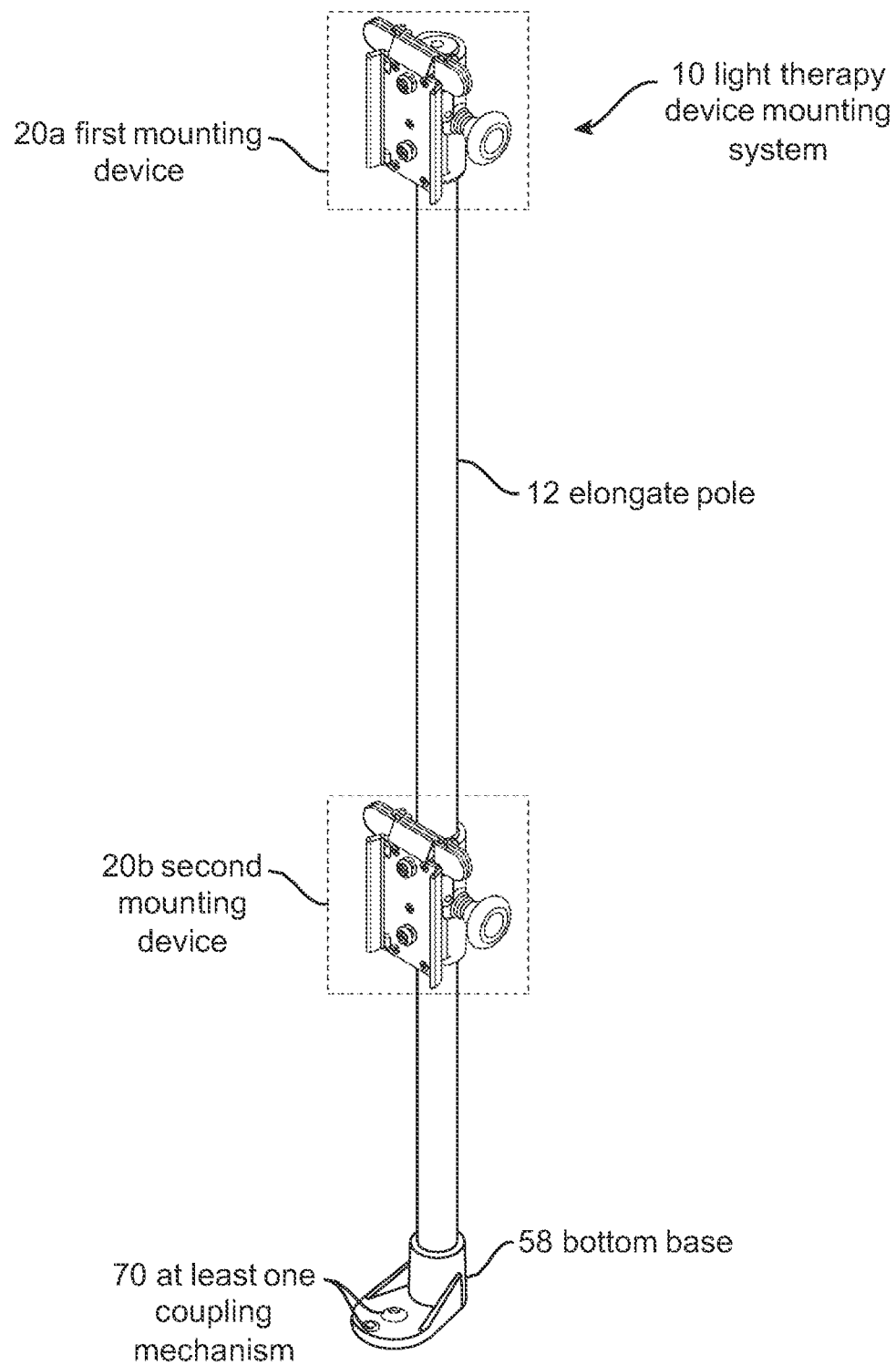
FIG. 9 illustrates a perspective view of a light therapy device mounting system, according to some embodiments.

FIG. 9 shows an embodiment of the light therapy device mounting system 10. Like the embodiments shown in FIGS. 1 and 2, the system 10 illustrated in FIG. 9 includes an elongate pole 12 and a mounting device 20. Though not shown in FIG. 9, the elongate pole 12 may include a plurality of holes 14, and the mounting device 20 may be configured to couple to the elongate pole 12 via at least one hole of the plurality of holes 14, as discussed with reference to FIG. 6. The elongate pole 12 may also comprise a first end 16 and a second end 18. In some embodiments, the system 10 includes a first mounting device 20a and a second mounting device 20b. The first mounting device 20a may be coupled to a light therapy device 30, and the second mounting device 20b may be coupled to another light therapy device 30. As such, multiple light therapy devices 30 may be coupled to the elongate pole 12 simultaneously.

FIG. 9 also illustrates that, in some embodiments, the system 10 includes a bottom base 58 coupled to the elongate pole 12. The bottom base 58 may be configured to slidably receive the elongate pole 12. Other methods of coupling, including, but not limited to, a friction fit, threadably coupling, coupling via gravity, and mechanical coupling may be suitable to couple the elongate pole 12 to the bottom base 58. The bottom base 58 may be configured to couple to the elongate pole 12 at the second end 18 (shown in FIG. 1) of the elongate pole 12. As illustrated, the bottom base 58 may be shaped similar to an elbow connector. The bottom base 58 may define any suitable shape to receive the elongate pole 12 and couple to a stand. In many embodiments, the bottom base 58 is configured to support the elongate pole 12 and any other elements (e.g., mounting device 20, light therapy device 30, and the like coupled to the elongate pole 12) in an upright position.

In some embodiments, the system 10 includes an additional element, not shown in the Figures, configured to facilitate coupling between the bottom base 58 and the elongate pole 12. The additional element may comprise a plug-type component configured to slidably couple to the bottom base 58. For example, the bottom base 58 may be configured to receive the plug and couple to the plug via at least one mechanical coupling mechanism. The elongate pole 12 may then be configured to slide into the bottom base 58 around the plug, such that when the elongate pole 12 is coupled to the bottom base 58, the plug is located at least partially within an interior portion of the elongate pole 12. The bottom base 58 and the plug may comprise at least one hole located on a bottom and/or back surface, wherein the at least one hole is configured to receive a screw, bolt, or similar device to mechanically couple the plug to the bottom base 58. The plug may be configured to provide additional support and stability to the elongate pole 12 when the elongate pole 12 is coupled to the bottom base 58.

In some embodiments, the elongate pole 12 is configured for use with both the door mount embodiment shown in FIGS. 1 and 2 and the mobile stand embodiments discussed herein. As previously discussed, the elongate pole 12 may be detachably coupled to the top bracket 22a and the bottom bracket 22b of the system 10. Once decoupled from the bottom bracket 22b, the elongate pole 12 may be configured to couple to the bottom base 58. The bottom base 58 may be configured to couple to a variety of stands, as will be discussed in further detail with reference to FIGS. 10-21. As such, a user of the system 10 may obtain a single elongate pole 12 to facilitate use of a light therapy device 30 on a door mount, a mobile stand, and/or a fixed stand. Stated differently, the elongate pole 12 may be interchangeably coupled to a variety of components (e.g., top bracket 22a, bottom bracket 22b, bottom base 58) in order to facilitate a variety of mounting methods (door mount, mobile stand, fixed stand) for a light therapy device 30.

Figure 10:
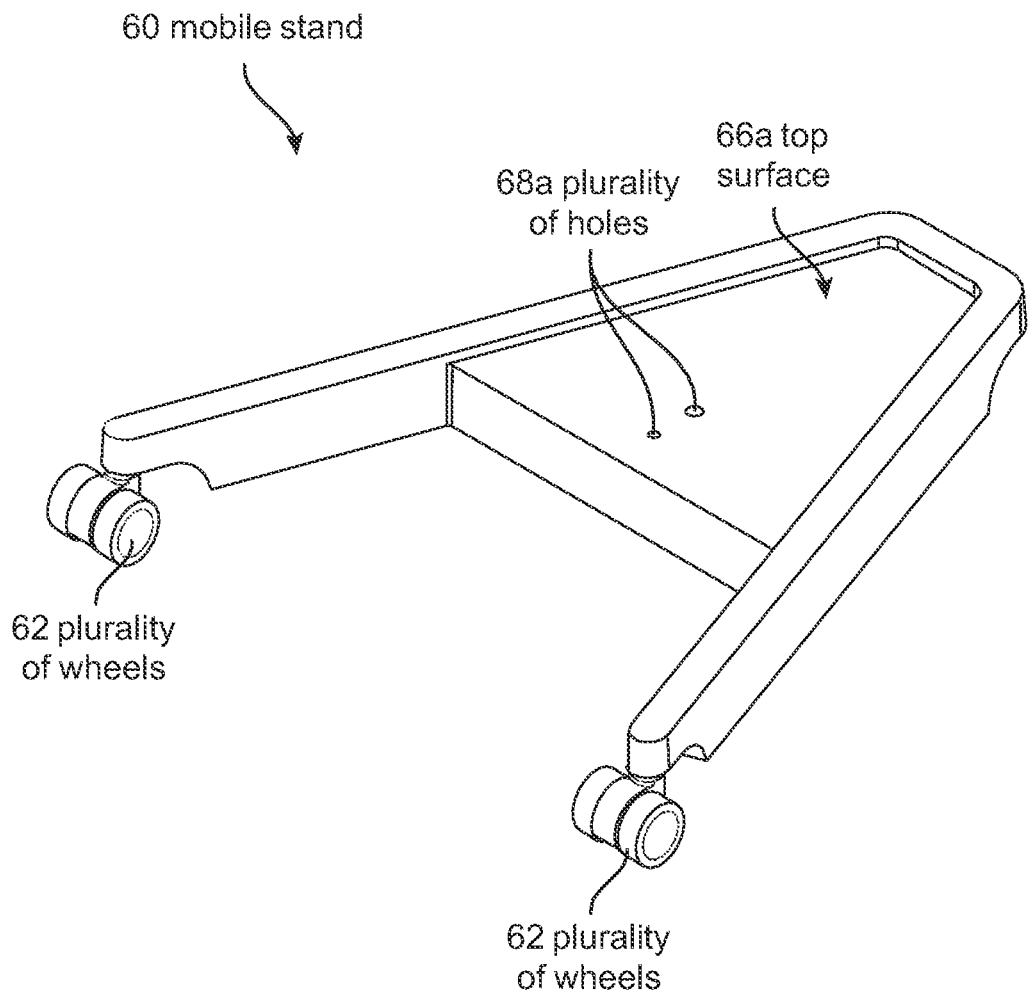
FIG. 10 illustrates a perspective view of a mobile stand, according to some embodiments.

Referring now to FIG. 10, the system 10 may include a mobile stand 60. In some embodiments, the mobile stand 60 comprises a plurality of wheels 62. The plurality of wheels 62 may include two, three, four, or more than four wheels. In some embodiments, the mobile stand 60 includes a single wheel. The mobile stand 60 may include an alternative to a traditional wheel, including but not limited to, a slideable surface (e.g., sled), a continuous track, and/or a pedrail wheel.

FIG. 10 also shows that, in many embodiments, the mobile stand 60 includes a top surface 66a. The top surface 66a may include a plurality of holes 68a. In many embodiments, the plurality of holes 68a is configured to couple the mobile stand 60 to the elongate pole 12 via the bottom base 58. FIG. 9 illustrates that the bottom base 58 may include at least one coupling mechanism 70, and, in some embodiments, the plurality of holes 68a are configured to receive the at least one coupling mechanism 70. The at least one coupling mechanism 70 may include any number of suitable coupling mechanisms, including, but not limited to, fasteners such as a screw(s), a bolt(s), a nut(s), a machine screw(s), and any combination thereof. The plurality of holes 68a may be located anywhere on the top surface 66a. In some embodiments, the bottom base 58 comprises a pad configured to couple between the bottom base 58 and the mobile stand 60. The pad may be configured to act as a buffer; for example, when the bottom base 58 and mobile stand 60 comprise metallic materials, the pad may comprise a plastic material.

Figure 11:
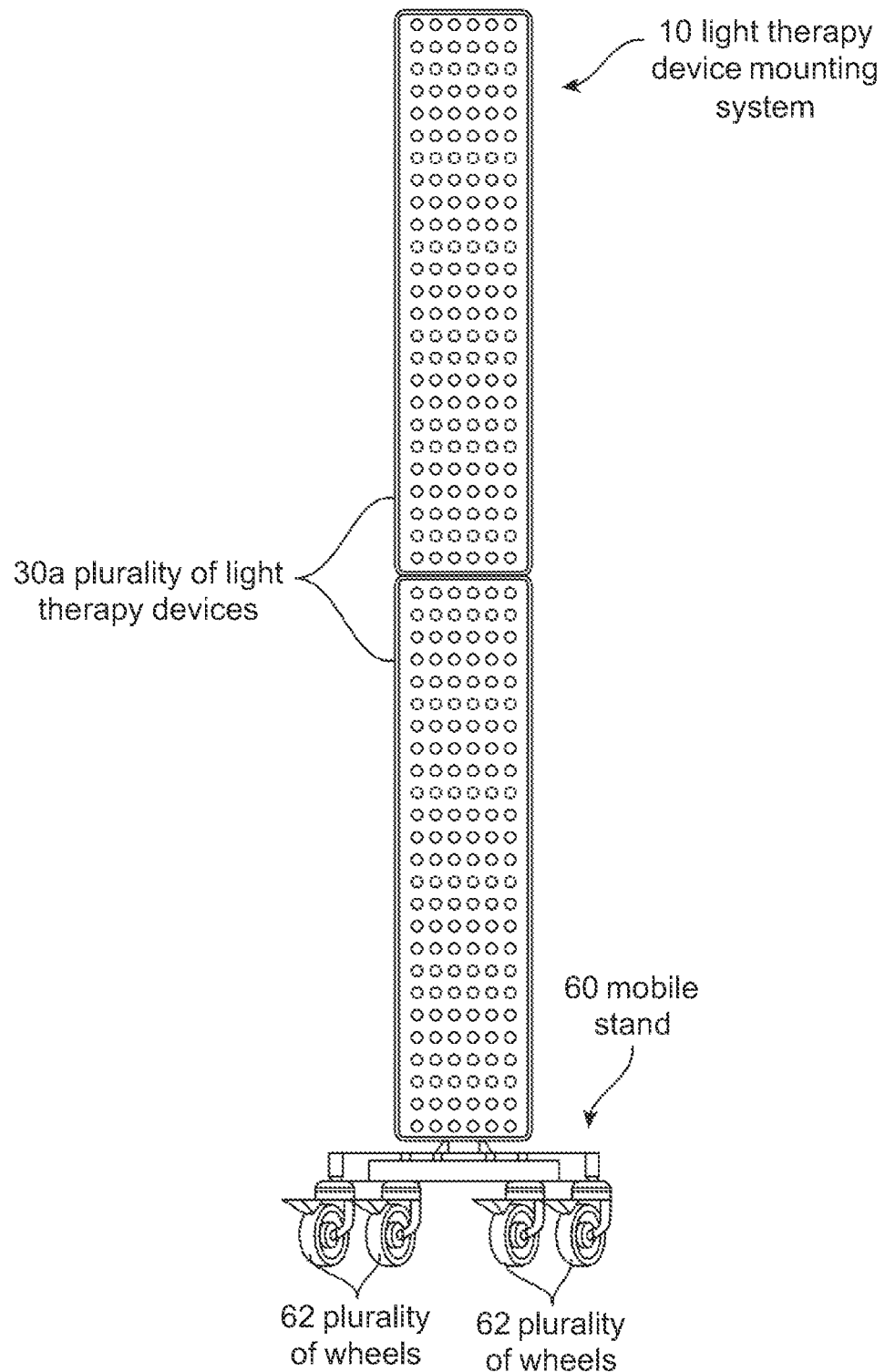
FIG. 11 illustrates a front view of a plurality of light therapy devices coupled to a mobile stand, according to some embodiments.
Figure 12:
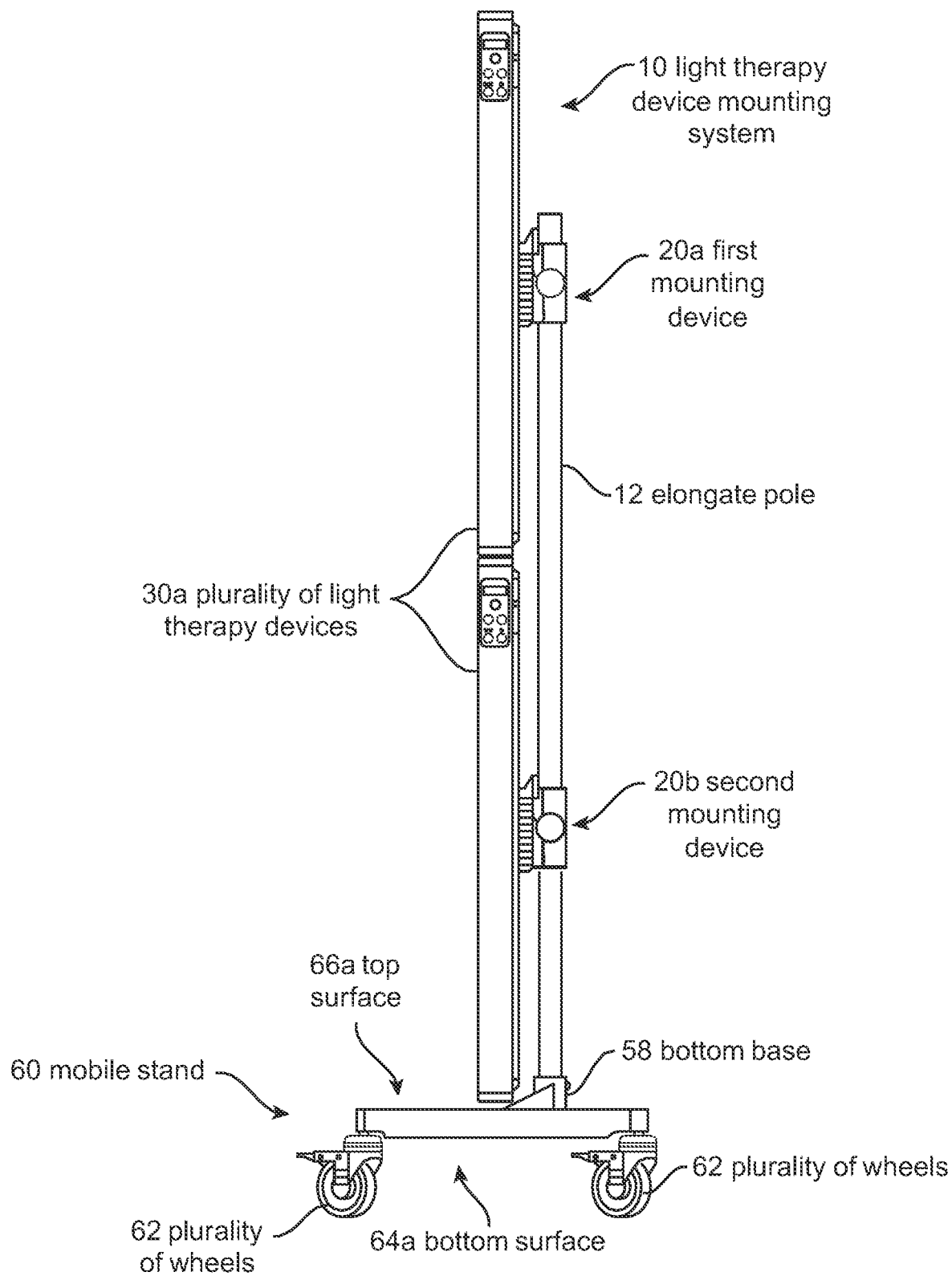
FIG. 12 illustrates a side view of a plurality of light therapy devices coupled to a mobile stand, according to some embodiments.

FIG. 11 illustrates a front view of the system 10 with a plurality of light therapy devices 30a coupled to the mobile stand 60. As previously stated, in some embodiments, the plurality of wheels 62 includes four wheels. FIG. 12 shows a side view of the system 10, including a plurality of light therapy devices 30a coupled to a mobile stand 60. As discussed with reference to FIG. 9, in some embodiments, the elongate pole 12 comprises a first mounting device 20a and a second mounting device 20b. FIG. 12 shows the elongate pole 12 with the first and second mounting devices 20a, 20b, where the use of first and second mounting devices 20a, 20b allows for the coupling of a plurality of light therapy devices 30a to the elongate pole 12. In some embodiments, each light therapy device 30 is smaller than the devices 30a shown in FIGS. 11 and 12. As such, the plurality of light therapy devices 30a may comprise more than two devices 30a. For example, three light therapy devices 30a may couple to the elongate pole 12 via three mounting devices 20. In some embodiments, more than three light therapy devices 30a and more than three mounting devices 20 are sized and configured to couple to the elongate pole 12. The elongate pole 12 may define a height greater than what is depicted in the Figures, such that the elongate pole 12 is sized and configured to fit more than two light therapy devices 30a of the size shown in FIGS. 11 and 12.

FIG. 12 also shows the bottom base 58 coupled to the top surface 66a of the mobile stand 60. In some embodiments, the bottom base 58 is larger than the base 58 depicted in FIG. 12, such that the base 58 extends further across the top surface 66a of the stand 60. Stated differently, the bottom base 58 may comprise a larger "footprint" on the top surface 66a such that it takes up a larger portion of the top surface 66a. The bottom base 58 may also define a greater height such that it is configured to receive a greater portion of the elongate pole 12. In some embodiments, the bottom base 58 is smaller than the embodiment shown in FIG. 12. The Figure also shows that, in many embodiments, the plurality of wheels 62 is coupled to a bottom surface 64a of the mobile stand 60. The bottom surface 64a may be located opposite from the top surface 66a.

Figure 13:
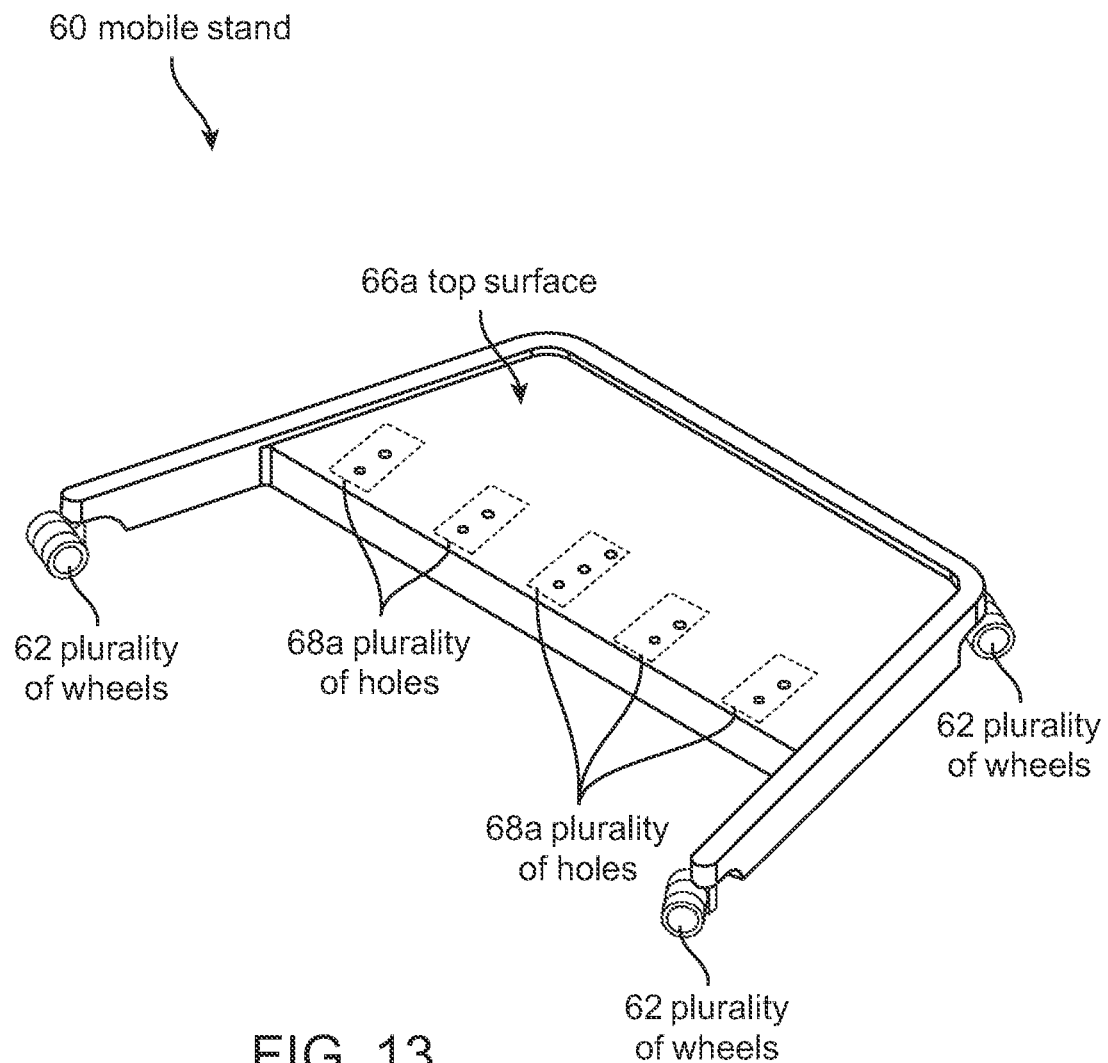
FIG. 13 illustrates a perspective view of a mobile stand, according to some embodiments.

FIG. 13 illustrates another embodiment of the mobile stand 60. As shown, in some embodiments, the mobile stand 60 is larger than the stand 60 shown in FIG. 10. A larger embodiment of the mobile stand 60 may include a more numerous plurality of holes 68a on the top surface 66a. For example, as shown in FIG. 13, the mobile stand 60 may include five sets in the plurality of holes 68a, as compared to the single set shown on the mobile stand 60 in FIG. 10. In some embodiments, the mobile stand 60 includes a plurality of holes 68a comprising two, three, or four sets of holes. The mobile stand 60 may include more than five sets of holes in the plurality of holes 68a. It should be noted that each "set" of holes in the plurality of holes 68a may include one, two, three, four, or more than four holes. In some embodiments, each "set" of holes is configured to couple to a bottom base 58. As such, the mobile stand 60 shown in FIG. 13 may be sized and configured to couple to up to five bottom bases 58, and therefore, up to five elongate poles 12.

Instead of a plurality of holes 68a coupled to at least one coupling mechanism 70, the bottom base 58 may be configured to couple to the top surface 66a of the mobile stand 60 via other coupling methods, including, but not limited to, adhesive, magnet(s), welding, and the like. The bottom base 58 may be fixedly coupled to the mobile stand 60 (e.g., adhesive, welding, etc.). In some embodiments, the bottom base 58 is detachably coupled to the mobile stand 60 (magnets, plurality of holes 68a with at least one coupling mechanism 70, etc.). In some embodiments, the bottom base 58 comprises a pad configured to couple between the bottom base 58 and the mobile stand 60. The pad may be configured to act as a buffer; for example, when the bottom base 58 and mobile stand 60 comprise metallic materials, the pad may comprise a plastic material.

Figure 14:
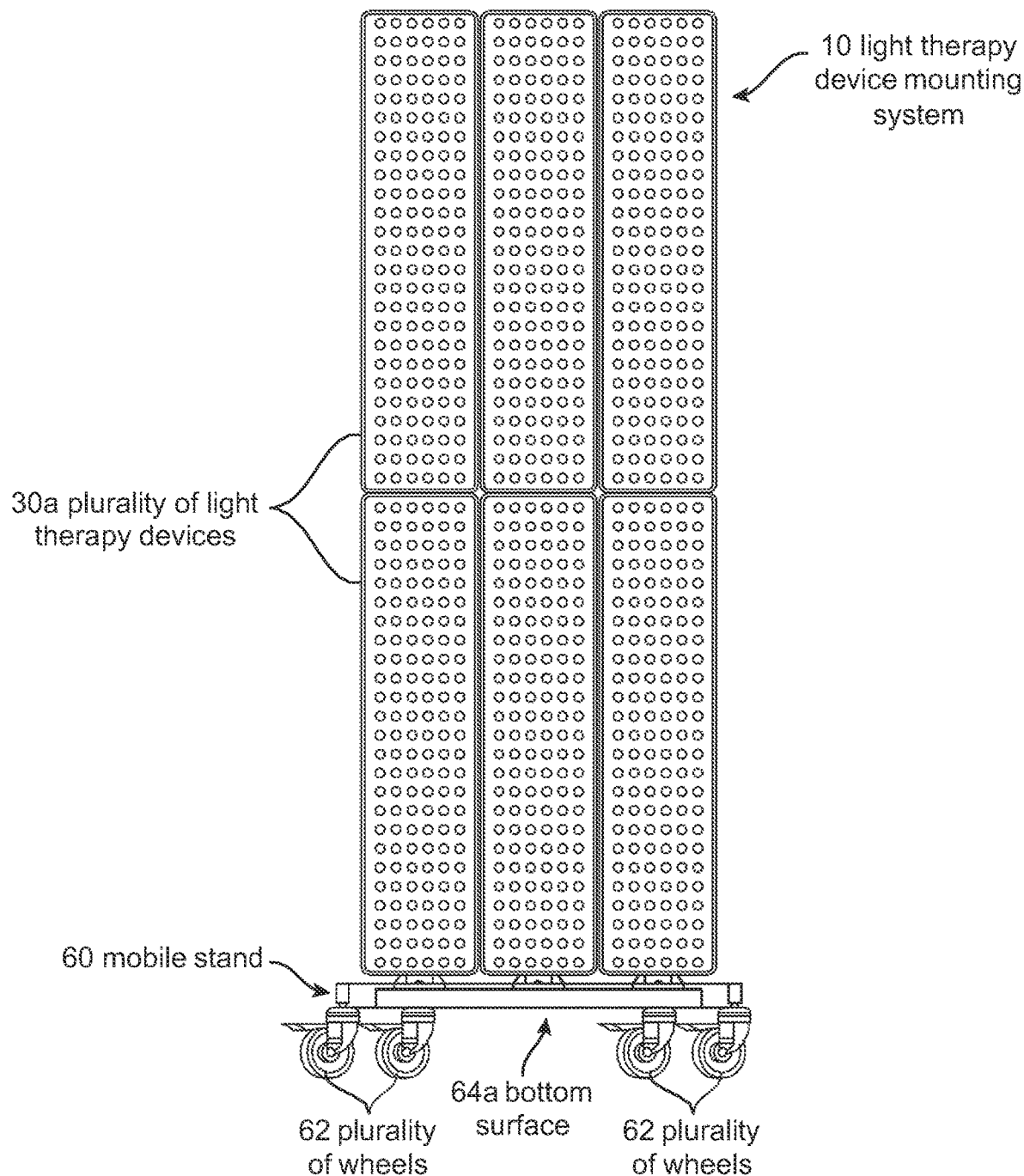
FIG. 14 illustrates a front view of a plurality of light therapy devices coupled to a mobile stand, according to some embodiments.

FIG. 14 shows a front view of a plurality of light therapy devices 30a coupled to the mobile stand 60. Similar to the mobile stand 60 shown in FIGS. 10-12, the mobile stand 60 of FIGS. 13-15 and 17 may include a plurality of wheels 62. The plurality of wheels 62 may include two, three, four, or more than four wheels. In some embodiments, the mobile stand 60 includes a single wheel. The mobile stand 60 may include an alternative to a traditional wheel, including but not limited to, a slideable surface (e.g., sled), a continuous track, and/or a pedrail wheel. In many embodiments, the plurality of wheels 62 (or alternative device) is coupled to a bottom surface 64a of the mobile stand 60. The bottom surface 64a may be located opposite the top surface 66a, such that the plurality of wheels 62 may be coupled to a surface of the mobile stand 60 opposite from the surface of the mobile stand 60 coupled to the bottom base(s) 58. FIG. 14 also shows that the plurality of light therapy devices 30a may include more than two light therapy devices 30a. In some embodiments, as shown in FIG. 14, the plurality of light therapy devices 30a comprises six light therapy devices 30a. The plurality of light therapy devices 30a may comprise three, four, or five light therapy devices 30a. In some embodiments, the plurality of light therapy devices 30a comprises more than six light therapy devices 30. A single light therapy device 30 may be coupled to the mobile stand 60.

Figure 15:
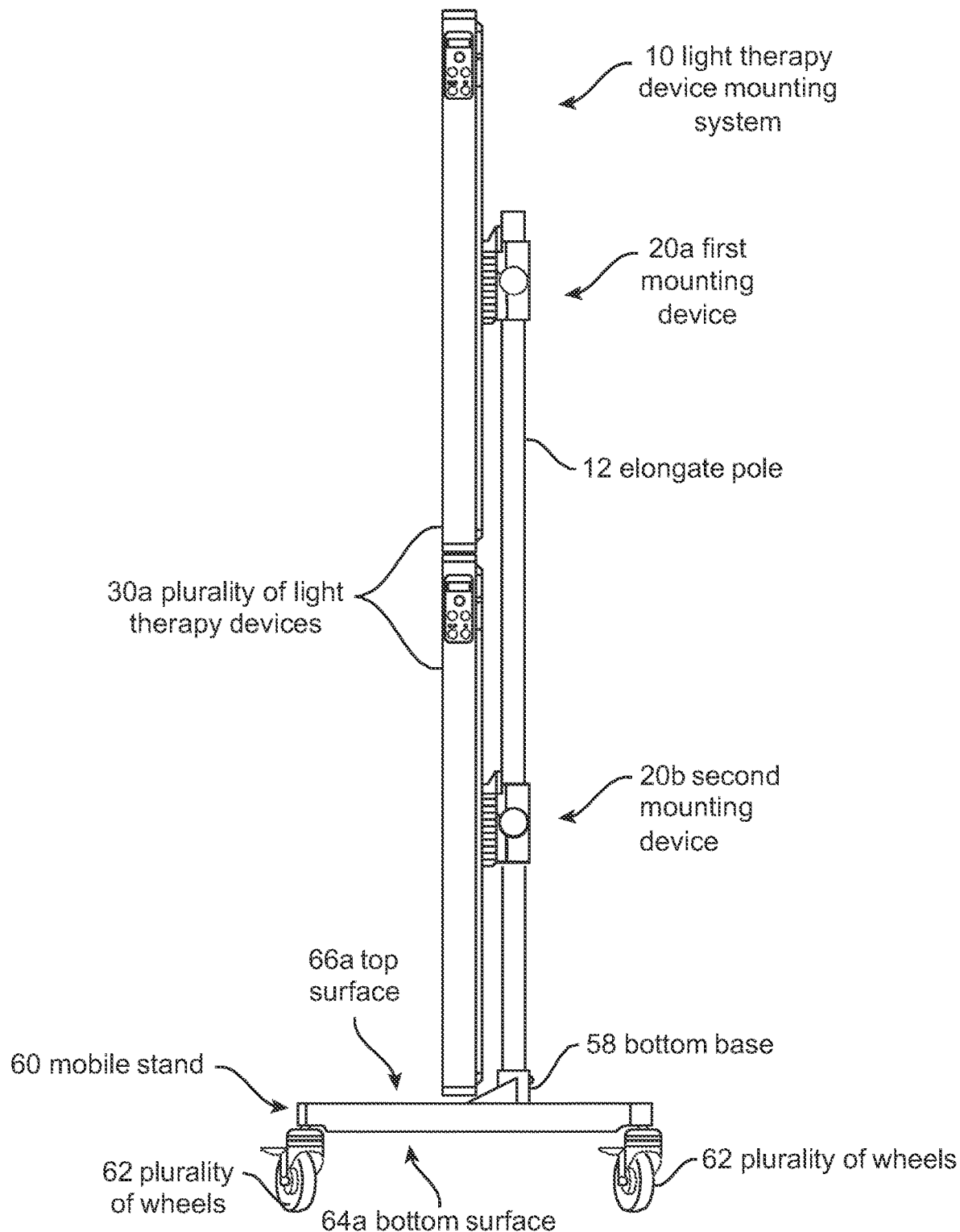
FIG. 15 illustrates a side view of a plurality of light therapy devices coupled to a mobile stand, according to some embodiments.

Similar to FIG. 12, FIG. 15 illustrates a side view of the system 10, including a plurality of light therapy devices 30a coupled to a mobile stand 60. Though shown with only two light therapy devices 30a in the plurality of light therapy devices 30a, it should be noted that FIG. 15 may be considered to show a side view of the same embodiment of the system 10 depicted in FIG. 14. As will be discussed further with reference to FIG. 17, the system 10 shown in FIGS. 14 and 15 may include three elongate poles 12, where each pole 12 comprises a first and second mounting device 20a, 20b. Each mounting device 20a, 20b may be configured to couple to a light therapy device 30. As such, the use of three elongate poles 12, where each pole 12 is coupled to two light therapy devices 30a, facilitates the embodiment of the system 10 shown in FIG. 14 with six light therapy devices 30a.

FIG. 15 also shows the bottom base 58 coupled to the top surface 66a of the mobile stand 60. In some embodiments, the bottom base 58 is larger than the base 58 depicted in FIG. 15, such that the base 58 extends further across the top surface 66a of the stand 60. Stated differently, the bottom base 58 may comprise a larger "footprint" on the top surface 66a such that it takes up a larger portion of the top surface 66a. The bottom base 58 may also define a greater height such that it is configured to receive a greater portion of the elongate pole 12. In some embodiments, the bottom base 58 is smaller than the embodiment shown in FIG. 15.

Figure 16A:
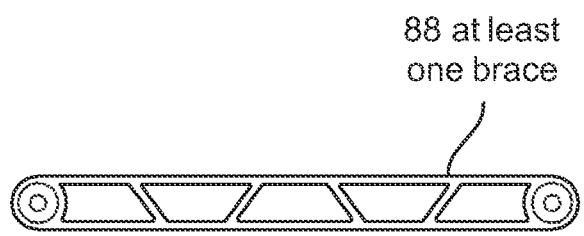
FIGS. 16A and 16B illustrate various embodiments of at least one brace.
Figure 16B:
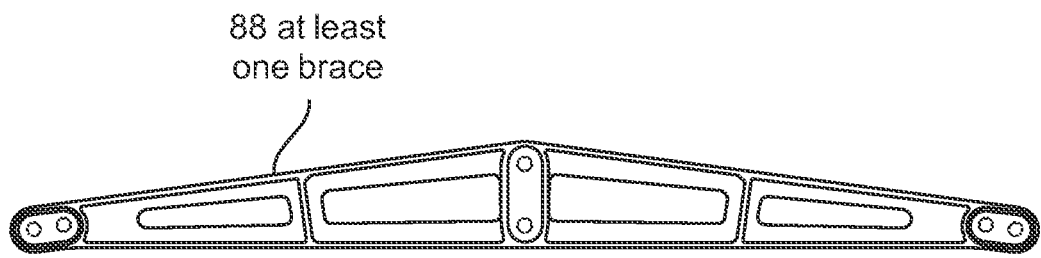

FIGS. 16A and 16B illustrate embodiments of at least one brace 88. In many embodiments, the at least one brace 88 is configured to provide stability to the system 10 when the system 10 includes multiple elongate poles 12 coupled to a mobile stand 60. The at least one brace 88 may be sized and configured to couple to a top portion of at least one elongate pole 12. For example, the at least one brace 88 shown in FIG. 16A may be configured to couple to the top portions of two elongate poles 12, and the at least one brace 88 shown in FIG. 16B may be configured to couple to the top portions of three elongate poles 12. In some embodiments, the at least one brace 88 is configured to couple to each elongate pole 12 at at least one point of the elongate pole 12; for example, a top surface of each elongate pole 12. The at least one brace 88 may be configured to couple to each elongate pole 12 at the top surface and at least one other point on the elongate pole 12. For example, the at least one brace 88 may be configured to couple to each elongate pole 12 at the top surface and a back, front, and/or side surface.

The at least one brace 88 may be configured to detachably couple to each elongate pole 12 via any of the coupling mechanisms mentioned in this disclosure. The at least one brace 88 may be configured to fixedly couple to each elongate pole 12 via any of the coupling mechanisms mentioned in this disclosure. For example, the holes shown on the at least one brace 88 (in both FIGS. 16A and 16B) may be configured to receive at least one coupling mechanism 70 in a manner similar to the plurality of holes 68a located on the mobile stand 60. The elongate pole 12 may include holes configured to receive at least one coupling mechanism 70. These holes may be separate from the plurality of holes 14. In some embodiments, at least one hole of the plurality of holes 14 is configured to receive at least one coupling mechanism 70 in order to couple the elongate pole 12 to at least one brace 88.

Figure 17:
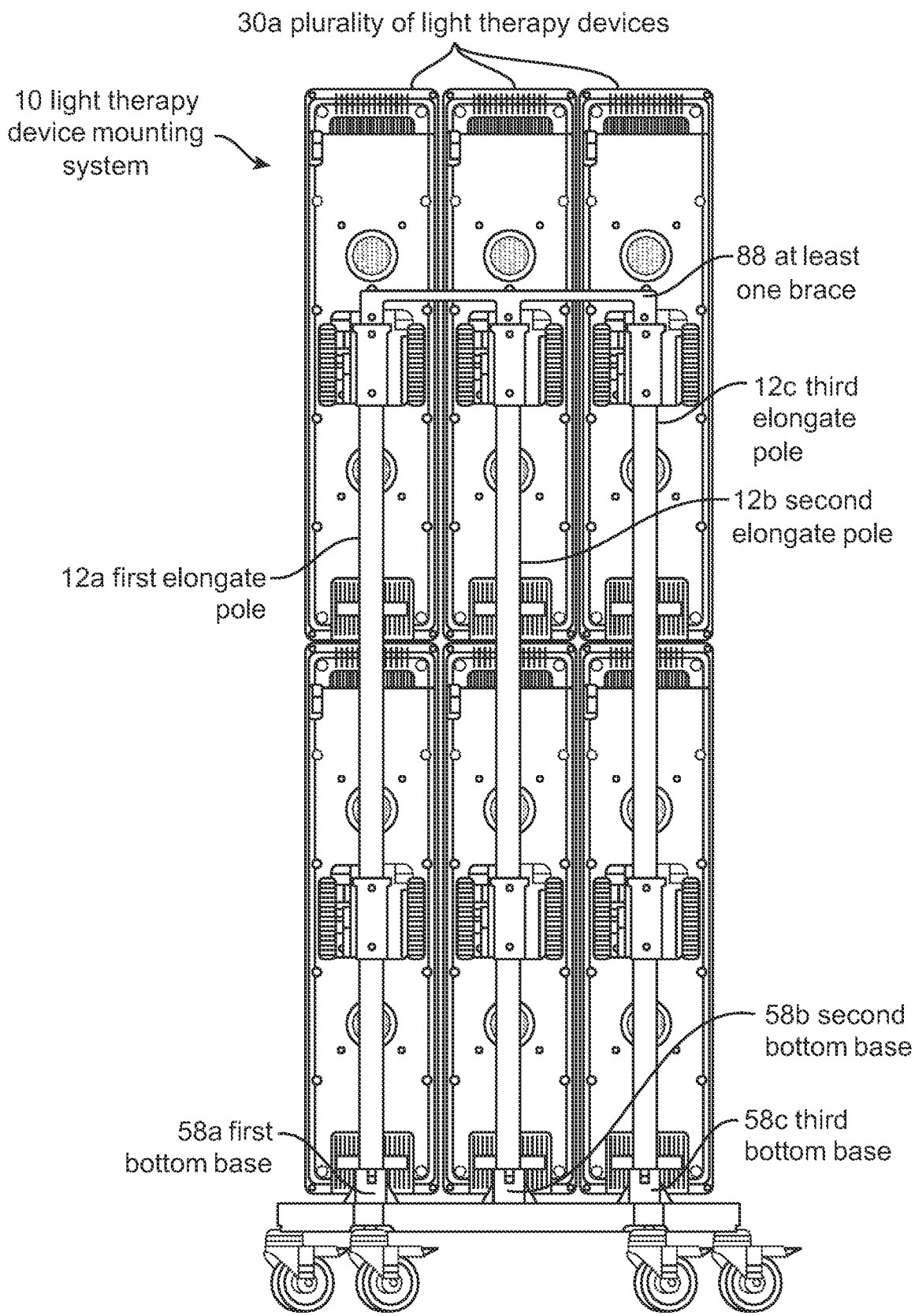
FIG. 17 illustrates a back view of a plurality of light therapy devices coupled to a mobile stand, according to some embodiments.

FIG. 17 shows a back view of the system 10 depicted in FIGS. 14 and 15. In some embodiments, the system 10 includes a plurality of light therapy devices 30a comprising six light therapy devices 30a, a first elongate pole 12a, a second elongate pole 12b, a third elongate pole 12c, a first bottom base 58a, a second bottom base 58b, and a third bottom base 58c. The first bottom base 58a may be configured to receive the first elongate pole 12a, the second bottom base 58b may be configured to receive the second elongate pole 12b, and the third bottom base 58c may be configured to receive the third elongate pole 12c. As previously discussed, each elongate pole 12 may be configured to couple to two light therapy devices 30a via a first and second mounting device 20a, 20b. FIG. 17 also includes the at least one brace 88, which is shown extending across the top portions of the first, second, and third elongate poles 12a, 12b, and 12c. The at least one brace 88 may be configured to provide stability to the system 10 by coupling the elongate poles 12a, 12b, and 12c. The stability may be important to reduce movement of each elongate pole 12 during movement of the system 10, such as when the mobile stand 60 is rolled from one area to another, or in case of a sudden movement, like an earthquake or a person bumping into the system 10. The stability from the at least one brace 88, combined with the stability from each bottom base 58 coupled to the mobile stand 60, may provide a substantial amount of support and stability to the system 10 and protect the plurality of light therapy devices 30a from damage.

As stated with reference to FIG. 13, the mobile stand 60 may be configured to support up to five elongate poles 12. FIG. 17 demonstrates that the number of elongate poles 12 in the system 10 may be dependent on the size of each light therapy device 30 of the plurality of light therapy devices 30a. For example, FIG. 17 includes three elongate poles 12a, 12b, and 12c and shows, along with FIG. 14, that the plurality of light therapy devices 30a does not include much space between each light therapy device 30. As such, the embodiment shown in FIGS. 14 and 17 may not be suitable for more than three elongate poles 12a, 12b, and 12c. In some embodiments, each light therapy device 30 comprises a narrower light therapy device 30 than the devices 30a shown in the Figures. In such an embodiment, there may be enough room to accommodate four or five elongate poles 12 on the mobile stand 60. In contrast, each light therapy device 30 may comprise a wider light therapy device 30 than the devices 30a shown in the Figures. In such an embodiment, the stand 60 shown in FIGS. 13-15 and 17 may only accommodate one or two elongate poles 12. Depending on the size of each light therapy device 30, each device 30 may be configured to couple to a first elongate pole 12a and a second elongate pole 12b in order to provide sufficient support for each light therapy device 30.

Fixed Stand System Embodiments

Figure 18:
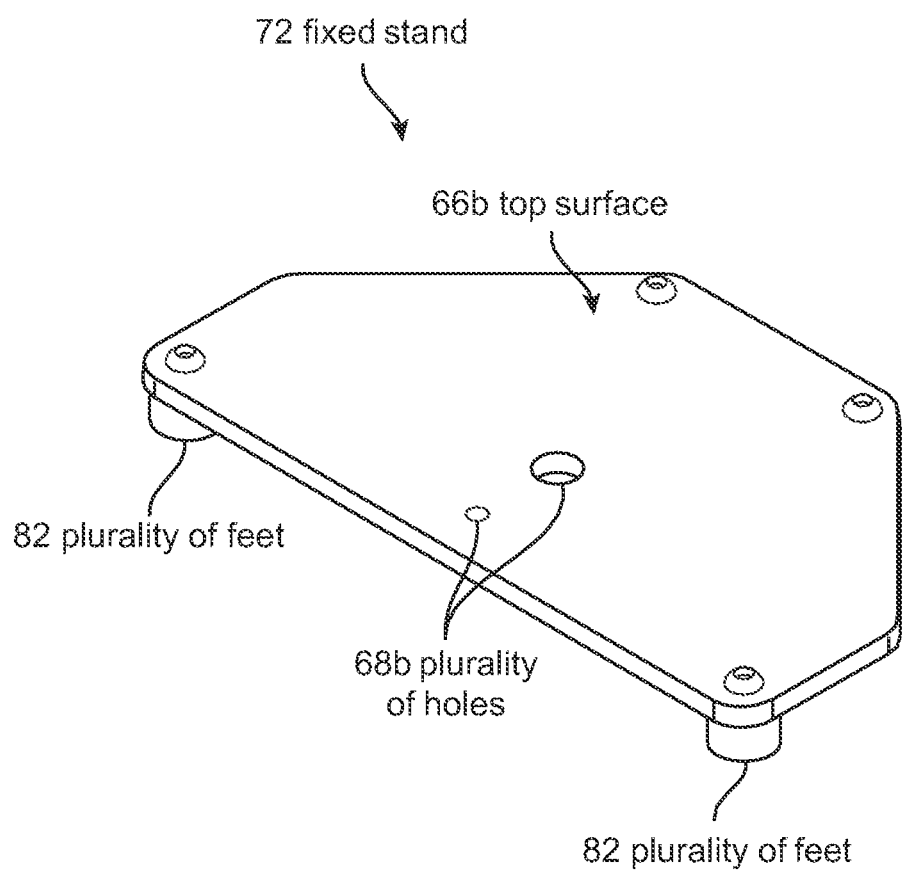
FIG. 18 illustrates a perspective view of a fixed stand, according to some embodiments.
Figure 19:
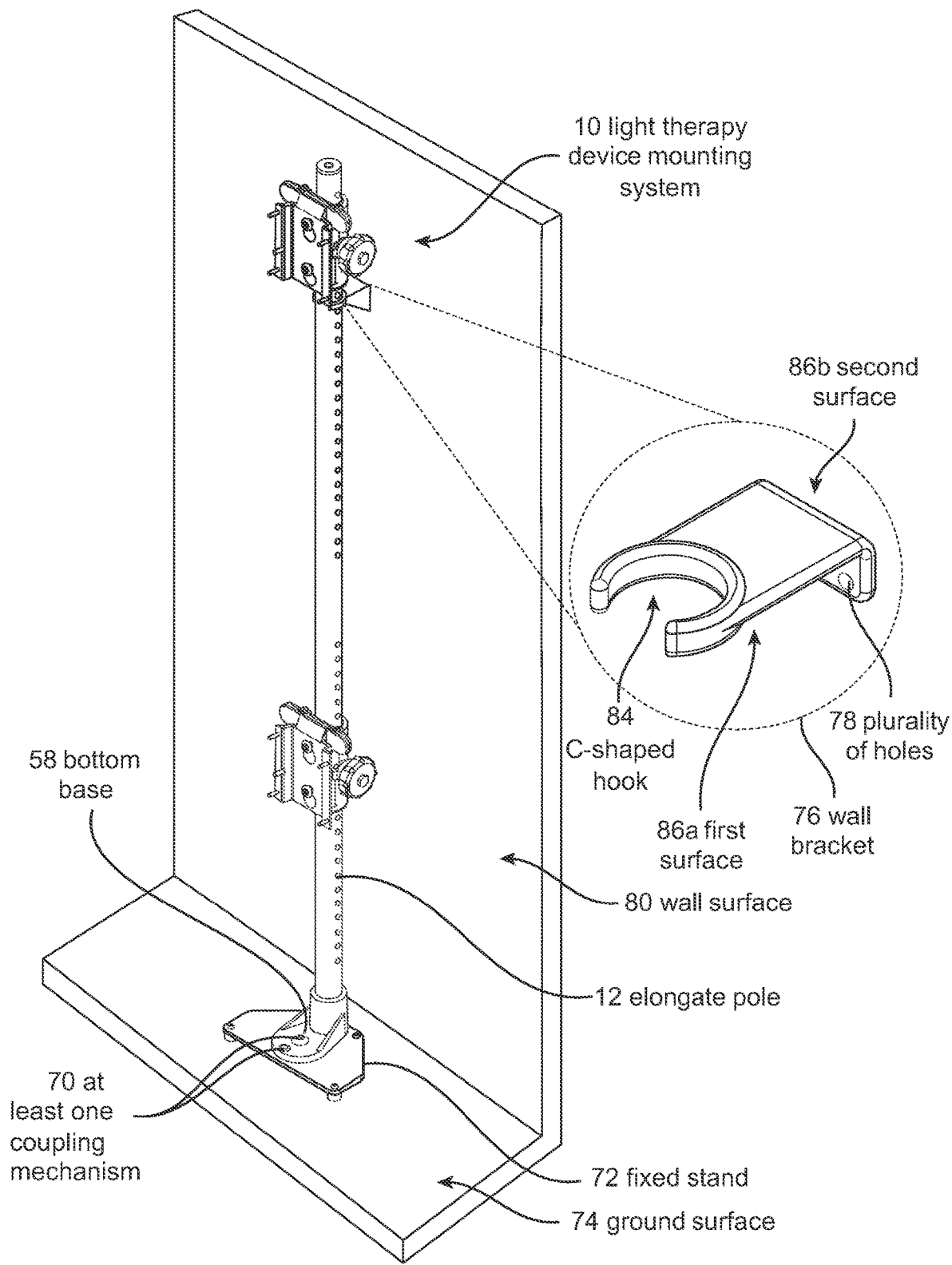
FIG. 19 illustrates a perspective view of a light therapy device mounting system, including a wall bracket, according to some embodiments.

FIG. 18 shows an embodiment of a fixed stand 72, including a top surface 66b, a plurality of holes 68b, and a plurality of feet 82. The plurality of feet 82 may include two, three, four, or more than four feet configured to contact a ground surface 74 (as shown in FIG. 19). In some embodiments, the fixed stand 72 includes a single foot configured to contact the ground surface 74. The plurality of feet 82 may be located on a bottom surface 64b of the fixed stand 72 located opposite the top surface 66b. Similar to the mobile stand 60, in many embodiments, the plurality of holes 68b is configured to couple the fixed stand 72 to the elongate pole 12 via the bottom base 58.

FIG. 19 illustrates that the bottom base 58 may include at least one coupling mechanism 70, and, in some embodiments, the plurality of holes 68b is configured to receive the at least one coupling mechanism 70. The at least one coupling mechanism 70 may include any number of suitable coupling mechanisms, including, but not limited to, fasteners such as a screw(s), a bolt(s), a nut(s), a machine screw(s), and any combination thereof. The plurality of holes 68b may be located anywhere on the top surface 66b. In some embodiments, the bottom base 58 comprises a pad configured to couple between the bottom base 58 and the fixed stand 72. The pad may be configured to act as a buffer; for example, when the bottom base 58 and fixed stand 72 comprise metallic materials, the pad may comprise a plastic material.

Instead of a plurality of holes 68b coupled to at least one coupling mechanism 70, the bottom base 58 may be configured to couple to the top surface 66b of the fixed stand 72 via other coupling methods, including, but not limited to, adhesive, magnet(s), welding, and the like. The bottom base 58 may be fixedly coupled to the fixed stand 72 (e.g., adhesive, welding, etc.). In some embodiments, the bottom base 58 is detachably coupled to the fixed stand 72 (magnets, plurality of holes 68b with at least one coupling mechanism 70, etc.).

Though illustrated as an irregular hexagon, it should be noted that the fixed stand 72 may define any shape suitable to support at least one bottom base 58 coupled to at least one elongate pole 12 and at least one light therapy device 30. For example, the fixed stand 72 may define a round, ovoid, triangular, rectangular, pentagonal, hexagonal, heptagonal, etc. shape. The fixed stand 72 may also be sized to include multiple sets of holes in the plurality of holes 68b, similar to the mobile stand 60 shown in FIG. 13, such that the fixed stand 72 may accommodate multiple elongate poles 12 via coupling to multiple bottom bases 58. Each foot of the plurality of feet 82 may define any suitable shape.

In some embodiments, as illustrated in FIG. 19, the system 10 includes a wall bracket 76 coupled to the elongate pole 12 when the elongate pole 12 is coupled to the fixed stand 72. The wall bracket 76 may include a C-shaped hook 84 located on a first surface 86a of the wall bracket 76, as well as a plurality of holes 78 located on a second surface 86b of the wall bracket 76. The first surface 86a may be located opposite the second surface 86b. In many embodiments, the C-shaped hook 84 is configured to flex in order to snapably receive the elongate pole 12 to thereby couple the elongate pole 12 to the wall bracket 76, and thereby, to couple the elongate pole 12 to the wall surface 80. The C-shaped hook 84 may be configured to couple to the elongate pole 12 in another manner, such as slidably receiving the elongate pole 12. The C-shaped hook 84 may comprise another suitable shape, such as "D" or "0." In some embodiments, the C-shaped hook 84 comprises a hinged closure, similar to that commonly found on a carabiner. The C-shaped hook 84 may comprise a shape configured to substantially surround the elongate pole 12 when the wall bracket 76 is coupled to the elongate pole 12. The C-shaped hook 84 may be configured to couple to any suitable portion of the elongate pole 12, including a first end 16, a second end 18, and/or a middle portion.

In many embodiments, the second surface 86b is configured to contact a wall surface 80, and the plurality of holes 78 is configured to receive a coupling mechanism in order to couple the wall bracket 76 to the wall surface 80. The coupling mechanism may be the same as the at least one coupling mechanism 70. In some embodiments, the coupling mechanism configured to couple the wall bracket 76 to the wall surface 80 comprises at least one drywall screw or similar mechanism. The plurality of holes 78 may comprise two, three, four, or more than four holes. The holes may be configured in a side-by-side or top-to-bottom pattern. In some embodiments, the plurality of holes 78 comprises a single hole.

Figure 20:
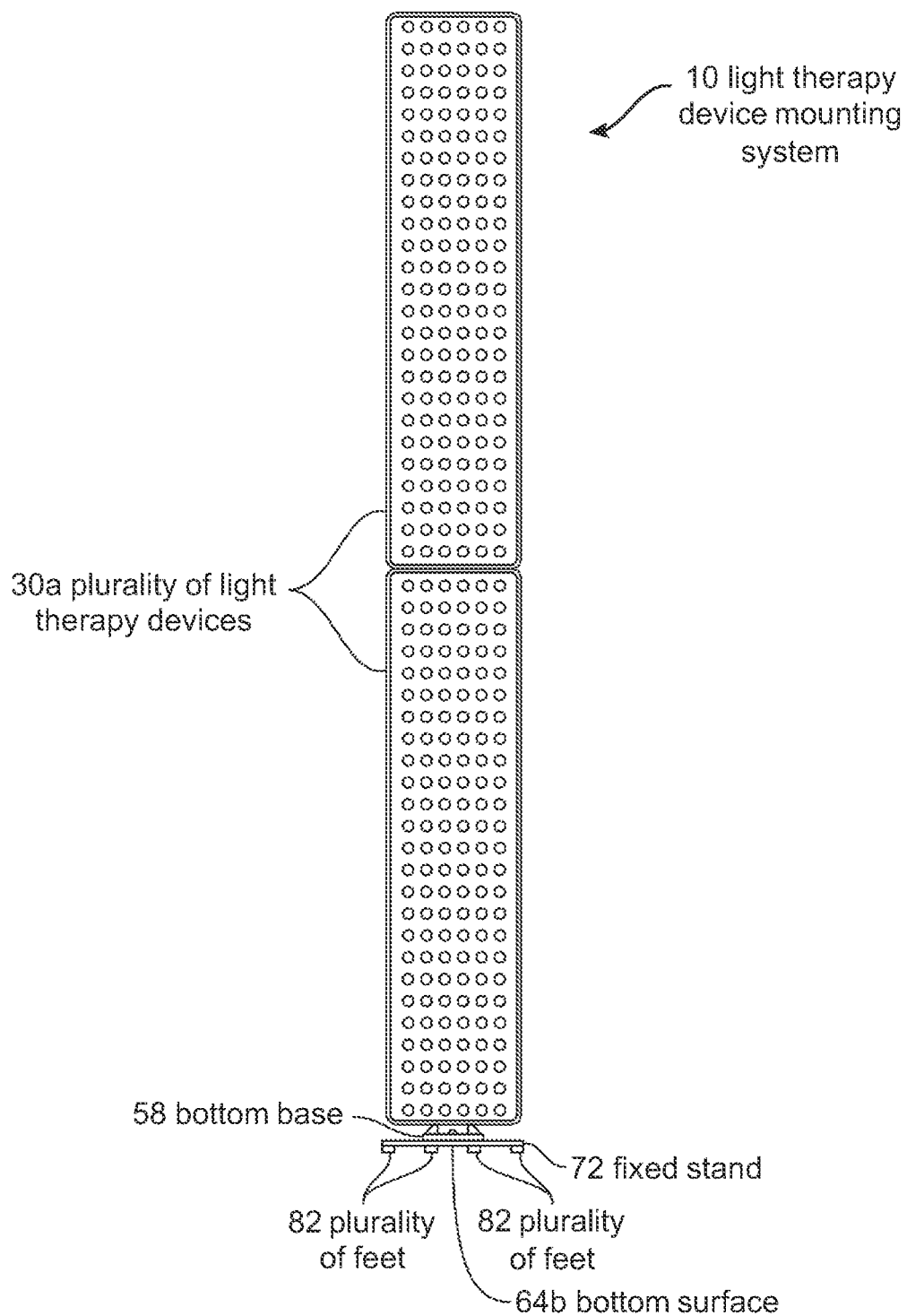
FIG. 20 illustrates a front view of a plurality of light therapy devices coupled to a fixed stand, according to some embodiments.
Figure 21:
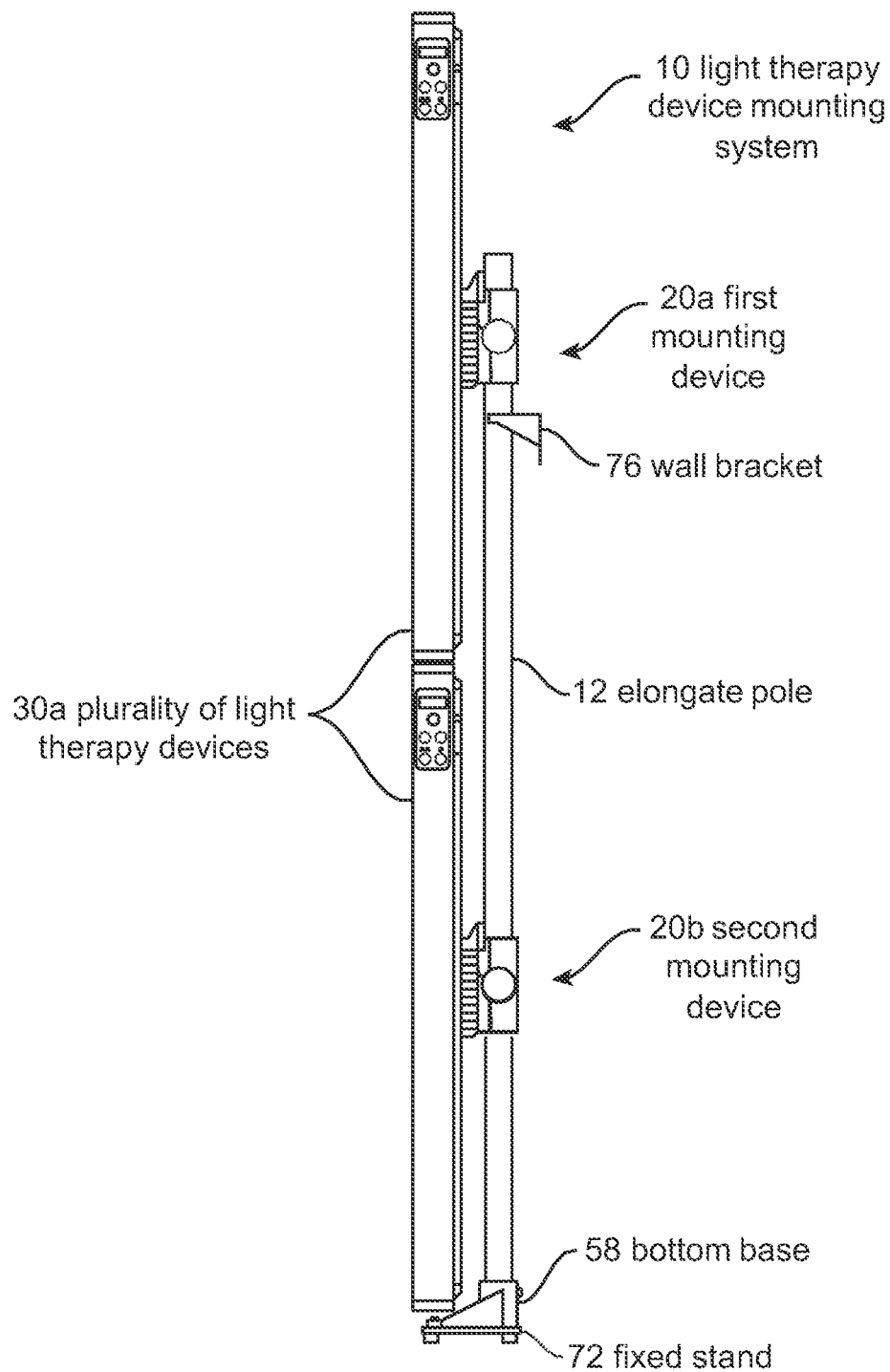
FIG. 21 illustrates a side view of a plurality of light therapy devices coupled to a fixed stand, according to some embodiments.

FIG. 20 shows a front view of the system 10, including a plurality of light therapy devices 30a coupled to the fixed stand 72 via the bottom base 58. As previously stated, in some embodiments, the plurality of feet 82 includes four feet. The plurality of feet 82 may be coupled to a bottom surface 64b of the fixed stand 72. FIG. 21 shows a side view of the system 10, including a plurality of light therapy devices 30a coupled to a fixed stand 72. As discussed with reference to FIG. 9, in some embodiments, the elongate pole 12 comprises a first mounting device 20a and a second mounting device 20b. FIG. 21 shows the elongate pole 12 with the first and second mounting devices 20a, 20b, where the use of first and second mounting devices 20a, 20b allows for the coupling of a plurality of light therapy devices 30a to the elongate pole 12.

FIG. 21 also shows that, in some embodiments, the wall bracket 76 is located between the first mounting device 20a and the second mounting device 20b. The wall bracket 76 may be located above the first mounting device 20a. The wall bracket 76 may be located below the second mounting device 20b. In some embodiments, the wall bracket 76 is located closer to the first mounting device 20a than the second mounting device 20b. The wall bracket 76 may be located closer to the second mounting device 20b than the first mounting device 20a. The wall bracket 76 may be located substantially equidistant from the first mounting device 20a and the second mounting device 20b. Some embodiments of the system 10 include a plurality of wall brackets 76 coupled to the elongate pole 12. The system 10 may include a plurality of elongate poles 12, with at least one wall bracket 76 coupled to each elongate pole 12.

FIGS. 19-21 depict the bottom base 58 coupled to the top surface 66b of the fixed stand 72. In some embodiments, the bottom base 58 is larger than the base 58 depicted in FIGS. 19, 20, and/or 21, such that the base 58 extends further across the top surface 66b of the stand 72. Stated differently, the bottom base 58 may comprise a larger "footprint" on the top surface 66b such that it takes up a larger portion of the top surface 66b. The bottom base 58 may also define a greater height such that it is configured to receive a greater portion of the elongate pole 12. In some embodiments, the bottom base 58 is smaller than the embodiments shown in FIGS. 19, 20, and/or 21.

As previously mentioned, the fixed stand 72 may be sized to accommodate multiple bottom bases 58 such that multiple elongate poles 12 may be supported by the fixed stand 72. In some embodiments, when the fixed stand 72 is coupled to a plurality of elongate poles 12, the system 10 includes at least one brace 88, similar to those illustrated in FIGS. 16A and 16B. The at least one brace 88 may also be used when the system 10 comprises multiple fixed stands 72 located adjacent one another. For example, in some embodiments, the system 10 includes three fixed stands 72 located adjacent one another, each fixed stand 72 comprising an elongate pole 12 coupled to at least one light therapy device 30. The system 10 may also include at least one brace 88, such as the brace illustrated in FIG. 16B, configured to couple to each elongate pole 12 to provide stability to the system 10.

Floor Stand System Embodiments

Figure 22:
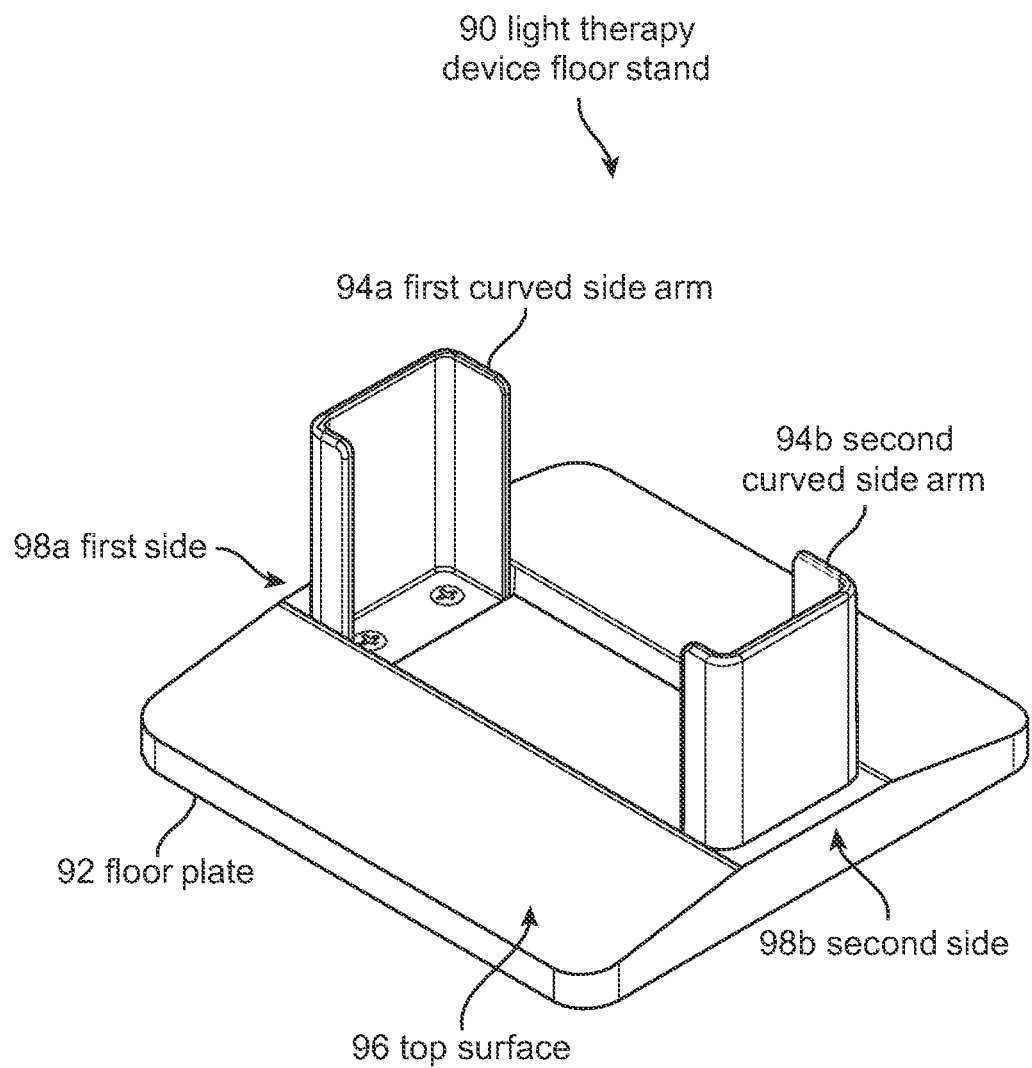
FIG. 22 illustrates a perspective view of a light therapy device floor stand, according to some embodiments.

Referring now to FIG. 22, a light therapy device floor stand 90 may include a floor plate 92 comprising a first curved side arm 94a and a second curved side arm 94b. In many embodiments, the first curved side arm 94a and second curved side arm 94b are coupled to a top surface 96 of the floor plate 92. At least one of the first curved side arm 94a and the second curved side arm 94b may be coupled to the top surface 96a via any of the coupling mechanisms mentioned in this disclosure. At least one of the first curved side arm 94a and the second curved side arm 94b may be fixedly coupled to the floor plate 92. In some embodiments, at least one of the first curved side arm 94a and the second curved side arm 94b is detachably coupled to the floor plate 92. The first curved side arm 94a may be located at a first side 98a of the floor plate 92, and the second curved side arm 94b may be located at a second side 98b of the floor plate 92. As shown in FIG. 22, the first curved side arm 94a and the second curved side arm 94b may be configured to open facing toward one another. The first and second curved side arms 94a, 94b may define shapes similar to open and closed square brackets, respectively.

In some embodiments, as shown in FIG. 22, the top surface 96 comprises an indented portion (e.g., a channel, groove, trench, rut, or the like), and at least one of the first curved side arm 94a and the second curved side arm 94b is configured to couple to the indented portion. By coupling to the indented portion, at least one of the first curved side arm 94a and second curved side arm 94b may be configured to sit at least partially in the floor plate 92 and at least partially below the top surface 96. The top surface 96 may comprise a substantially continuous surface without an indented portion, such that at least one of the first curved side arm 94a and the second curved side arm 94b is configured to sit on top of the floor plate 92. Disregarding the indented portion, the floor plate 92 may comprise a substantially flat and level top surface 96. In some embodiments, as shown in FIG. 22 and disregarding the indented portion, the floor plate 92 comprises a bowed top surface 96 such that the outer portions of the top surface 96 located furthest from the first and second curved side arms 94a, 94b define a lesser height than a middle portion of the top surface 96. The outer portion of the top surface 96 located furthest from the first and second curved side arms 94a, 94b may define a greater height than the middle portion of the top surface 96.

In some embodiments, the floor plate 92 comprises a substantially rectangular base. It should be noted that the "base" may be considered a bottom surface of the floor plate 92 located opposite the top surface 96, wherein the base is configured to contact a floor surface. The base may define any suitable shape, including but not limited to round, ovoid, triangular, pentagonal, hexagonal, etc. In some embodiments, the floor plate 92 comprises at least one wheel and/or at least one foot coupled to the base of the floor plate 92. It should be noted that though called a light therapy device "floor" stand 90, the stand 90 may be configured to restably couple to a table, counter, desk, chair, stool, or any other indoor or outdoor surface. The floor stand 90 should not be considered to be limited to use on a floor.

Figure 23:
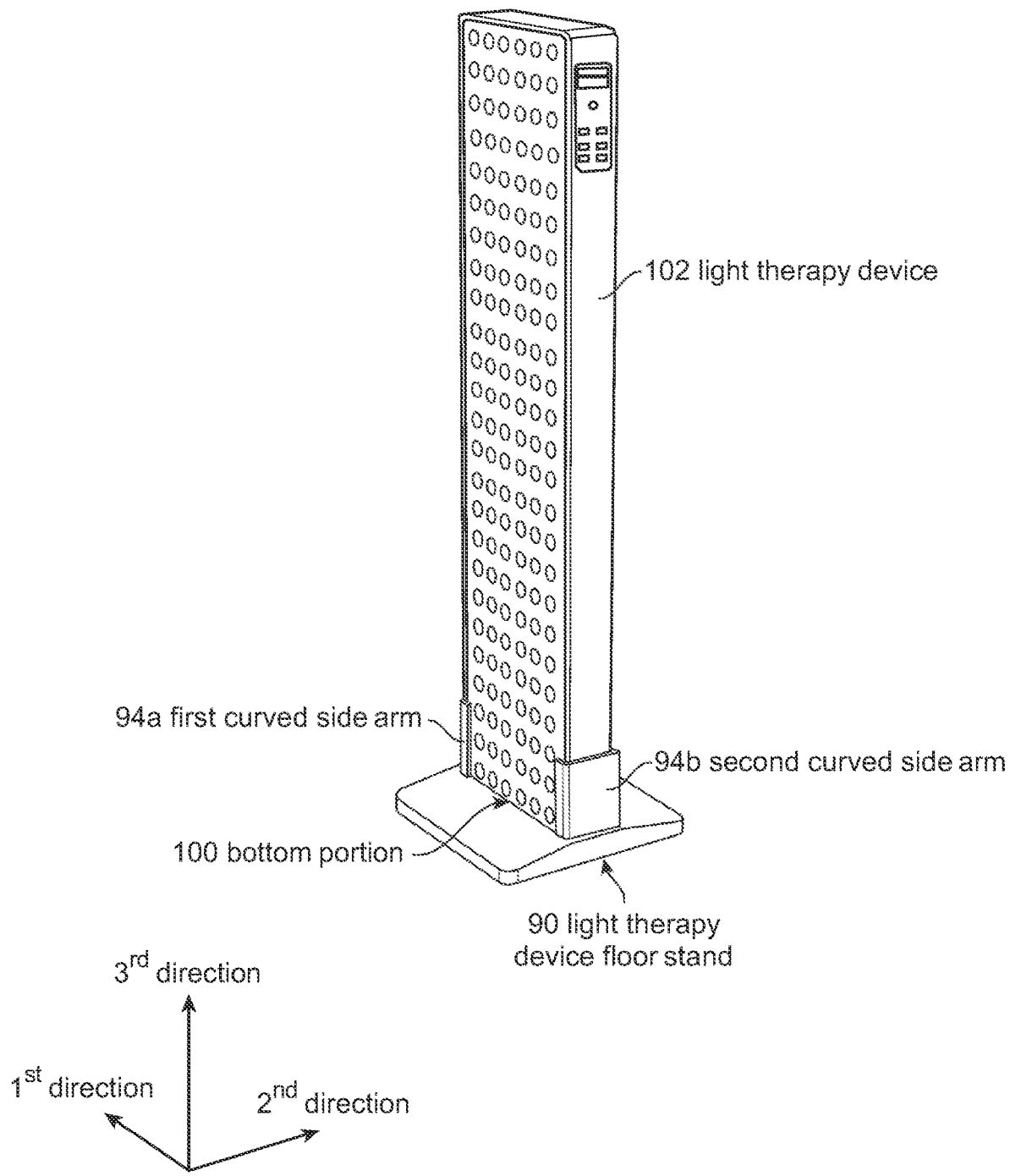
FIG. 23 illustrates a perspective view of a light therapy device coupled to a light therapy device floor stand, according to some embodiments.

FIG. 23 illustrates the floor stand 90 coupled to a light therapy device 102. The light therapy device 102 may define any number of sizes and configurations. In some embodiments, the light therapy device 102 is substantially identical to the light therapy device 30 mentioned throughout the disclosure. Each of the light therapy device 30 and the light therapy device 102 may comprise a light therapy device produced by Joovv, Inc. of Delaware, USA. For example, the light therapy device 30, 102 may comprise any of the devices disclosed in the following U.S. Nonprovisional Patent Applications and/or issued U.S. Patents: application Ser. No. 15/616,028; application Ser. No. 16/167,385; U.S. Pat. Nos. 10,478,635; 10,639,495; application Ser. No. 16/598,033; and application Ser. No. 16/904,243.

The floor stand 90 may be configured to couple to the light therapy device 102 via the first and second curved side arms 94a, 94b. In many embodiments, the first and second curved side arms 94a, 94b are configured to slidably receive a bottom portion 100 of the light therapy device 102. As previously mentioned, the floor stand 90 may include an indented portion on the top surface 96. In some embodiments, the indented portion is configured to receive at least a portion of the bottom portion 100. This may add stability to the light therapy device 102 by coupling the device 102 to the floor stand 90 via both the indentation in the floor plate 92 and the first and second curved side arms 94a, 94b.

In many embodiments, as shown by the directional indicators in FIG. 23, the floor plate 92 may extend along a first direction and a second direction perpendicular to the first direction, and the first and second curved side arms 94a, 94b may extend along a third direction perpendicular to the first direction and second direction. The light therapy device 102 may also extend along the third direction. In some embodiments, at least one of the first curved side arm 94a and the second curved side arm 94b defines a greater height than depicted in FIG. 23. As such, at least one of the first curved side arm 94a and the second curved side arm 94b may be configured to extend further up (i.e., along the third direction) the light therapy device 102. At least one of the first and second curved side arms 94a, 94b may extend along the third direction to a lesser extent than shown in FIG. 23. The first and second curved side arms 94a, 94b may be configured such that a width of the curved side arms 94a, 94b is just slightly larger than a width of the light therapy device 102. As such, the light therapy device 102 may be configured to fit snugly in the first and second curved side arms 94a, 94b with little and/or no space to move, wobble, rock, or the like.

In some embodiments, the light therapy device 102 comprises a plurality of light therapy devices 102 configured to couple to the floor stand 90. For example, the light therapy device 102 may be coupled to another light therapy device 102 in a top-to-bottom stacked formation, wherein the bottom device 102 is coupled to the floor stand 90 via the curved side arms 94a, 94b and the top device 102 is coupled to the bottom device 102 via attachment posts or a similar method. In some embodiments, a light therapy device 102 is coupled adjacent another light therapy device 102 in a side-by-side formation. In such an embodiment, the first curved side arm 94a may be configured to slidably receive an outer portion of one light therapy device 102, and the second curved side arm 94b may be configured to receive an outer portion of the other light therapy device 102. In some embodiments, the floor stand 90 comprises multiple sets of curved side arms 94a, 94b in order to facilitate coupling to a plurality of light therapy devices 102.

Table Stand System Embodiments

Figure 24:
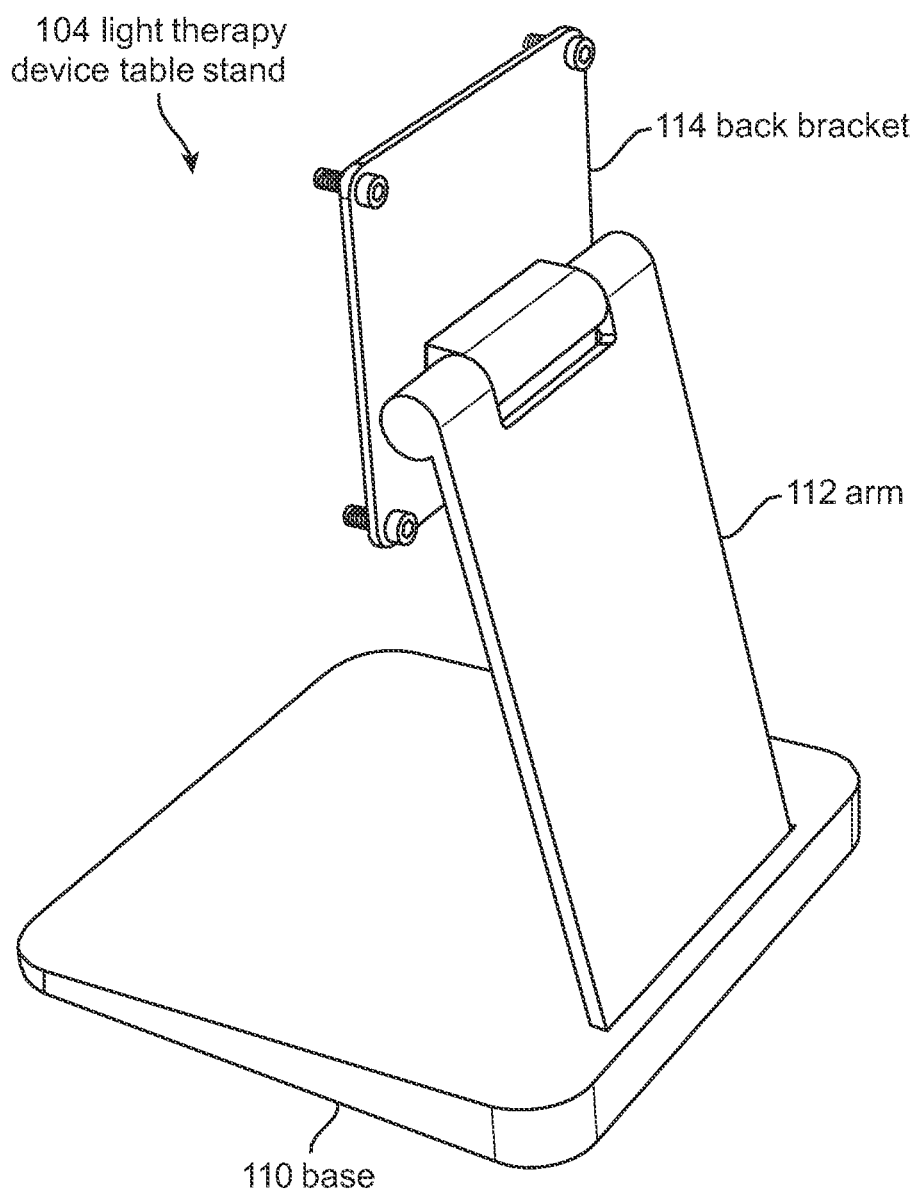
FIG. 24 illustrates a perspective view of a light therapy device table stand, according to some embodiments.
Figure 25:
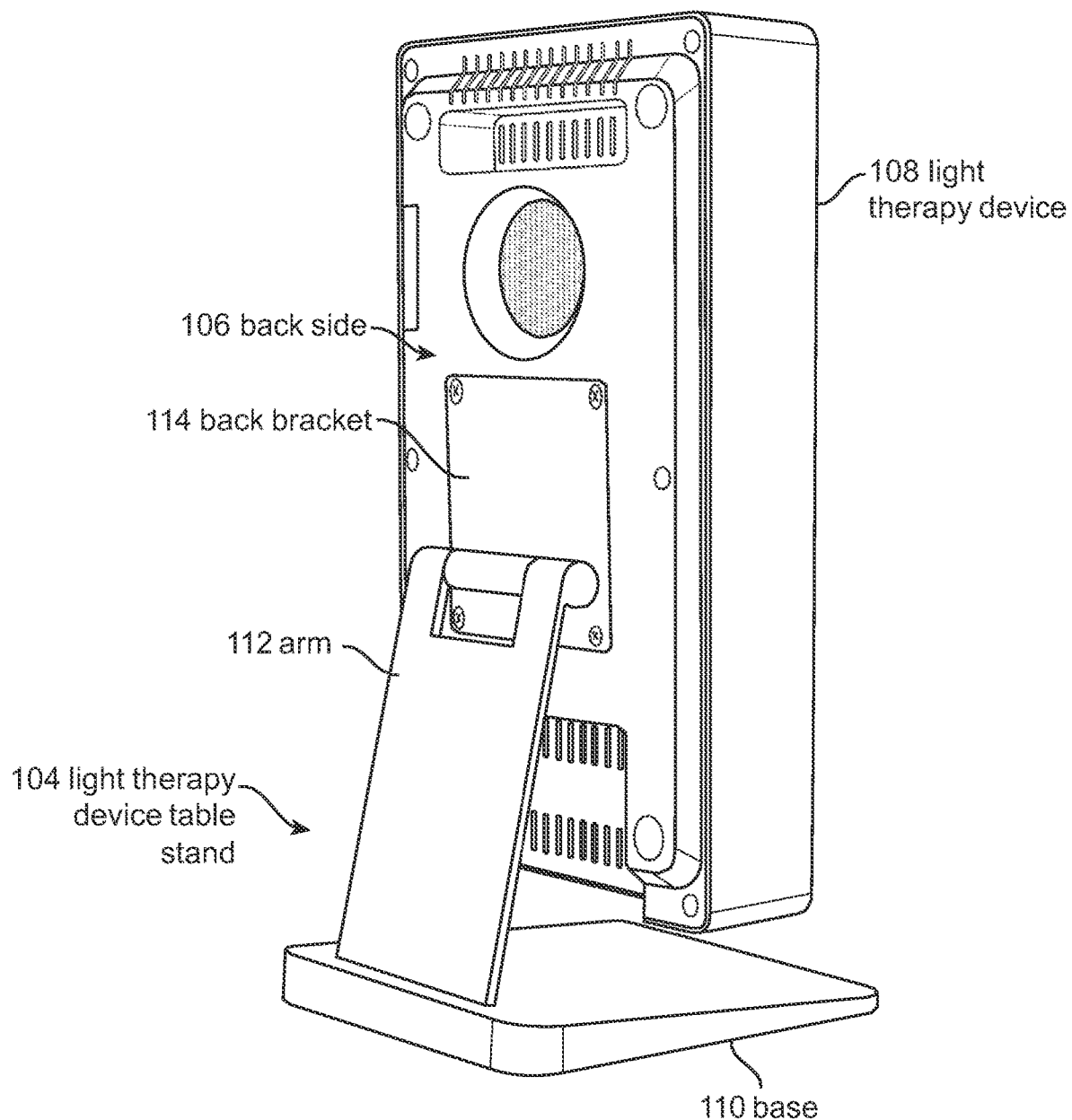
FIG. 25 illustrates a perspective view of a light therapy device coupled to a light therapy device table stand, according to some embodiments.

FIG. 24 illustrates a light therapy device table stand 104, according to some embodiments. It should be noted that though called a "table" stand 104, the stand 104 may be configured to restably couple to a variety of surfaces including, but not limited to, a ground and/or floor surface, a desk, a chair, a stool, a counter, a bed, and any other indoor and/or outdoor surface. In many embodiments, the table stand 104 includes a base 110, an arm 112, and a back bracket 114. The base 110 may be configured to contact the table and/or other surfaces. As shown in FIG. 25, the table stand 104 may be configured to couple to a light therapy device 108 via the back bracket 114. In some embodiments, the back bracket 114 is configured to couple to a back side 106 of the light therapy device 108. The back bracket 114 may detachably couple to the light therapy device 108 via any of the coupling mechanisms disclosed herein. In some embodiments, the back bracket 114 is configured to fixedly couple to the light therapy device 108 via any of the coupling mechanisms disclosed herein. The back bracket 114 may comprise a single bracket, as shown in FIGS. 24 and 25. In some embodiments, the back bracket 114 comprises a plurality of brackets.

The arm 112 may be configured to couple the back bracket 114 to the base 110. In many embodiments, the arm 112 is adjustable such that the light therapy device 108 is configured to tilt at a wide range of angles. FIG. 25 shows the light therapy device 108 situated substantially straight, which may be suitable for delivering light therapy directly in front of the device 108. In some embodiments, the light therapy device 108 is configured to tilt upwards in order to provide light therapy to an area at an angle above the device 108. For example, a user may stand in front of the device 108 when the stand 104 is restably coupled to a table, and the user may adjust the arm 112 such that the device 108 is angled upward in order to emit light toward the upper torso and/or head region of the user. Alternatively, the user may adjust the arm 112 such that the device 108 is angled downward in order to emit light towards the lower torso and/or legs of the user. The arm 112 may comprise a single-arm, as shown in FIGS. 24 and 25. In some embodiments, the arm 112 comprises a plurality of arms.

The table stand 104 may be configured to couple to a plurality of light therapy devices 108. In some embodiments, the table stand 104 comprises a plurality of back brackets 114 and a plurality of arms 112 in order to couple to a plurality of light therapy devices 108. The light therapy devices 108 may be configured to couple to one another independent of the table stand 104, such that the table stand 104 is configured to couple to multiple light therapy devices 108 when the table stand 104 comprises a single arm 112 and a single back bracket 114. For example, the light therapy device 108 may be coupled to another light therapy device 108 in a top-to-bottom stacked configuration such that one light therapy device 108 is coupled on top of another light therapy device 108. In such an embodiment, the back bracket 114 may be configured to couple to either the top or bottom light therapy device 108.

Similar to the light therapy device 30 and the light therapy device 102, the light therapy device 108 may comprise a light therapy device produced by Joovv, Inc. of Delaware, USA. For example, the light therapy device 30, 102, or 108 may comprise any of the devices disclosed in the following U.S. Nonprovisional Patent Applications and/or issued U.S. Patents: application Ser. No. 15/616,028; application Ser. No. 16/167,385; U.S. Pat. Nos. 10,478,635; 10,639,495; application Ser. No. 16/598,033; and application Ser. No. 16/904,243.

Door Mount System Embodiments

Figure 26:
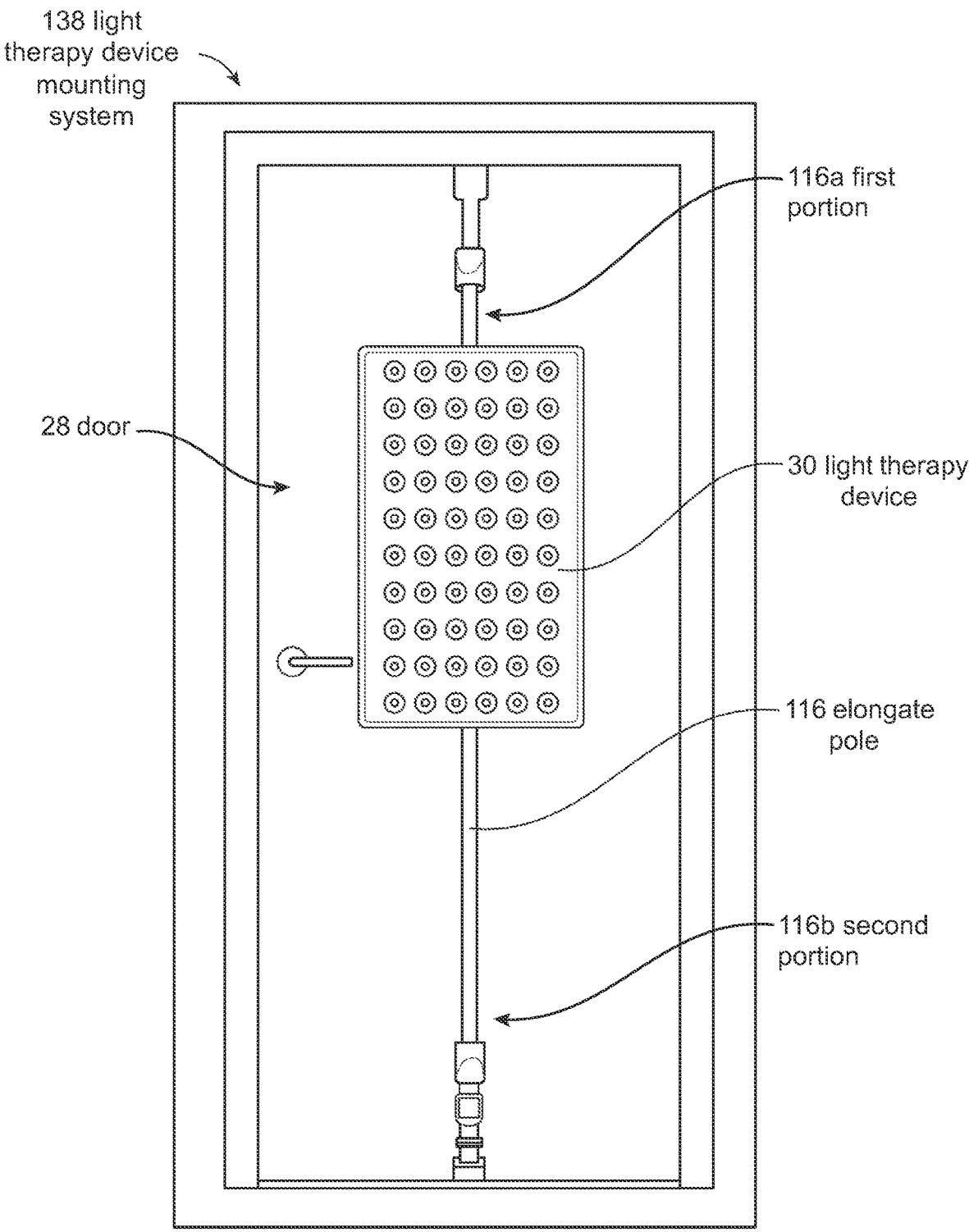
FIG. 26 illustrates a front view of a light therapy device mounting system coupled to a door, according to some embodiments.

FIG. 26 illustrates an embodiment of a light therapy device mounting system 138. As shown, the system 138 may be configured to couple to a door 28. In many embodiments, the system 138 includes an elongate pole 116 comprising a first portion 116a and a second portion 116b. The first portion 116a and second portion 116b will be discussed further with reference to FIG. 27. In some embodiments, a light therapy device 30 is configured to couple to the elongate pole 116. The manner in which the light therapy device 30 couples to the elongate pole 116 will be discussed in greater detail later in the disclosure. Though a single light therapy device 30 is shown coupled to the elongate pole 116, multiple light therapy devices may couple to the elongate pole 116. In some embodiments, the light therapy device 30 comprises a larger device 30 than depicted in FIG. 26. The light therapy device 30 may comprise a smaller device 30 than depicted in FIG. 26. The system 138 may be configured to include a plurality of elongate poles 116 coupled to the door 28, and each elongate pole 116 may be configured to couple to at least one light therapy device 30.

Figure 27:
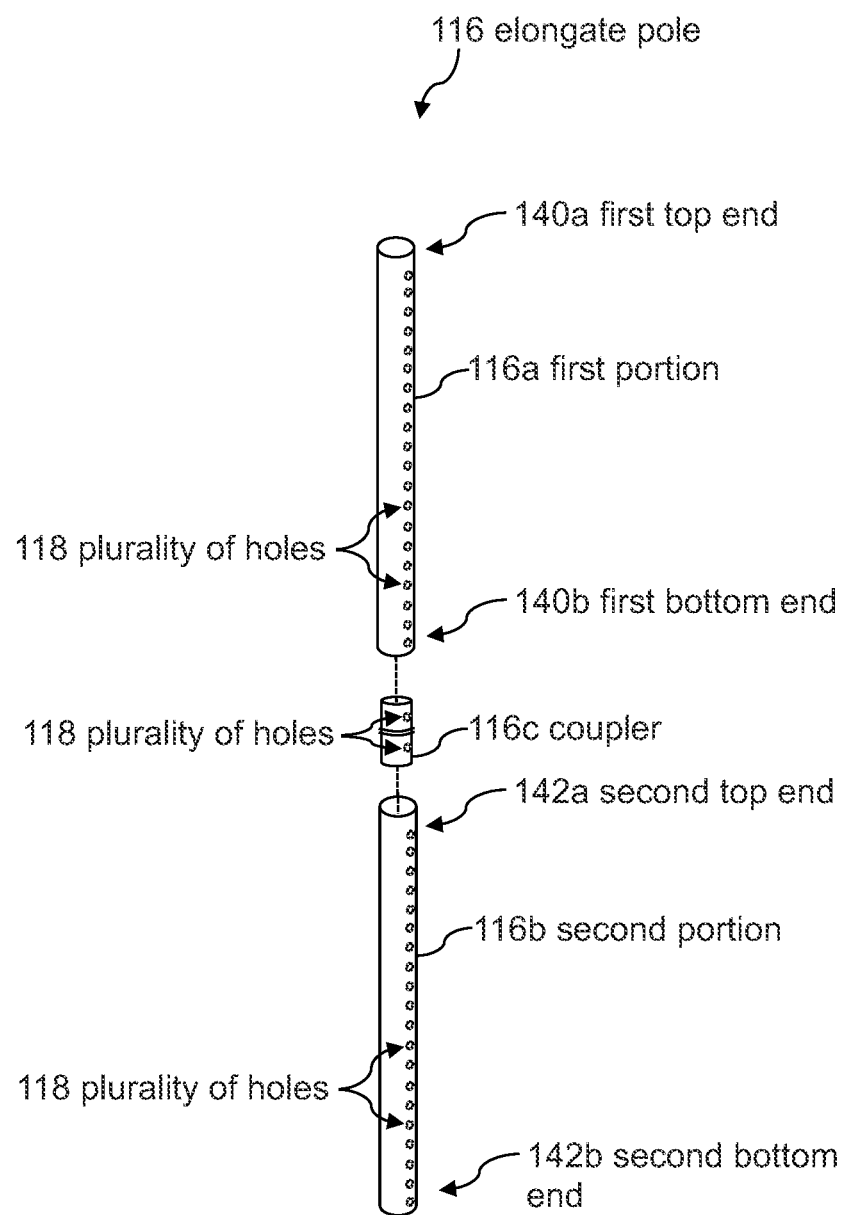
FIG. 27 illustrates a perspective view of an elongate pole comprising a first portion, a second portion, and a coupler, according to some embodiments.

FIG. 27 illustrates the elongate pole 116, including the first portion 116a, the second portion 116b, and a coupler 116c. As shown in FIG. 27, each of the first portion 116a, second portion 116b, and coupler 116c may include a plurality of holes 118. It should be noted that, in terms of function, the elongate pole 116 may be similar to the elongate pole 12 previously discussed in this disclosure. However, in terms of form, the elongate pole 116 differs from the elongate pole 12 due to the inclusion of the first portion 116a, the second portion 116b, and the coupler 116c.

In some embodiments, the coupler 116c is configured to couple the first portion 116a and second portion 116b. As illustrated in FIG. 27, the first portion 116a may comprise a first top end 140a and a first bottom end 140b. Similarly, the second portion 116b may comprise a second top end 142a and a second bottom end 142b. In some embodiments, the first bottom end 140b and second top end 142a are configured to receive the coupler 116c, thereby coupling the first portion 116a and the second portion 116b with the coupler 116c located therebetween. In some embodiments, at least one mechanical fastener (such as a bolt, screw, pin, or the like) is configured to couple the coupler 116c to the first portion 116a and second portion 116b via the plurality of holes 118. For example, a mechanical fastener may be configured to extend through a bottom hole of the first portion 116a and a top hole of the coupler 116c, thereby coupling the first portion 116a to the coupler 116c. Similarly, another mechanical fastener may be configured to extend through a top hole of the second portion 116b and a bottom hole of the coupler 116c, thereby coupling the second portion 116b to the coupler 116c.

The first portion 116a and second portion 116b may define substantially the same length, such that when the elongate pole 116 is fully assembled, the coupler 116c is located substantially in the middle of the elongate pole 116. In some embodiments, the first portion 116a and the second portion 116b define different lengths. It should be noted that when assembled, the coupler 116c may be flush with the first portion 116a and the second portion 116b, such that a slider mount 124 (shown in FIG. 30) is configured to smoothly slide along a full length of the elongate pole 116.

Figure 28A:
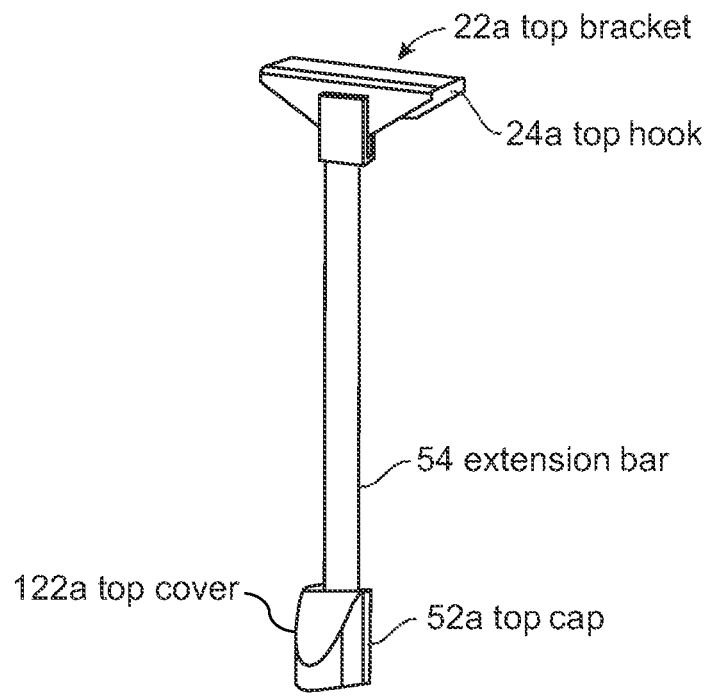
FIGS. 28A and 28B illustrate front and back views, respectively, of a top bracket, according to some embodiments.
Figure 28B:
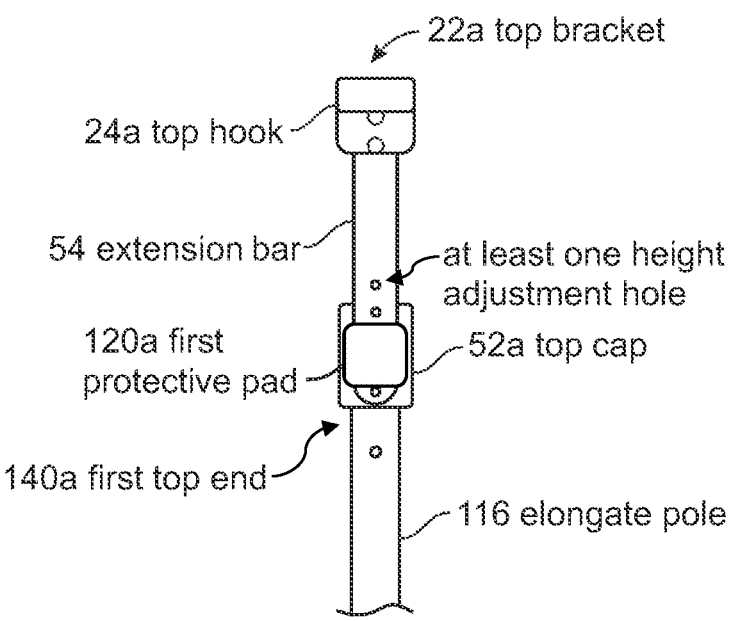

FIGS. 28A and 28B, similar to FIGS. 3A and 3B, illustrate front and back views, respectively, of a top bracket 22a. In some embodiments, the top bracket 22a shown in FIGS. 28A and 28B is substantially similar to the top bracket 22a shown in FIGS. 3A and 3B. The top bracket 22a may comprise a top cap 52a, a top hook 24a, and an extension bar 54. In some embodiments, the top bracket 22a is configured to slidably couple to the first top end 140a of the first portion 116a of the elongate pole 116. The top bracket 22a may be slidably coupled via the top cap 52a, which is configured to receive the first portion 116a of the elongate pole 116. The top cap 52a may include two pieces configured to snap together around the elongate pole 116. In some embodiments, one piece (e.g., a back piece) of the top cap 52a is configured to receive the elongate pole 116, and the second piece (e.g., the top cover 122a) is configured to cover the first top end 140a and the first piece of the cap 52a, thus providing a cosmetic appearance to the top cap 52a.

The top cap 52a may be configured to couple to the extension bar 54. As shown in FIG. 28B, the extension bar 54 may include at least one height adjustment hole. In many embodiments, the at least one height adjustment hole is configured to couple to the top cap 52a via at least one coupling mechanism, such as a bolt, pin, screw, or similar mechanism. The at least one coupling mechanism may be located on a back portion of the top cap 52a, where a back portion may be considered a portion opposite a portion of the system 138 coupled to the light therapy device 30. For example, in the embodiment shown in FIG. 26, the system 138 is configured such that the light therapy device 30 faces away from the door 28. In such an embodiment, the back portion of the top cap 52a may be considered the portion located adjacent the door 28. In order to protect the door 28 from the top cap 52a, the top bracket 22a may include a first protective pad 120a. The first protective pad 120a may comprise any soft and/or cushioned surface. In addition to protecting the door 28, the first protective pad 120a may also provide friction to reduce side-to-side movement of the top bracket 22a against the door 28. In some embodiments, the at least one height adjustment hole and the at least one coupling mechanism are located within the top cap 52a. The at least one height adjustment hole and the at least one coupling mechanism may be located on a front portion located opposite the back portion of the top cap 52a.

Figure 29A:
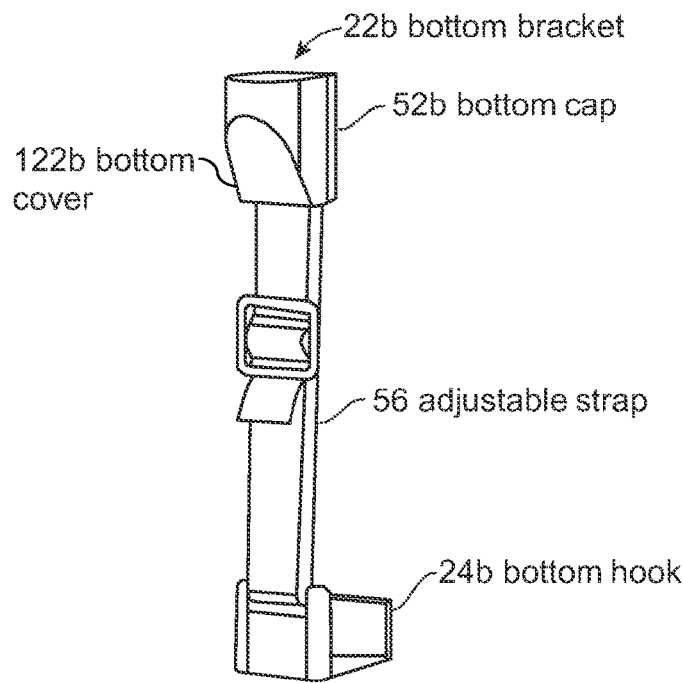
FIGS. 29A and 29B illustrate front and back views, respectively, of a bottom bracket, according to some embodiments.
Figure 29B:
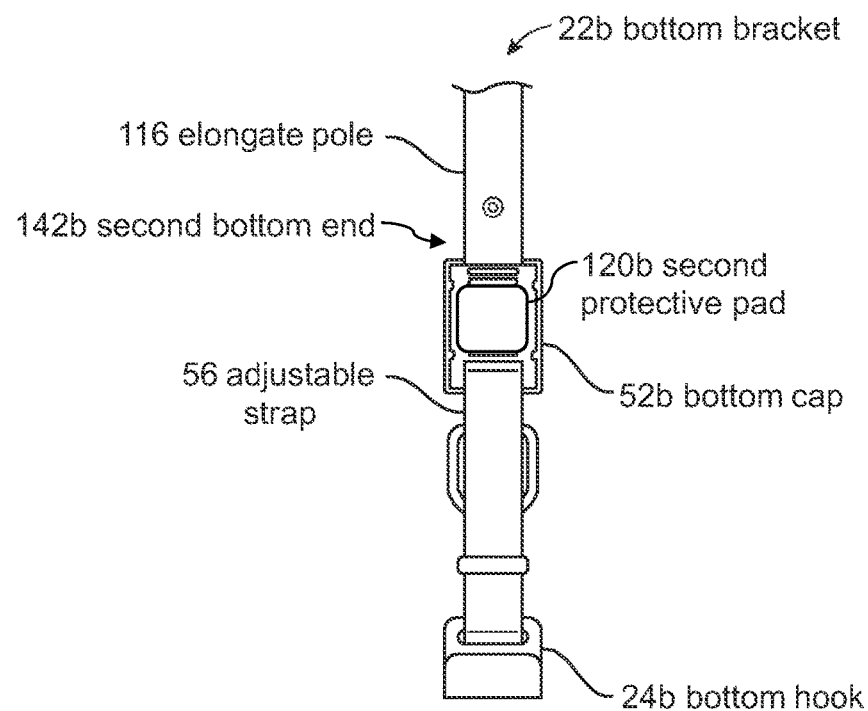

FIGS. 29A and 29B are similar to FIGS. 28A and 28B; however, they illustrate the bottom bracket 22b rather than the top bracket 22a. It should be noted that FIGS. 29A and 29B are also similar to FIGS. 4A and 4B, and the bottom bracket 22b of FIGS. 29A and 29B may be substantially similar to the bottom bracket 22b of FIGS. 4A and 4B. As shown, in some embodiments, the bottom bracket 22b includes a bottom cap 52b, an adjustable strap 56, and a bottom hook 24b. The bottom cap 52b may be configured to slidably couple the bottom bracket 22b to the second bottom end 142b of the second portion 116b of the elongate pole 116. In some embodiments, the bottom cap 52b is configured to slidably receive the second bottom end 142b. The bottom cap 52b may include two pieces configured to snap together around the elongate pole 116. In some embodiments, one piece (e.g., a back piece) of the bottom cap 52b is configured to receive the elongate pole 116, and the second piece (e.g., the bottom cover 122b) is configured to cover the second bottom end 142b and the first piece of the cap 52b, thus providing a cosmetic appearance to the bottom cap 52b. The bottom cap 52b may be configured to store the excess length of the adjustable strap 56 after the strap 56 is tightened and/or loosened. In order to protect the door 28 from the bottom cap 52b, the bottom bracket 22b may include a second protective pad 120b. The second protective pad 120b may comprise any soft and/or cushioned surface. In addition to protecting the door 28, the second protective pad 120b may also provide friction to reduce side-to-side movement of the bottom bracket 22b against the door 28.

In some embodiments, the bottom cap 52b is configured to couple to the adjustable strap 56. The adjustable strap 56 may loop around a portion of the bottom cap 52b. In some embodiments, the portion comprises at least one of a back piece, a front piece, and an internal piece of the bottom cap 52b. The portion may comprise a horizontal bar or similar portion. The adjustable strap 56 may couple to the bottom cap 52b in any other suitable way. In many embodiments, the adjustable strap 56 comprises a flexible strap and an adjusting mechanism. The adjusting mechanism may comprise a strap adjuster, a buckle, a slider, a cord lock, or any similar adjusting mechanism. In some embodiments, the adjusting mechanism is configured to at least one of tighten and loosen the adjustable strap 56. Tightening the adjustable strap 56 may facilitate tightening the system 138 by increasing the tension between the bottom hook 24b and the bottom cap 52b, and, therefore, between the bottom hook 24b and the elongate pole 116. Tightening the system 138 may be desirable in order to reduce the amount of movement of the system 138 on the door 28, particularly when the door 28 is moved between a closed position and an open position, and vice versa. Loosening the adjustable strap 56 may reduce the tension between the bottom hook 24b and the bottom cap 52b, and, therefore, between the bottom hook 24b and the elongate pole 116, thereby facilitating loosening of the system 138 so that the system 138 may be removed from and/or adjusted on the door 28.

In some embodiments, the system 138 is arranged such that the top hook 24a is configured to couple to the door 28, then the bottom hook 24b is configured to couple to the door 28, then the adjustable strap 56 is configured to tighten. Similar to the system 10 shown in FIG. 2, the system 138 may be configured to couple to the door 28 such that the top hook 24a receives a top portion of the door 28 and the bottom hook 24b receives a bottom portion of the door 28.

Figure 30:
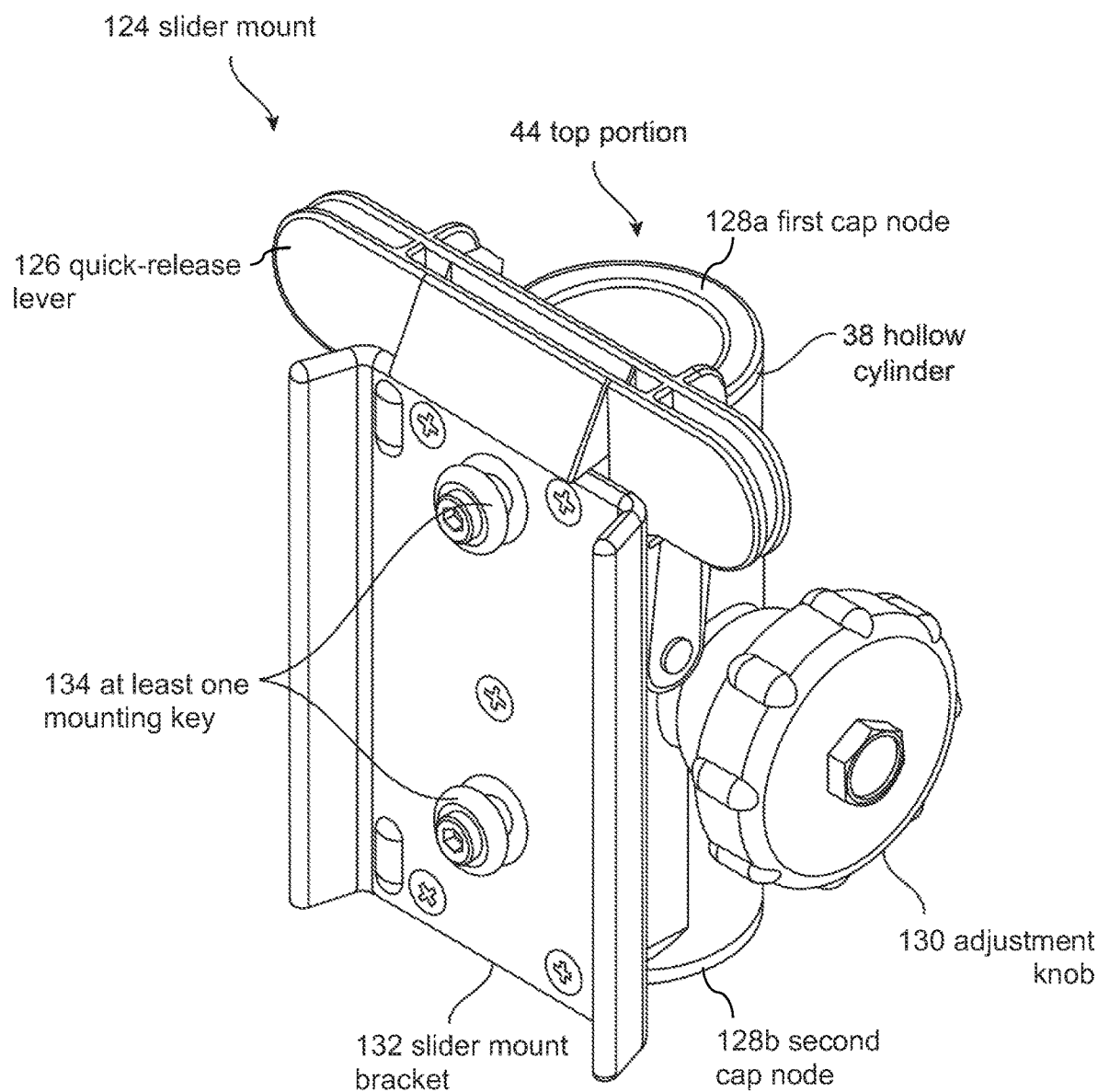
FIG. 30 illustrates a perspective view of a slider mount, according to some embodiments.

FIG. 30 illustrates a perspective view of a slider mount 124, according to some embodiments. It should be noted that the slider mount 124 may be substantially the same as the mounting device 20 previously discussed in this disclosure, in particular with reference to FIGS. 5, 6, and 7. The term "slider mount 124" may be used interchangeably with "mounting device 20." Similarly, the following terms may be used interchangeably to refer to the same components: "clip 42" and "quick-release lever 126," "mounting device bracket 40" and "slider mount bracket 132," "knob 46" and "adjustment knob 130," and "at least one projection 37" and "at least one mounting key 134."

As discussed with reference to FIG. 5, the slider mount 124 may include a hollow cylinder 38, a slider mount bracket 132, a quick-release lever 126, and an adjustment knob 130. The mounting device 20 may also include at least one mounting key 134 coupled to a front-facing surface of the slider mount bracket 132, where the at least one mounting key 134 is configured to couple to a light therapy device 30, as shown in FIG. 7. In some embodiments, the quick-release lever 126 is located at a top portion 44 of the slider mount 124, and is configured to serve as a locking mechanism for coupling the slider mount 124 to the light therapy device 30, as previously discussed. The quick-release lever 126 may be located at a bottom portion opposite the top portion. The adjustment knob 130 may be coupled to a side portion of the hollow cylinder 38. The adjustment knob 130 may function substantially the same as the knob 46, which was discussed in great detail with reference to FIG. 6. The slider mount bracket 132 may be configured to couple to the at least one of the quick-release lever 126 and the hollow cylinder 38 via any of the coupling mechanisms disclosed herein.

The hollow cylinder 38 may be configured to slidably receive the elongate pole 116. In some embodiments, the hollow cylinder 38 includes a first cap node 128a and a second cap node 128b configured to at least one of substantially surround and cover a top edge and bottom edge, respectively, of the cylinder 38. In many embodiments, the slider mount 124 is configured to couple to the elongate pole 116 via at least one hole of the plurality of holes 118, shown in FIG. 27.

Stand System Embodiments

Figure 31:
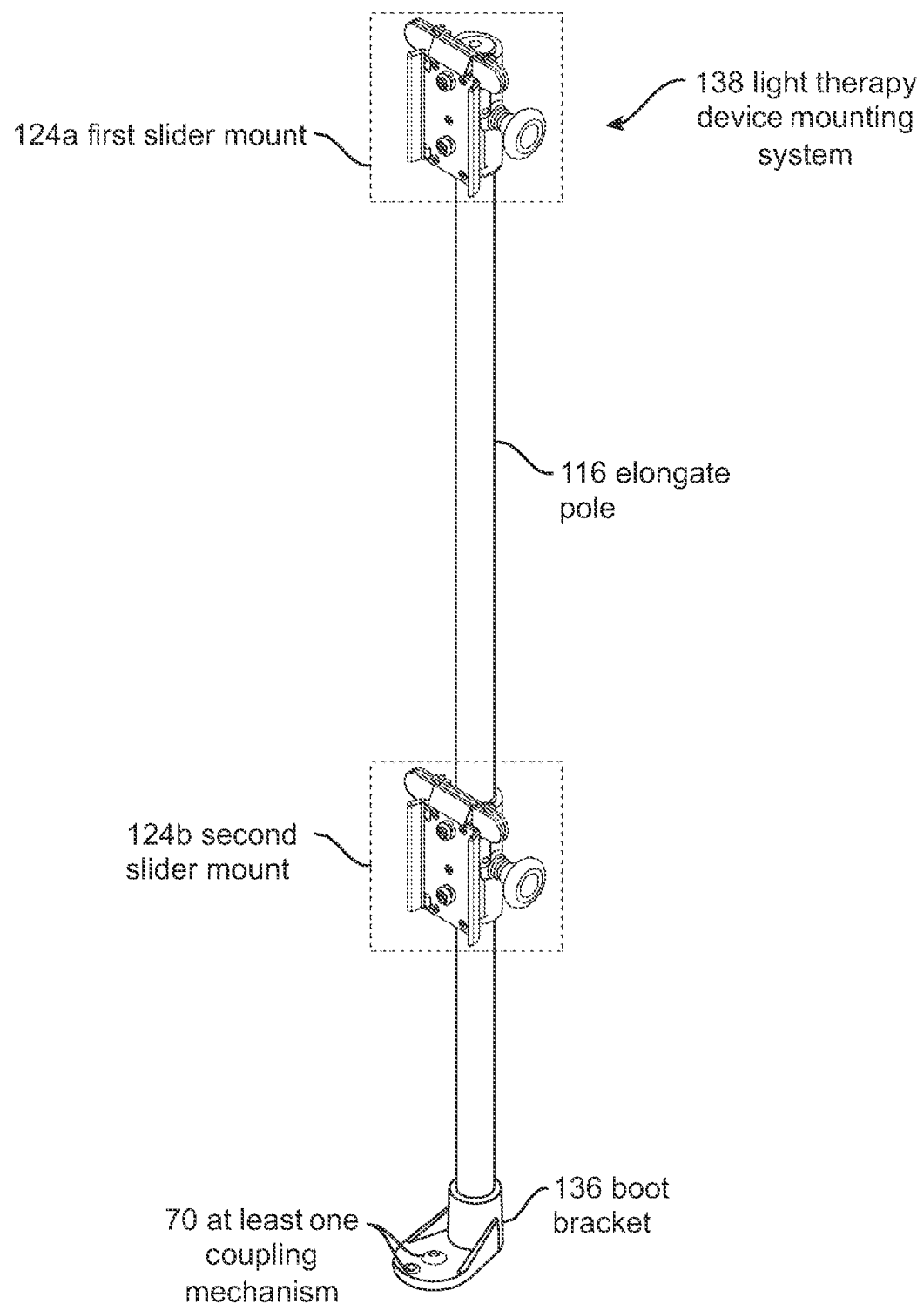
FIG. 31 illustrates a perspective view of a light therapy device mounting system including two slider mounts, according to some embodiments.

FIG. 31 illustrates an embodiment of the light therapy device mounting system 138 including a first slider mount 124a and a second slider mount 124b coupled to the elongate pole 116. As previously discussed, multiple light therapy devices may couple to the elongate pole 116, via multiple slider mounts 124. FIG. 31 also shows the elongate pole 116 coupled to a boot bracket 136. It should be noted that the boot bracket 136 may be substantially the same as bottom base 58 shown in, and discussed with reference to, FIGS. 9, 12, 15, 17, and 19-21. Accordingly, the boot bracket 136 may be configured to couple the elongate pole 116 to at least one of a fixed stand and a mobile stand, as previously discussed in this disclosure.

Materials

Any of the components disclosed herein, including but not limited to, the elongate pole 12, the mounting device 20, the top hook 24a, the bottom hook 24b, the light therapy device bracket 32, the at least one projection 37, the hollow cylinder 38, the mounting device bracket 40, the clip 42, the knob 46, the protrusion 48, the top cap 52a, the bottom cap 52b, the extension bar 54, the bottom base 58, the mobile stand 60, the plurality of wheels 62, the at least one coupling mechanism 70, the fixed stand 72, the wall bracket 76, the plurality of feet 82, the C-shaped hook 84, the at least one brace 88, the light therapy device floor stand 90, the floor plate 92, the first curved side arm 94a, the second curved side arm 94b, the light therapy device table stand 104, the base 110, the arm 112, and/or the back bracket 114 may comprise any suitable material or combination of materials. For example, the components may comprise any metallic, plastic, or combination material. Metallic materials may comprise steel, aluminum, or any other metal or combination of metals. In many embodiments, the components are comprised of durable material(s) configured to withstand everyday wear-and-tear and more significant potential damage, such as being dropped, bumped, knocked against a wall and/or door, etc. The components may comprise any color, whether the natural color of a material (e.g., metallic components may be silver in color) or an applied color (e.g., paint, powder coating, etc.).

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1, and embodiments described in other sections may apply to and be combined with embodiments described within the "Topic 1" section.

The various features and processes described above may be used independently of one another or may be combined in various ways. All possible combinations and subcombinations are intended to fall within the scope of this disclosure. In addition, certain methods, events, states, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

The term "substantially" is used to mean "completely" or "nearly completely." For example, the disclosure includes, "The plurality of holes 14 may extend down substantially the full length of the pole 12." In this context, "substantially the full length of the pole" means that the plurality of holes may extend down completely or nearly completely the full length of the pole. The plurality of holes may extend down 80% of the pole and fall within the understood meaning of "substantially" as used in this disclosure.

The term "about" is used to mean "approximately." For example, the disclosure includes, "The extension bar 54 may be configured to accommodate door heights of about 80 inches." In this context, "about 80 inches" means "approximately" 80 inches. A door height between 75 and 85 inches may fall within an acceptable range of "about 80 inches".

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A light therapy device mounting system, comprising:
an elongate pole defining a first end and a second end located opposite the first end, the elongate pole including a plurality of holes;
a slider mount slidably coupled to the elongate pole via at least one hole of the plurality of holes;
a top bracket slidably coupled to the first end of the elongate pole, wherein the top bracket comprises a top hook for receiving a top portion of a door, a top cap coupled to the first end of the elongate pole, and an extension bar configured to couple the top cap to the top hook;
a bottom bracket slidably coupled to the second end of the elongate pole, wherein the bottom bracket comprises a bottom hook for receiving a bottom portion of the door; and
a light therapy device detachably coupled to the slider mount, wherein the light therapy device comprises a light therapy device bracket coupled to a back side of the light therapy device.

2. The light therapy device mounting system of claim 1, wherein the light therapy device bracket includes a plurality of keyhole brackets,
wherein the slider mount is coupled to at least one mounting key, and
wherein the plurality of keyhole brackets is configured to receive the at least one mounting key, thereby coupling the light therapy device bracket to the slider mount.

3. The light therapy device mounting system of claim 2, wherein the slider mount comprises:
a hollow cylinder configured to slidably receive the elongate pole;
a first cap node coupled to a first end of the hollow cylinder;
a second cap node coupled to a second end of the hollow cylinder, wherein the second end is located opposite the first end;
a slider mount bracket coupled to the hollow cylinder, wherein the slider mount bracket is configured to detachably couple to the light therapy device via the plurality of keyhole brackets of the light therapy device bracket located on the back side of the light therapy device;
a quick release lever coupled to the hollow cylinder and the slider mount bracket, wherein the quick release lever is located on a top portion of the slider mount bracket and is configured to retain the light therapy device bracket to the slider mount bracket; and
an adjustment knob coupled to a side portion of the hollow cylinder, wherein the adjustment knob comprises a protrusion that extends into an inner portion of the hollow cylinder, and wherein the protrusion is configured to couple to at least one hole of the plurality of holes located on the elongate pole.

4. The light therapy device mounting system of claim 3, wherein the elongate pole is elongate in a first direction and the adjustment knob is configured to slide in a second direction perpendicular to the first direction, wherein sliding the adjustment knob in the second direction is configured to perform an action selected from the group consisting of releasing the protrusion from at least one hole of the plurality of holes, coupling the protrusion to at least one hole of the plurality of holes, and combinations thereof.

5. The light therapy device mounting system of claim 4, wherein the adjustment knob is configured to rotate in a third direction perpendicular to the first direction and the second direction, wherein rotating the adjustment knob is configured to perform an action selected from the group consisting of tightening the adjustment knob, loosening the adjustment knob, and combinations thereof.

6. The light therapy device mounting system of claim 5, wherein the quick release lever is configured to move along the third direction to perform an action selected from the group consisting of retaining the light therapy device bracket, releasing the light therapy device bracket, and combinations thereof.

7. The light therapy device mounting system of claim 1, wherein the top bracket further comprises
a top cover configured to at least partially conceal the top cap.

8. The light therapy device mounting system of claim 7, wherein the extension bar comprises at least one height adjustment hole, the extension bar configured to raise and lower a height of the top hook.

9. The light therapy device mounting system of claim 8, wherein the extension bar comprises a first extension bar defining a first length, the system further comprising a second extension bar defining a second length, wherein the second length is greater than the first length, and wherein the first extension bar and the second extension bar are configured to interchangeably couple to the top bracket.

10. The light therapy device mounting system of claim 7, the bottom bracket comprising:
a bottom cap coupled to the second end of the elongate pole;
an adjustable strap configured to couple the bottom cap to the bottom hook; and
a bottom cover configured to at least partially conceal the bottom cap.

11. The light therapy device mounting system of claim 10, wherein the adjustable strap is configured to perform an action selected from the group consisting of tightening, loosening, and combinations thereof, thereby increasing or decreasing tension between the bottom cap and the bottom hook.

12. The light therapy device mounting system of claim 7, further comprising a first protective pad coupled to the top bracket and a second protective pad coupled to the bottom bracket, wherein the first protective pad and the second protective pad are configured to protect a surface of the door.

13. The light therapy device mounting system of claim 1, wherein the slider mount comprises a first slider mount and the light therapy device comprises a first light therapy device, the system further comprising a second slider mount slidably coupled to the elongate pole and a second light therapy device detachably coupled to the second slider mount.

14. A light therapy device mounting system, comprising:
an elongate pole defining a first end and a second end located opposite the first end, the elongate pole including a plurality of holes;
a slider mount slidably coupled to the elongate pole via at least one hole of the plurality of holes;
a boot bracket configured to receive the second end of the elongate pole, wherein the boot bracket is configured to couple to a fixed stand comprising a plurality of feet configured to contact a ground surface;
a light therapy device detachably coupled to the slider mount, wherein the light therapy device comprises a light therapy device bracket coupled to a back side of the light therapy device; and a wall bracket snapably coupled to the elongate pole, wherein the wall bracket comprises a C-shaped hook located on a first surface of the wall bracket.

15. The light therapy device mounting system of claim 14, wherein the wall bracket comprises a plurality of holes configured to receive at least one coupling mechanism to thereby couple the wall bracket to a wall surface.

16. The light therapy device mounting system of claim 15, wherein the C-shaped hook is configured to snapably couple to the elongate pole, and the plurality of holes are located on a second surface of the wall bracket opposite the first surface, such that when the wall bracket is snapably coupled to the elongate pole and the wall bracket is coupled to the wall surface via the at least one coupling mechanism, the elongate pole is thereby coupled to the wall surface via the wall bracket.

17. A light therapy device mounting system, comprising:

an elongate pole defining a first end and a second end located opposite the first end, the elongate pole including a plurality of holes;

a slider mount slidably coupled to the elongate pole via at least one hole of the plurality of holes;

a boot bracket configured to receive the second end of the elongate pole, wherein the boot bracket is configured to couple to one of a first mobile stand defining a first size and comprising a first plurality of wheels configured to contact a ground surface and a second mobile stand defining a second size and comprising a second plurality of wheels configured to contact the ground surface, wherein the second size is larger than the first size; and a light therapy device detachably coupled to the slider mount, wherein the light therapy device comprises a light therapy device bracket coupled to a back side of the light therapy device.

18. The light therapy device mounting system of claim 17, wherein the first mobile stand is sized and configured to couple to the boot bracket, thereby coupling the first mobile stand to the elongate pole.

19. The light therapy device mounting system of claim 18, wherein the second mobile stand is sized and configured to couple to a plurality of boot brackets, thereby coupling the second mobile stand to a plurality of elongate poles.

20. The light therapy device mounting system of claim 17, wherein the first plurality of wheels comprises four wheels and wherein the second plurality of wheels comprises four wheels.

* * * * *